US009453198B2

(12) United States Patent
Studer et al.

(10) Patent No.: US 9,453,198 B2
(45) Date of Patent: Sep. 27, 2016

(54) METHOD OF NOCICEPTOR DIFFERENTIATION OF HUMAN EMBRYONIC STEM CELLS AND USES THEREOF

(75) Inventors: Lorenz Studer, New York, NY (US); Stuart M. Chambers, New York, NY (US); Yuchen Qi, New York, NY (US); Yvonne Marissa Mica, Danbury, CT (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 358 days.

(21) Appl. No.: 13/697,274

(22) PCT Filed: May 19, 2011

(86) PCT No.: PCT/US2011/037179
§ 371 (c)(1),
(2), (4) Date: Jan. 22, 2013

(87) PCT Pub. No.: WO2011/149762
PCT Pub. Date: Dec. 1, 2011

(65) Prior Publication Data
US 2013/0183674 A1 Jul. 18, 2013

Related U.S. Application Data

(60) Provisional application No. 61/396,257, filed on May 25, 2010.

(51) Int. Cl.
*C12N 5/00* (2006.01)
*C12N 5/0793* (2010.01)
*C12N 5/071* (2010.01)

(52) U.S. Cl.
CPC ............. *C12N 5/062* (2013.01); *C12N 5/0626* (2013.01); *C12N 2501/13* (2013.01); *C12N 2501/15* (2013.01); *C12N 2501/155* (2013.01); *C12N 2501/16* (2013.01); *C12N 2501/415* (2013.01); *C12N 2501/727* (2013.01); *C12N 2506/02* (2013.01); *C12N 2506/45* (2013.01)

(58) Field of Classification Search
CPC .............................. C12N 5/062; C12N 5/0626
See application file for complete search history.

(56) References Cited

U.S. PATENT DOCUMENTS

| 2004/0087478 | A1 | 5/2004 | Gillen et al. | 514/1 |
|---|---|---|---|---|
| 2004/0214324 | A1 | 10/2004 | Isacson et al. | 435/368 |
| 2010/0093090 | A1 | 4/2010 | Deng et al. | 435/377 |
| 2010/0099772 | A1* | 4/2010 | Bean et al. | 514/626 |

FOREIGN PATENT DOCUMENTS

| EP | 1645286 A1 | 4/2006 |
|---|---|---|
| WO | WO 2007/113505 A2 | 10/2007 |
| WO | WO 2008/018190 A1 | 2/2008 |
| WO | WO 2009/099152 A1 | 8/2009 |
| WO | WO 2010/096496 A2 | 8/2010 |
| WO | WO 2010/141622 A2 | 12/2010 |
| WO | WO 2011/019092 A1 | 2/2011 |
| WO | WO 2011/108766 A1 | 9/2011 |
| WO | WO 2011/159726 A2 | 12/2011 |

OTHER PUBLICATIONS

Stem Cells: Scientific Progress and Future Research Directions. Department of Health and Human Services. Jun. 2001. Chapter 4. pp. 23-42.*
Aoki, et al., "Sox10 Regulates the Development of Neural Crest-Derived Melanocytes in Xenopus," *Developmental Biology*, 259(1):19-33 (2003).
Bansal, et al., "Specific Inhibitor of FGF Receptor Signaling: FGF-2-Mediated Effects on Proliferation, Differentiation, and MAPK Activation are Inhibited by PD173074 in Oligodendrocyte-Lineage Cells," *Journal of Neuroscience, Research*, 74(4):486-493 (2003).
Bennett, et al., "Regulation of Wnt Signaling During Adipogenesis," *J Biol Chem.*, 277(34):30998-31004 (2002).
Brivanlou and Darnell, "Signal Transduction and the Control of Gene Expression," *Science*, 295(5556):813-818 (2002).
Bystron, et al., "The First Neurons of the Human Cerebral Cortex," *Nat Neurosci.*, 9(7):880-886 (2006).
Cadigan and Liu, "Wnt Signaling: Complexity at the Surface," *J Cell Sci.*, 119(Pt 3):395-402 (2006).
Chambers, et al., "Highly Efficient Neural Conversion of Human ES and iPS Cells by Dual Inhibition of SMAD Signaling," *Nat Biotechnol.*, 27(3):275-280 (2009).
Cuny, et al., "Structure-Activity Relationship Study of Bone Morphogenetic Protein (BMP) Signaling Inhibitors," *Bioorg Med Chem Lett.*, 18(15):4388-4392 (2008).
"DAPI Nucleic Acid Stain." Molecular Probes, *Invitrogen, Ltd.* pp. 1-5 (2006), pp. 1-5.
Doble and Woodgett, "GSK-3: Tricks of the Trade for a Multi-Tasing Kinase," *Journal of Cell Science*, 116(7):1175-1186 (2003).
Dorsky, et al., "Control of Neural Crest Cell Fate by the Wnt Signalling Pathway," *Nature*, 396(6709):370-373 (1998).

(Continued)

*Primary Examiner* — Marcia S Noble
(74) *Attorney, Agent, or Firm* — Baker Botts L.L.P.

(57) ABSTRACT

The present invention relates to the field of stem cell biology, in particular the linage specific differentiation of pluripotent or multipotent stem cells, which can include, but is not limited to, human embryonic stem cells (hESC), human induced pluripotent stem cells (hiPSC), somatic stem cells, cancer stem cells, or any other cell capable of lineage specific differentiation. Specifically described are methods to direct the lineage specific differentiation of hESC and/or hiPSC to nociceptors (i.e. nociceptor cells) using novel culture conditions. The nociceptors made using the methods of the present invention are further contemplated for various uses including, but limited to, use in in vitro drug discovery assays, pain research, and as a therapeutic to reverse disease of, or damage to, the peripheral nervous system (PNS). Further, compositions and methods are provided for producing melanocytes from human pluripotent stem cells for use in disease modeling.

35 Claims, 14 Drawing Sheets

(56) References Cited

OTHER PUBLICATIONS

Dovey, et al., "Functional Gamma-Secretase Inhibitors Reduce Beta-Amyloid Peptide Levels in Brain," *J Neurochem.*, 76(1):173-181 (2001).
Ebendal, et al., "Bone Morphogenetic Proteins and Their Receptors: Potential Functions in the Brain," *Journal of Neuroscience, Research*, 51(2):139-146 (1998).
Elkabetz, et al., "Human ES Cell-Derived Neural Rosettes Reveal a Functionally Distinct Early Neural Stem Cell Stage," *Genes Dev.*, 22(2):152-165 (2008).
Elkabetz, et al., "Human ES Cell-Derived Neural Rosettes Reveal a Functionally Distinct Early Neural Stem Cell Stage," *Genes Dev.*, 22(2):152-165 (2008) Erratum (2008).
Fang, et al., "Electrophysiological Differences Between Nociceptive and Non-Nociceptive Dorsal Root Ganglion Neurones in the Rat In Vivo," *The Journal of Physiology*, 565(3):927-943 (2005).
Fasano, et al., "Efficient Derivation of Functional Floor Plate Tissue From Human Embryonic Stem Cells," *Cell Stem Cell*, 6(4):336-347 (2010).
George, et al., "Nociceptive Sensory Neurons Derive From Contralaterally Migrating, Fate-Restricted Neural Crest Cells," *Nat Neurosci.*, 10(10):1287-1293 (2007).
Gerdes, et al., "Production of a Mouse Monoclonal Antibody Reactive With a Human Nuclear Antigen Associated With Cell Proliferation," *Int J Cancer*, 31(1):13-20 (1983).
Gerrero, et al., "Bm-3.0: A POU-Domain Protein Expressex in the Sensory, Immune, and Endocrine Systems That Functions on Elements Distinct From Known Octamer Motifs," *PNAS USA*, 90(22):10841-10845 (1993).
Groppe, et al., "Structural Basis of BMP Signalling Inhibition by the Cystine Knot Protein Noggin," *Nature*, 420(6016):636-642 (2002).
Hendzel, et al., "Mitosis-Specific Phosphorylation of Histone H3 Initiates Primarily Within Pericentromeric Heterochromatin During G2 and Spreads in an Ordered Fashion Coincident With Miotic Chromosome Condensation," *Chromosoma.*, 106(6):348-360 (1997).
Hogan, "Bone Morphogenetic Proteins: Multifuctional Regulators of Vertebrate Development," *Genes Dev.*, 10(13):1580-1594 (1996).
Joannides, et al., "Automated Mechanical Passaging: A Novel and Efficient Method for Human Embryonic Stem Cell Development," *Stem Cells*, 24(2):230-235 (2006).
Kikuchi, et al., "Multiplicity of the Interactions of Wnt Proteins and Their Receptors," *Cell Signal*, 19(4):659-671 (2007).
Kim, et al., "Robust Enhancement of Neural Differentiation From Human ES and iPS Cells Regardless of Their Innate Difference in Differentiation Propensity," *Stem Cell Reviews and Reports*, 6(2):270-281 (2010).
Kitao, et al., "Neurogenesis of Subpopulation of Rat Lumbar Dorsal Root Ganglion Neurons Including Neurons Projecting to the Dorsal Column Nuclei," *The Journal of Comparative Neurology*, 371(2), 249-257 (1996).
Kodama, et al., "Neurogenic Potential of Progenitors Derived from Human Circulating CD14+ Monocytes," *Immunol Cell Biol.*, 84(2):209-217 (2006).
Lee, et al., "Isolation and Directed Differentiation of Neural Crest Stem Cells Derived From Human Embryonic Stem Cells," *Nat Biotechnol.*, 25(12):1468-1475 (2007).
Lee, et al., "Instructive Role of Wnt/β-Catenin in Sensory Fate Specification in Neural Crest Stem Cells," *Science*, 303(5660):1020-1023 (2004).
Lee, et al., "The Expression and Posttranslational Modification of a Neuron-Specific B-Tubulin Isotype During Chick Embryogenesis," *Cell Motility and the Cytoskeleton*, 17(2):118-132 (1990).
Li, et al., "Specification of Motoneurons From Human Embryonic Stem Cells," *Nat Biotechnol.*, 23(2):215-221 (2005).
Ma, et al., "Neurogenin1 and Neurogenin2 Control Two Distinct Waves of Neurogenesis in Developing Dorsal Root Ganglia," *Genes Dev.*, 13(13):1717-1728 (1999).

Marmigere and Ernfors, "Specification and Connectivity of Neuronal Subtypes in the Sensory Lineage," *Nat Rev Neurosci.*, 8(2):114-127 (2007).
Mehler, et al., "Bone Morphogenetic Proteins in the Nervous System," *Trends Neurosci.*, 20(7), 309-317 (1997).
Papapetrou, et al., "Stoichiometric and Temporal Requirements of Oct4, Sox2, K1f4, and c-Myc Expression for Efficient Human Ipsc Induction and Differentiation," *PNAS USA*, 106(31):12759-12764 (2009).
Paterson, et al., "Preclinical Studies of Fibroblast Growth Factor Receptor 3 as a Therapeutic Target in Multiple Myeloma," *Br J Haematol.*, 124(5), 595-603 (2004).
Perrier, et al., "Derivation of Midbrain Dopamine Neurons From Human Embryonic Stem Cells," *PNAS USA*, 101(34):12543-12548 (2004).
Perrier, et al., "Derivation of Midbrain Dopamine Neurons From Human Embryonic Stem Cells," *PNAS USA*, 101(34):12543-12548 Supplemental Data (2004).
Placantonakis, et al., "BAC Transgenesis in Human Embryonic Stem Cells as a Novel Tool to Define the Human Neural Lineage," *Stem Cells*, 27(3):521-532 (2009).
Saha and Jaenisch, "Technical Challenges in Using Human Induced Pluripotent Stem Cells to Model Disease," *Cell Stem Cell*, 5(6):584-595 (2009).
Schlosser and Northcutt, "Development of Neurogenic Placodes in *Xenopus laevis*," *The Journal of Comparative Neurology*, 418(2):21-146 (2000).
Schlosser, et al., "Induction and Specification of Cranial Placodes," *Dev Biol.*, 294(2):303-351 (2006) A: pp. 303-327.
Schlosser, et al., "Induction and Specification of Cranial Placodes," *Dev Biol.*, 294(2):303-351 (2006) B: pp. 328-351.
Sun, et al., "Design, Synthesis, and Evaluations of Substituted 3-[(3- or 4-Carboxyethylpyrrol-2-Yl)Methylidenyl]Indolin-2-Ones as Inhibitors of VEGF, FGF, and PDGF Receptor Tyrosine Kinases," *J Med Chem.*, 42(25):5120-5130 (1999).
Sun, et al., "A Central Role for Islet1 in Sensory Neuron Development Linking Sensory and Spinal Gene Regulatory Programs," *Nat Neurosci.*, 11(11):1283-1293 (2008).
Takahashi and Yamanaka, "Induction of Pluripotent Stem Cells From Mouse Embryonic and Adult Fibroblast Cultures by Difined Factors," *Cell*, 126(4):663-676 (2006).
Tanaka, et al., "FGF-Induced Vesicular Release of Sonic Hedgehog and Retinoic Acid in Leftward Nodal Flow is Critical for Left-Right Determination," *Nature*, 435(7039):172-177 (2005).
Theos, et al., "The Silver Locus Product Pmel17/Gp100/Silv/Me20: Controversial in Name and in Function," *Pigment Cell Res.*, 18(5):322-336 (2005).
Tomishima, et al., "Production of Green Fluorescent Protein Transgenic Embryonic Stem Cells Using the GENSAT Bacterial Artificial Chromosome Library," *Stem Cells*, 25(1):39-45 (2007).
Vallier, et al., "Nodal Inhibits Differentiation of Human Embryonic Stem Cells Along the Neuroectodermal Default Pathway," *Dev Biol.*, 275(2):403-421 (2004).
Vierbuchen, et al., "Direct Conversion of Fibroblasts to Functional Neurons by Defined Factors," *Nature*, 463(7284):1035-1041 (2010).
Wang, et al., "Noggin and bFGF Cooperate to Maintain the Pluripotency of Human Embryonic Stem Cells in the Absence of Feeder Layers," *Biochem Biophys Res Commun.*, 330(3):934-942 (2005).
Woolf and Ma, "Nociceptors—Noxious Stimulus Detectors," *Neuron*, 55(3):353-364 (2007).
Xu, et al., "Basic FGF and Suppression of BMP Signaling Sustain Undifferentiated Proliferation of Human ES Cells," *Nat Methods*, 2(3):185-190 (2005).
Yamashita, et al., "Bone Morphogenetic Protein Receptors," *Bone*, 19(6):569-574 (1996).
Yan, et al., "Directed Differentiation of Dopaminergic Neuronal Subtypes from Human Embryonic Stem Cells," *Stem Cells*, 23(6):781-790 (2005).
Yu, et al., "BMP Type I Receptor Inhibition Reduces Heterotopic [corrected] Ossification," *Nat Med.*, 14(12):1363-1369 (2008).

(56) References Cited

OTHER PUBLICATIONS

Zhang and Zhang, "Differentiation of Neural Precursors and Dopaminergic Neurons from Human Embryonic Stem Cells," *Methods Mol Biol.*, 584:355-366 (2010).

Zhou, et al., "High-Efficiency Induction of Neural Conversion in Human ESCs and Human Induced Pluripotent Stem Cells With a Single Chemical Inhibitor of Transforming Growth Factor Beta Superfamily Receptors," *Stem Cells*, 28(10):1741-1750 (2010).

Zhu, et al., "Functional *Smoothened* is Required for Expression of *Gli3* in Colorectal Carcinoma Cells," *Cancer Letters*, 207(2):205-214 (2004).

Zietlow, et al., "The Survival of Neural Precursor Cell Grafts is Influenced by In Vitro Expansion," *Journal of Anatomy*, 207(3):227-240 (2005).

ISR PCT/US2011/037179.

Raymon, et al., "Immortalized Human Dorsal Root Ganglion Cells Differentiate into Neurons with Nociceptive Properties," *The Journal of Neuroscience*, 19(13):5420-5428 (1999).

Chambers, et al., "Combined small-molecule inhibition accelerates developmental timing and converts human pluripotent stem cells into nociceptors", *Nature Biotechnology* 30(7):715-720 (2012).

Chambers, et al., "Dual-SMAD Inhibition/WNT Activation-Based Methods to Induce Neural Crest and Derivatives from Human Pluripotent Stem Cells", *Methods in Molecular Biology* (2013) DOI 10.1007/7651_2013_59.

Chen et al., "Immortalization and characterization of a nociceptive dorsal root ganglion sensory neuronal line." J Peripher Nery Syst. Jun. 2007; 12(2):121-30.

Crawford, et al., "The Notch Response Inhibitor DAPT Enhances Neuronal Differentiation in Embryonic Stem Cell-Derived Embryoid Bodies Independently of Sonic Hedgehog Signaling", *Developmental Dynamics* 236:886-892 (2007).

Kriks, et al., "Dopamine neurons derived from human ES cells efficiently engraft in animal models of Parkinson's disease", *Nature* 480(7378):547-551 (Dec. 2011).

Li, et al., "Rapid induction and long-term self-renewal of primitive neural precursors from human embryonic stem cells by small molecule inhibitors", *Proc. Natl. Acad. Sci. USA* 108:8299-8304 (2011).

\* cited by examiner

METHOD OF NOCICEPTOR DIFFERENTIATION OF HUMAN EMBRYONIC STEM CELLS AND USES THEREOF

CROSS-REFERENCE TO RELATED APPLICATIONS

This application is a national phase application filed under 35 U.S.C. §371 as a national stage of International Application Serial No PCT/US2011/037179, filed May 19, 2011, which claims priority of U.S. Provisional Application Ser. No. 61/396,257, filed May 25, 2010, the contents of each of which are incorporated by reference in their entirety, and to each of which priority is claimed.

FIELD OF THE INVENTION

The present invention relates to the field of stem cell biology, in particular the linage specific differentiation of pluripotent or multipotent stem cells, which can include, but is not limited to, human embryonic stem cells (hESC), human induced pluripotent stem cells (hiPSC), somatic stem cells, cancer stem cells, or any other cell capable of lineage specific differentiation. Specifically described are methods to direct the lineage specific differentiation of hESC and/or hiPSC to nociceptors (i.e. nociceptor cells) using novel culture conditions. The nociceptors made using the methods of the present invention are further contemplated for various uses including, but limited to, use in in vitro drug discovery assays, pain research, and as a therapeutic to reverse disease of, or damage to, the peripheral nervous system (PNS). Further, compositions and methods are provided for producing melanocytes from human pluripotent stem cells for use in disease modeling.

BACKGROUND OF THE INVENTION

Embryonic and somatic stem cells have the ability to differentiate into any cell type; they are therefore uniquely suited for cell replacement therapies for diseases which ravish, or damage/injury to, a defined cell population. Beyond their direct therapeutic value, lineage specific differentiated stem cells are also valuable research tools for a variety of purposes including in vitro screening assays to identify, confirm, test for specification or delivery of therapeutic molecules to treat lineage specific disease, further elucidation of the complex mechanisms of cell lineage specification and differentiation, and identifying critical biochemical differences between normal and diseased or damaged states which can be further contemplated for use as diagnostic or prognostic markers.

The power of embryonic and somatic stem cells as therapeutics and model systems for neurodegenerative diseases has been well explored. However, much of the research and technological developments relating to directed differentiation of embryonic and somatic stem cells has taken place in the field of diseases of the central nervous system (CNS), such as Huntington's, Alzheimer's, Parkinson's, and multiple sclerosis. There is a current lack of knowledge relating to the directed differentiation of embryonic and somatic stem cells toward lineages of the peripheral nervous system (PNS). The PNS is comprised of the somatic nervous system, which coordinates muscular-skeletal control and sensation of external stimuli, and the autonomic nervous system, which regulates inner organ function such as heartbeat and respiration. There are multiple diseases of the PNS including Charcot-Marie-Tooth disease, Gillian Bane Syndrome, and Hirschsprung's disease. Diseases of peripheral sensory neurons of the PNS are of particular societal burden because they result in severe pain or failure to respond to noxious stimuli causing injury and include diseases such as Familial Dysautonomia, congenital insensitivity to pain, diabetic neuropathies, and damage due to infections of Varicella or herpes zoster.

Understanding the pathology of peripheral sensory neuron diseases, as well as development of treatment modalities, is hindered by the difficulties in obtaining human peripheral sensory neurons; current methods are limited to manual isolation from 3-5 week old human embryos or rare surgical procedures. The directed differentiation of embryonic stem cells or somatic stem cells into specified peripheral sensory neurons, in particular nociceptors which are the pain sensing peripheral sensory neurons, would be an ideal reproducible source of such cells for both research and therapeutic application. Recent attempts to produce peripheral sensory neurons from neuronal intermediates derived from embryonic stem cells have been made. However, these techniques are limited by the need for a neuronal intermediate, co-culture with murine stromal cells, length of time to derive such peripheral sensory neurons, low yield, impure populations of cells containing mixed neuronal types, limited survival and poor characterization of PNS generated neurons.

Therefore there is a need in the art for a method to produce peripheral sensory neurons, in particular nociceptors, directly from embryonic or somatic stem cells without the use of contaminating murine stromal cells with increased purity and yield.

SUMMARY OF INVENTION

The present invention relates to the field of stem cell biology, in particular the linage specific differentiation of pluripotent or multipotent stem cells, which can include, but is not limited to, human embryonic stem cells (hESC), human induced pluripotent stem cells (hiPSC), somatic stem cells, cancer stem cells, or any other cell capable of lineage specific differentiation. Specifically described are methods to direct the lineage specific differentiation of hESC and/or hiPSC to nociceptors (i.e. nociceptor cells) using novel culture conditions. The nociceptors made using the methods of the present invention are further contemplated for various uses including, but limited to, use in in vitro drug discovery assays, pain research, and as a therapeutic to reverse disease of, or damage to, the peripheral nervous system (PNS). Further, compositions and methods are provided for producing melanocytes from human pluripotent stem cells for use in disease modeling.

It is an object of the present invention to overcome the limitations and/or mitigate the deficiencies in the field. In one embodiment, the present invention provides a method of producing nociceptors comprising i) obtaining stem cells (for example, hESCs, hiPSCs, somatic stem cells, cancer stem cells, human or mammalian pluripotent cells, etc.); ii) culturing said stem cell under conditions that inhibit dual SMAD signaling; and iii) further culturing said cells under conditions which inhibit FGF and Notch signaling and activate Wnt signaling. As used herein, the term "inhibit" or "block" means a reduction in the level of activity of a particular signaling pathway of a cell upon treatment with a compound (i.e. an inhibitor) compared to the activity of said signaling pathway of a cell that is left untreated with such compound or treated with a control. As used herein, the term "activate" means an increase in the level of activity of a particular signaling pathway of a cell upon treatment with a compound (i.e. an activator) compared to the activity of said signaling pathway of a cell that is left untreated with such compound or treated with a control. Any level of inhibition or activation of a particular signaling pathway is considered an embodiment of the invention if such inhibition or activation results in the directed differentiation of a stem cell. In one embodiment, the methods for culture include conditions for a feeder-free system. In one embodiment, the stem cells are cultured in a monolayer. In a preferred embodiment the method for culture contemplates the use of media that contains the compounds SB431542, LDN1933189, SU5402, CHIR99021, and DAPT. In one embodiment, the differentiated cell is at least 10% up to 100% of the population of the cultured cells. In one embodiment, the differentiated cell expresses one or more markers from the group comprising ISL1, BRN3A, RET, RUNX1, and NTRK1. In one embodiment, expression of said marker(s) is expressed in at least 10% up to 100% of the population of the cultured cells. In a preferred embodiment, the differentiated cell is a nociceptor. In a preferred embodiment, the stem cell is a hESC or a hiPSC.

In one embodiment, the present invention provides a kit comprising i) a first inhibitor, or combination of inhibitors, that blocks both SMAD signaling and TGFβ/Activin-Nodal signaling; ii) a second inhibitor that blocks FGF signaling; iii) a third inhibitor that blocks Notch signaling; and iv) an activator of Wnt signaling. In one embodiment, the first inhibitor(s) is/are selected from the group comprising LDN193189 and SB431542, a combination thereof and mixture thereof. In one embodiment, the second inhibitor comprises SU5402 and derivatives thereof. In one embodiment, the third inhibitor comprises of DAPT and derivatives thereof. In one embodiment, an activator comprises CHIR99021 and derivatives thereof. In one embodiment, the kit further comprises a human stem cell. In one embodiment, the kit further provides instructions to practice the present invention.

In one embodiment, the invention provides a kit comprising i) a first inhibitor, or combination of inhibitors, that blocks both SMAD signaling and TGFβ/Activin-Nodal signaling; ii) a second inhibitor that blocks FGF signaling; iii) a third inhibitor that blocks Notch signaling; and iv) an activator of Wnt signaling. In one embodiment, said first inhibitor(s) is selected from the group comprising SB431542, LDN193189, combination thereof and mixture thereof. In one embodiment, said second inhibitor comprises SU5402 and derivatives thereof. In one embodiment, said third inhibitor comprises DAPT and derivatives thereof. In one embodiment, said activator comprises CHIR99021 and derivatives thereof. In one embodiment, said kit further comprises instructions. In one embodiment, said kit further comprises a human stem cell. In one embodiment, said human stem cell is a human embryonic stem cell. In one embodiment, said human stem cell is a human induced pluripotent stem cell.

The present invention further contemplates methods for assessing the peripheral sensory neuronal subtype of the differentiated stem cells. Certain embodiments of this method can utilize microscopic analysis, functional assays, measurement of expression or downregulation of markers associated with particular lineages. In a preferred embodiment, the method comprises of measuring markers associated with nociceptor specification selected from the group comprising ISL1, BRN3A, RET, RUNX1, and NTRK1.

In one embodiment, the invention provides a method for inducing directed differentiation of a stem cell, comprising a) providing: i) a cell culture comprising human stem cells ii) a first inhibitor, or combination of inhibitors, that blocks both SMAD signaling and TGFβ/Activin-Nodal signaling; iii) a second inhibitor that blocks FGF signaling; iv) a third inhibitor that blocks Notch signaling; and v) an activator of Wnt signaling, b) contacting said stem cell with said first a first inhibitor, or combination of inhibitors, that blocks both SMAD signaling and TGFβ/Activin-Nodal signaling for 0-48 H (more typically 1-48 hours) in vitro, and c) further contacting said stem cell with a second inhibitor that blocks FGF signaling; a third inhibitor that blocks Notch signaling; and an activator of Wnt signaling for up to an additional 192 hours (or even up to 240 hours). In one embodiment, said first inhibitor(s) is selected from the group comprising SB431542, LDN193189, combination thereof and mixture thereof. In one embodiment, said second inhibitor comprises SU5402 and derivatives thereof. In one embodiment, said third inhibitor comprises DAPT and derivatives thereof. In one embodiment, said activator comprises CHIR99021 and derivatives thereof. In one embodiment, said stem cell is a human embryonic stem cell. In one embodiment, said stem cell is a human induced pluripotent stem cell. In one embodiment, said differentiated cell is a neuronal cell. In one embodiment, said neuronal cell is a nociceptor. In one embodiment, said differentiated cell expresses one or marker(s) from the group comprising ISL1, BRN3A, RET, RUNX1, and NTRK1. In one embodiment, said differentiated cell responds to external stimuli.

The present invention further contemplates uses of the nociceptors generated by a method of the present invention. In one embodiment, the nociceptors are used in in vitro assays to identify compounds that can be used as anti-pain therapeutics. In one embodiment, the nociceptors are used to study the function of nociceptors. In one embodiment, the nociceptors are used as an in vivo cell replacement therapy in an animal suffering from, or at risk for, damage or disease of the PNS.

In one embodiment, the invention provides a method of screening biological agents, comprising, a) providing: i) a nociceptor, and ii) a test compound b) contacting said nociceptor with said test compound and measuring activation or inhibition of nociceptor function. In one embodiment, said nociceptor is derived from a human stem cell.

In one embodiment, the invention provides a kit comprising a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling. In one embodiment, said first inhibitor is a small molecule selected from the group consisting of SB431542, derivatives thereof and mixtures thereof. In one embodiment, said second inhibitor is a small molecule selected from the group consisting of LDN193189, derivatives thereof and mixtures thereof. In one embodiment, said third inhibitor is selected from the group consisting of CHIR99021 and derivatives thereof. In one embodiment, said kit further comprises a fourth inhibitor that lowers fibroblast growth factor (FGF) receptor family signaling, wherein said FGF receptor family signaling comprises vascular endothelial growth factor (VEGF) receptors, fibroblast growth factor (FGF) receptors and platelet-derived growth factor (PDGF) tyrosine kinase receptors. In one embodiment, said fourth inhibitor is selected from the group consisting of SU5402 and derivatives thereof. In one embodiment, said kit further comprises a fifth inhibitor capable of lowering Notch signaling. In one embodiment, said fifth inhibitor is selected from the group consisting of N—[N-(3,5-Difluorophenacetyl)-L-alanyl]-S-phenylglycine t-butyl ester (DAPT) and derivatives thereof. In one embodiment, said kit further comprises antibodies used for the detection of expression of protein(s) selected from the group consisting of nestin, OCT4, PAX6, TUJ1, SOX10, NTRK1, ISL1, POU4F1 (BRN3A), NEUROG2, NEUROG1, MAP2, OTX2, DLK1, DKK1, CUZD1, MSX1, ID2, AP2B, ETS1, FOXD3, NGN1, DCX, TUBB3, SYT4, STMN2, INA, GAP43, TAC1, VGLUT2, SLC15A3, and TRPV1. In one embodiment, said kit further comprises PCR primers for the detection of mRNA expression of genes selected from the group consisting of nestin, OCT4, PAX6, TUJ1, SOX10, NTRK1, ISL1, POU4F1 (BRN3A), NEUROG2, NEUROG1, MAP2, OTX2, DLK1, DKK1, CUZD1, MSX1, ID2, AP2B, ETS1, FOXD3, NGN1, DCX, TUBB3, SYT4, STMN2, INA, GAP43, TAC1, VGLUT2, SLC15A3, and TRPV1. In one embodiment, said kit further comprises antibodies used for the detection of expression of protein(s) selected from the group consisting of Protachykinin-1 (TAC1), vesicular glutamate transporter 2 (VGLUT2) and solute carrier family 15, member 3 (SLC15A3). In one embodiment, said kit further comprises PCR primers for the detection of mRNA expression of genes selected from the group consisting of Protachykinin-1 (TAC1), vesicular glutamate transporter 2 (VGLUT2) and solute carrier family 15, member 3 (SLC15A3). In one embodiment, said kit further comprises instructions comprising steps for adding the first and second inhibitor two days before adding the third inhibitor. In one embodiment, said kit further comprises instructions comprising steps for adding the first and second inhibitor two days before adding a combination of said third inhibitor, said fourth inhibitor and said fifth inhibitor. In one embodiment, said kit further comprises instructions comprising steps for daily feedings of said inhibitors in order on Days 0-10. In one embodiment, said kit further comprises instructions comprising steps for making neural stem cell precursors and making nociceptor cells. In one embodiment, said kit further comprises a human stem cell. In one embodiment, said human stem cell is a human embryonic stem cell. In one embodiment, said human stem cell is a human induced pluripotent stem cell. In one embodiment, said human stem cell is a transgenic SOX10::GFP bacterial artificial chromosome (BAC) human puripotent stem cell (hPSC).

In one embodiment, the invention provides a method for inducing directed differentiation of a stem cell, comprising a) providing: i) a cell culture comprising human stem cells; and ii) a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling; b) contacting said stem cell with said first and said second inhibitor for up to 48 (or even up to 96) hours in vitro; and c) further contacting said inhibited stem cell with said third inhibitor for up to an additional 192 hours (or even up to 240 hours) for inducing directed differentiation of a stem cell, wherein said differentiated stem cell is selected from the group consisting of a neural crest stem cell, a neural crest lineage cell and a neuronal lineage cell. In one embodiment, said first inhibitor is a small molecule selected from the group consisting of SB431542, derivatives thereof and mixtures thereof. In one embodiment, said second inhibitor is a small molecule selected from the group consisting of LDN193189, derivatives thereof and mixtures thereof. In one embodiment, said third inhibitor is selected from the group consisting of CHIR99021 and derivatives thereof. In one embodiment, said kit further comprises a fourth inhibitor that lowers fibroblast growth factor (FGF) receptor family signaling, wherein said FGF receptor family signaling comprises vascular endothelial growth factor (VEGF) receptors, fibroblast growth factor (FGF) receptors and platelet-derived growth factor (PDGF) tyrosine kinase receptors. In one embodiment, said fourth inhibitor is selected from the group consisting of SU5402 and derivatives thereof. In one embodiment, said kit further comprises a fifth inhibitor capable of lowering Notch signaling. In one embodiment, said fifth inhibitor is selected from the group consisting of N—[N-(3,5-Difluorophenacetyl)-L-alanyl]-S-phenylglycine t-butyl ester (DAPT) and derivatives thereof. In one embodiment, said kit further comprises a fourth inhibitor and a fifth inhibitor, wherein said fourth inhibitor is selected from the group consisting of SU5402 and derivatives thereof, wherein said fifth inhibitor is selected from the group consisting of N—[N-(3,5-Difluorophenacetyl)-L-alanyl]-S-phenylglycine t-butyl ester (DAPT) and derivatives thereof for directed differentiated of a neuronal lineage cell into a peptidergic nociceptor cell. In one embodiment, said peptidergic nociceptor cell expresses a marker selected from the group consisting of OCT4, DLK1, PAX6, SOX10, POU4F1 (BRN3A), ISL1, NEUROG2, NEUROG1, NTRK1, RET, RUNX1, VGLUT2, TAC1, and TRPV1. In one embodiment, said peptidergic nociceptor cell expresses a marker selected from the group consisting of ISL1, POU4F1 (BRN3A), RET, RUNX1, and NTRK1. In one embodiment, said marker is selected from the group consisting of a protein and a nucleic acid. In one embodiment, said peptidergic nociceptor cell co-expresses Substance P and Calcitonin gene related peptide (CGRP). In one embodiment, said peptidergic nociceptor cell produces an action potential in response to external stimuli, wherein said external stimuli is an electrical current. In one embodiment, said differentiated peptidergic nociceptor cell is present within a highly enriched populations of neurons within 8 to 18 days and more typically 10-15 days after contacting said stem cell with said first and said second inhibitor. In one embodiment, said stem cell is a human embryonic stem cell. In one embodiment, said stem cell is a human induced pluripotent stem cell.

In one embodiment, the invention provides method of screening a biological agent in vitro, comprising, a) providing: i) a nociceptor cell derived in vitro from directed differentiation of a stem cell; and ii) a test compound; and b) contacting said nociceptor cell with said test compound and measuring nociceptor function, wherein said function is measurement of an action potential. In one embodiment, said nociceptor cell is derived from a human stem cell.

In one embodiment, the invention provides a kit for directed differentiation of a melanocyte.

In one embodiment, the invention provides a method for directed differentiation of a melanocyte.

In one embodiment, the invention provides a method for providing melanocyte lineage cell populations.

In one embodiment, the invention provides a method for providing mature melanocyte cell populations.

DEFINITIONS

As used herein, the term "kit" refers to any delivery system for delivering materials. In the context of cell differentiation, a kit may refer to a combination of materials for contacting stem cells, such delivery systems include systems that allow for the storage, transport, or delivery of reaction reagents (e.g., compounds, proteins, detection agents (such as PAX6 antibodies), etc. in the appropriate containers (such as tubes, etc.) and/or supporting materials (e.g., buffers, written instructions for performing cell differentiation, etc.) from one location to another. For example, kits include one or more enclosures (e.g., boxes, or bags, test tubes, Eppendorf tubes, capillary tubes, multiwell plates, and the like) containing relevant reaction reagents for inhibiting signaling pathways, for example, an inhibitor for lowering transforming growth factor beta (TGFβ)/Activin-Nodal signaling, such as SB431542 (or a SB431542 replacement), and the like, an inhibitor for lowering SMAD signaling, LDN-193189 (or a LDN-193189 replacement), and the like, an inhibitor for lowering glycogen synthase kinase 3β (GSK3β), for one example, for repressed signaling of β-catenin, for activation of wingless (Wnt or Wnts) signaling otherwise known as a WNT signaling activator (WNT agonist), such as CHIR99021 (or a CHIR99021 replacement), etc.), and the like, an inhibitor of FGF family receptor signaling, including lowering fibroblast growth factor (FGF) receptor family signaling, wherein said FGF receptor family signaling comprises vascular endothelial growth factor (VEGF) receptors, fibroblast growth factor (FGF) receptors, and platelet-derived growth factor (PDGF) tyrosine kinase receptor signaling, such as SU5402 (or a SU5402 replacement), and the like, an inhibitor of Notch signaling, such as DAPT (or a DAPT replacement), and the like, and/or supporting materials. The reagents in the kit in one embodiment may be in solution, may be frozen, or may be lyophilized. The reagents in the kit in one embodiment may be in individual containers or provided as specific combinations, such as a combination of LSB, 3i, CHIR, Mel reagents, and the like.

As used herein, the term "signaling" in reference to a "signal transduction protein" refers to proteins that are activated or otherwise affected by ligand binding to a membrane receptor protein or some other stimulus. Examples of signal transduction protein include a SMAD, a WNT complex protein, including beta-catnin, NOTCH, transforming growth factor beta (TGFβ), Activin, Nodal and glycogen synthase kinase 3β (GSK3β) proteins. For many cell surface receptors or internal receptor proteins, ligand-receptor interactions are not directly linked to the cell's response. The ligand activated receptor must first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "NOTCH" refers to a signaling pathway represented by at least five ligands, (for example, termed Jagged-1, -2, and Delta-like (Dll)-1, -3, and -4) that bind to one or more of at least four Notch receptors (termed Notch-1, -2, -3, and -4). Notch signaling is initiated by a receptor-ligand interaction resulting in at least one proteolytic cleavage by TACE (TNF-alpha-converting enzyme) and/or a gamma-secretase/presenilin complex. This proteolytic cleavage results in the release of an intracellular domain protein ($N^{IC}$, the functionally active form of Notch), which translocates to the nucleus and binds CBF-1 (also termed CSL or RBP-Jkappa), a DNA-binding protein. binding of $N^{IC}$ to CBF-1 displaces the repressor complex and recruits nuclear coactivators such as MAML1 and histone acetyltransferases converting CBF-1 into a transcriptional activator. CBF-1/Notch interactions result in the expression of various target genes including Hes (Hairy/Enhancer of Split), Hey (Hairy/Enhancer of Split related with YRPW (also known as HesR, HRT, HERP, CHF, and gridlock)), NF-kappaB, and PPAR families of transcription factors, and cell cycle regulators such as $p21^{CIP1/WAF1}$ and cyclin D, as one example. Hes (including Hes-1) and Hey (including Hey1 and Hey2) family members are examples of transcription factors that are direct downstream targets of Notch activation. Given the complexity of the Notch signaling pathway, it is understandably difficult to predict the outcome of Notch activation or inhibition. Not only are there multiple Notch receptors and ligands (each with a unique expression pattern), but the large number of target genes and potential crosstalk between Notch and other signaling cascades further complicate the system.

As used herein, the term "signals" refer to internal and external factors that control changes in cell structure and function. They are chemical or physical in nature.

As used herein, the term "ligand" refers to molecules and proteins that bind to receptors (R), examples include but are not limited to transforming growth factor-beta, activins, nodal, bone morphogenic proteins (BMPs), etc.

As used herein, the term "inhibitor" in reference to inhibiting a signaling molecule or a signaling molecule's pathway a "signaling inhibitor", such as an inhibitor of SMAD signaling, refers to a compound or molecule (e.g., small molecule, peptide, peptidomimetic, natural compound, siRNA, anti sense nucleic acid, aptamer, or antibody) that interferes with (i.e. reduces or suppresses or eliminates or blocks) the signaling function of the molecule or pathway. In other words, an inhibitor is any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g. Within the extracellular domain, examples of a signaling molecule and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFb signaling molecules. Antibodies that block activins, nodal, TGFb, and BMPs are contemplated for use to neutralize extracellular activators of SMAD signaling, and the like). Thus in one embodiment, an inhibitor of the present inventions induces (changes) or alters differentiation from a default to a non-default cell type, for example, one of the methods of the present inventions comprising at least 3 inhibitors that produced a non-default neural progenitor cell. In a preferred embodiment, an inhibitor of the present inventions "alters" or "lowers" or "blocks" default signaling in order to direct cellular differentiation towards a nondefault cell type, such as described herein for producing nociceptor cells of the present inventions. Thus, an inhibitor of the present inventions is a natural compound or small molecule for increased or decreased signal molecule activity that assists in producing nociceptor cells of the present inventions. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. In some cases, an inhibitor is referred to as a "direct inhibitor" which refers to inhibiting a signaling target or a signaling target pathway by actually contacting the signaling target; for example, a direct inhibitor of a gamma secretase is a DAPT molecule that binds to the gamma secretase protein. Exemplary direct inhibitors include but are not limited to: lidocaine, myricitrin, chronic capsaicin, camphor, amiloride, capsazepine, linopirdine, and most local anesthetics that block general nerve function.

As used herein, the term "extracellular signaling influences" refers to the effect that extracellular signaling molecules (e.g., test agents such as small molecules described herein, pharmaceutical agents, ligands to a receptor, cytokines, chemokines, soluble factors, adhesion molecules, or other signaling molecules) have on a cell (e.g., a eukaryotic cell). In some embodiments, extracellular signaling reduces signaling activity, such as SMAD activity, alters SMAD activation kinetics, or alters SMAD target gene expression pattern.

As used herein, the term "Sma Mothers Against Decapentaplegic" or "Small Mothers Against Decapentaplegic" or "SMAD" refers to a signaling molecule.

As used herein, the term "activator" "activating" refers to compounds for activating molecules resulting in directed differentiation of cells of the present inventions. Exemplary activators include but are not limited to: noxious heat/cold, mechanical stimulation, chemical stimuli (menthol, piperine, acute capsaicin, cinnamaldehyde, bradykinin, ATP, prostaglandins, inflammatory cytokines, acidic saline, fibroblast growth factor (FGF), etc).

As used herein, the term "LSB" refers to a combination of two compounds LDN-193189 and SB431542 capable of lowering or blocking signaling consisting of transforming growth factor beta (TGFβ)/Activin-Nodal signaling and Small Mothers Against Decapentaplegic (SMAD) signaling in a cell.

As used herein, the term "SB431542" refers to a molecule capable of lowering or blocking transforming growth factor beta (TGFβ)/Activin-Nodal signaling with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

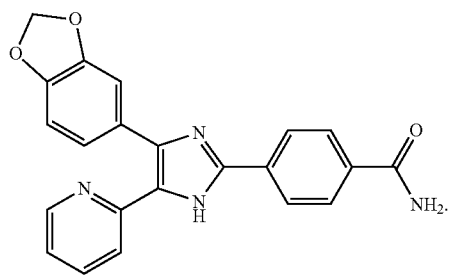 [SMILES: NC(=O)c1ccc(-c2nc(-c3ccc4c(c3)OCO4)c(-c3ccccn3)[nH]2)cc1]

As used herein, the term "LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$. LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

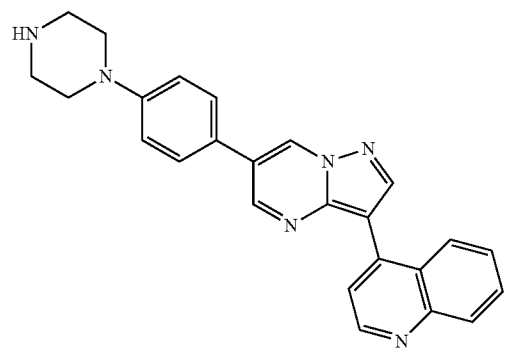 [SMILES: c1ccc2c(-c3cnn4cc(-c5ccc(N6CCNCC6)cc5)cnc34)ccnc2c1]

As used herein, the term "Dorsomorphin" refers to a molecule with a number CAS 866405-64-3, a molecular formula $C_{24}H_{25}N_5O$ and a name of 6-[4-[2-(1-Piperidinyl)ethoxy]phenyl]-3-(4-pyridinyl)-pyrazolo[1,5-a]pyrimidine dihydrochloride, for example, see structure below.

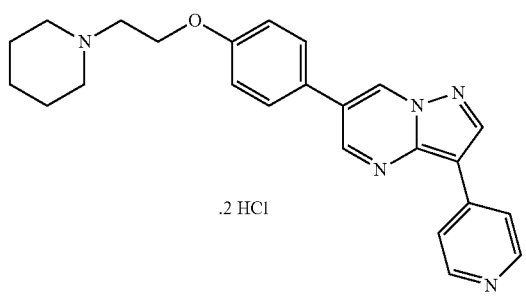 [SMILES: c1cc(-c2cnn3cc(-c4ccc(OCCN5CCCCC5)cc4)cnc23)ccn1]

As used herein, the term "LSB/C" or "LSB-C" refers to a combination of two compounds, such as LDN-193189 and SB431542, which are capable of combined lowering or blocking of signaling consisting of transforming growth factor beta (TGFβ)/Activin-Nodal signaling and Small Mothers Against Decapentaplegic (SMAD) signaling of a cell, in addition to a glycogen synthase kinase 3β inhibitor that acts as a WNT agonist, for example, CHIR99021.

As used herein, the term "glycogen synthase kinase 3β inhibitor" or "GSK3β inhibitor" refers to a compound that inhibits a glycogen synthase kinase 3β enzyme, for example, see, Doble, et al., J Cell Sci. 2003; 116:1175-1186, herein incorporated by reference. For the purposes of the present inventions, a GSK3β inhibitor is capable of activating a WNT signalling pathway, see, for example, Cadigan, et al., J Cell Sci. 2006; 119:395-402; Kikuchi, et al., Cell Signalling. 2007; 19:659-671, herein incorporated by reference.

As used herein, the term "CHIR99021" or "aminopyrimidine" or "3-[3-(2-Carboxyethyl)-4-methylpyrrol-2-methylidenyl]-2-indolinone" refers to IUPAC name 6-(2-(4-(2,4-dichlorophenyl)-5-(4-methyl-1H-imidazol-2-yl)pyrimidin-2-ylamino)ethylamino)nicotinonitrile, CT99021 is one example of a small-molecule chemical inhibitor of glycogen synthase kinase 3β (GSK3β)/activating a WNT signalling pathway, and is highly selective, showing nearly thousand-fold selectivity against a panel of related and unrelated kinases, with an $IC_{50}=6.7$ nM against human GSK3β and nanomolar $IC_{50}$ values against rodent GSK3β homologs.

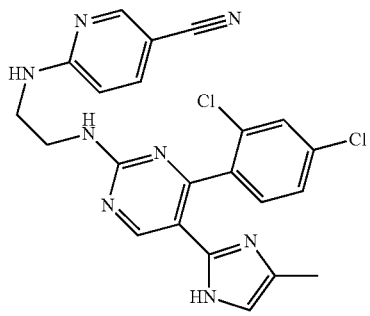 [SMILES: Cc1c[nH]c(-c2cnc(NCCNc3ccc(C#N)cn3)nc2-c2ccc(Cl)cc2Cl)n1]

As used herein, the term "the three inhibitors" or "3i" refers to a combination of three small molecules CHIR99021, SU5402, and DAPT. In other embodiments, the three inhibitors refer to a combination of three compounds (i.e. small molecules) capable of combined inhibition of glycogen synthase kinase 3β (GSK3β)/activator of WNT signaling (i.e. WNT agonist), a NOTCH signaling inhibitor, i.e. a γ-secretase inhibitor capable of lowering NOTCH signaling and fibroblast growth factor receptor (i.e. an indolinone derivative is an example of a fibroblast growth factor receptor inhibitor).

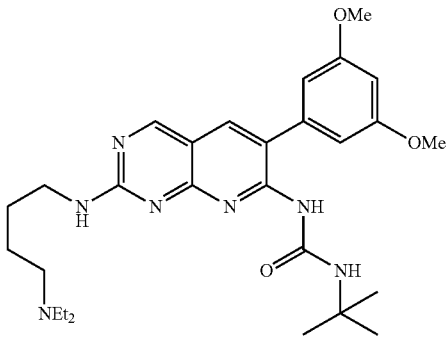

As used herein, the term "Notch inhibitor" or "Notch signaling inhibitor" refers to any compound that has the capability of inhibiting Notch activation, such as DAPT, a γ-secretase inhibitor (GSI), for example, a tripeptide aldehyde inhibitor, a γ-secretase inhibitor XII, and a peptidomimetic inhibitor (LY-411,575).

As used herein, the term "gamma secretase inhibitor" or "GSI" refer to a novel class of agents which prevent the generation of the active domain of a Notch molecules resulting in suppressing downstream Notch signaling.

As used herein, the term "γ-secretase inhibitor" refers to a compound that has the capability of inhibiting γ-secretase, a multi-subunit transmembrane protease. One example of a target (i.e. substrate) for a γ-secretase, for example, is Notch signaling, other γ-secretase substrates include low-density lipoprotein (LDL) receptor-related protein, E-cadherin and ErbB-4. A γ-secretase inhibitor, such as DAPT, γ-secretase inhibitor XII, will therefore block the proteolysis of such γ-secretase substrate(s) including NOTCH.

As used herein, the term "DAPT" refers to one example of a γ-secretase inhibitor that inhibits NOTCH which is described as a dipeptidic γ-secretase-specific inhibitor otherwise known as N-[(3,5-Difluorophenyl)acetyl]-L-alanyl-2-phenyl]glycine-1,1-dimethyl ethyl ester; LY-374973, N—[N-(3,5-Difluorophenacetyl)-L-alanyl]-S-phenylglycine t-butyl ester; N—[N-(3,5-difluorophenacetyl)-L-alanyl]-S-phenylglycine t-butyl ester; with a chemical formula of $C_{23}H_{26}F_2N_2O_4$.

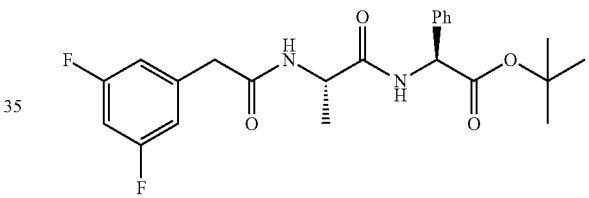

One example of a DAPT derivative is DAP-BpB (N—[N-(3,5-difluorophenacetyl)-L-alanyl]-(S)-phenylglycine-4-(4-(8-biotinamido)octylamino)benzoyl)benzyl)methylamide), a photoactivable DAPT derivative.

As used herein, the term "fibroblast growth factor receptor inhibitor" or "FGFR inhibitor" refers to a small molecule such as SU5402, PD 173074, and the like. One example of an FGFR inhibitor is the indolinone derivative SU5402, exemplary structure shown below.

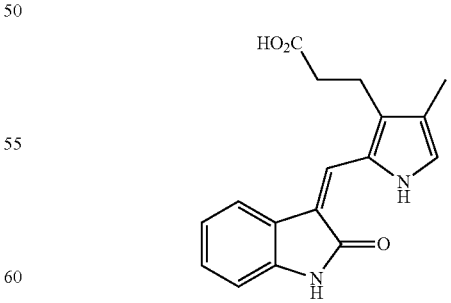

As used herein, the term "SU5402" refers to a small molecule with a chemical formula of $C_{17}H_{16}N_2O_3$ and chemical name: 2-[(1,2-Dihydro-2-oxo-3H-indol-3-ylidene)methyl]-4-methyl-1H-pyrrole-3-propanoic acid (Sun et al (1999) Design, synthesis and evaluations of substituted 3-[(3- or 4-carboxyethylpyrrol-2-yl)methylidenyl]indolin-2-ones as inhibitors of VEGF, FGF and PDGF receptor tyrosine kinases. J. Med. Chem. 42 5120; Paterson et al (2004) Preclinical studies of fibroblast growth factor receptor 3 as a therapeutic target in multiple myeloma. Br. J. Haematol. 124 595; Tanaka et al (2005) FGF-induced vesicular release of sonic hedgehog and retinoic acid in leftward nodal flow is critical for left-right deteimination. Nature 435:172, herein incorporated by reference).

As used herein, the term "derivative" refers to a chemical compound with a similar core structure.

As used herein, the term "WNT" or "wingless" in reference to a ligand refers to a group of secreted proteins (i.e. Intl (integration 1) in humans) capable of interacting with a WNT receptor, such as a receptor in the Frizzled and LRPDerailed/RYK receptor family, As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. For the purposes described herein, a preferred WNT signaling pathway includes mediation by β-catenin, i.e. WNT 4/β-catenin.

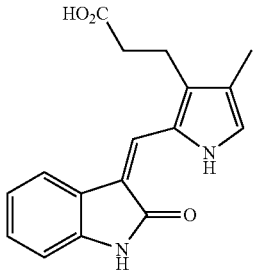 [SMILES: Cc1c[nH]c(/C=C2\C(=O)Nc3ccccc32)c1CCC(=O)O]

As used herein, the term "PD 173074" refers to a small molecule with a chemical name: N-[2-[[4-(Diethylamino)butyl]amino]-6-(3,5-dimethoxyphenyl)pyrido[2,3-d]pyrimidin-7-yl]-N'-(1,1-dimethylethyl)urea. (Barisal et al (2003) Specific inhibitor of FGF receptor signaling: FGF-2-mediated effects on proliferation, differentiation, and MAPK activation are inhibited by PD173074 in oligodendrocyte-lineage cells. J. Neurosci. Res. 74:486, herein incorporated by reference).

As used herein, the term "LSB-3i" or "LSB3i" in reference to a composition and a method of using this composition refers to the combination of LSB molecules (or equivalents) capable of producing neuronal lineage cells and the 3i molecules (or equivalents) capable of directed differentiation of neuronal lineage cells as used in exemplary methods as described herein for directed differentiation of neuronal lineage cells resulting in nociceptors.

As used herein, the term "bone morphogenetic protein" or "BMP" refers to a protein and corresponding gene that is a member of a BMP subfamily, which based upon sequence homology includes GDFs (growth/differentiation factors), in a TGF-beta superfamily of proteins, (see, for example, Yamashita, et al. (1996) Bone 19:569, herein incorporated by reference). Examples of BMPs include, BMP1, BMP2, etc. BMPs/GDFs are grouped into subsets based on amino acid sequence homology. The groupings are suggested to be 1) BMP-2 and BMP-4; 2) BMP-3 and BMP-3b; 3) BMP-5, BMP-6, BMP-7, and BMP-8; 4) BMP-9 and BMP-10; 5) BMP-12, BMP-13, and BMP-14; and 6) BMP-11 and GDF-8 (see, for example, Yamashita, et al. (1996) Bone 19:569, Hogan, (1996) Genes Dev. 10:1580, Mehler, et al. (1997) Trends Neurosci. 20:309, Ebendal, et al. (1998) J. Neurosci. Res. 51: 139, all of which are herein incorporated by reference). TGF Beta superfamily of ligands includes such molecules as Bone morphogenetic proteins (BMPs), Growth and differentiation factors (GDFs), Anti-müllerian hormone (AMH), Activin, Nodal, TGFβ, etc. The TGF beta family include: TGFβ1, TGFβ2, TGFβ3. Like the BMPS, TGF betas are involved in embryogenesis and cell differentiation, but they are also involved in apoptosis, as well as other functions. They bind to TGF-beta receptor type-2 (TGFBR2).

As used herein, the term "bone morphogenetic protein receptor" or a "bone morphogenetic protein receptor type II" or "BMPR2" refers to a serine/threonine kinase receptor that binds to a bone morphogenetic protein.

As used herein, the term "LSB-Mel" refers to a directed differentiation composition and method comprising LSB/C treatment of cells followed by contact with BMP4 and Endothelin-3 (EDN3) for producing melanocyte progenitor cells (melanocyte progenitors), identified and isolated based upon specific markers, i.e. c-kit expression.

As used herein, the term "mature pigmented melanocyte" refers to a pigment cell producing pigmented melanosomes, for example, melanocyte progenitor cells of the present inventions contacted with BMP4 and cAMP.

As used herein, the term "embryonic stem cell" refers to a primitive (undifferentiated) cell that is derived from pre-implantation-stage embryo, capable of dividing without differentiating for a prolonged period in culture, and are known to develop into cells and tissues of the three primary germ layers. A human embryonic stem cell refers to an embryonic stem cell that is human, for example, WA-09.

As used herein, the term "embryonic stem cell line" refers to a population of embryonic stem cells which have been cultured under in vitro conditions that allow proliferation without differentiation for up to days, months to years.

As used herein, the term "stem cell" refers to a cell with the ability to divide for indefinite periods in culture and to give rise to specialized cells. A human stem cell refers to a stem cell that is human.

As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "totipotent" refers to an ability to give rise to all the cell types of the body plus all of the cell types that make up the extraembryonic tissues such as the placenta. (See also Pluripotent and Multipotent).

As used herein, the term "multipotent" refers to an ability to develop into more than one cell type of the body. See also pluripotent and totipotent.

As used herein, the term "pluripotent" refers to an ability to develop into the three developmental germ layers of the organism including endoderm, mesoderm, and ectoderm As used herein, the term "somatic (adult) stem cell" refers to a relatively rare undifferentiated cell found in many organs and differentiated tissues with a limited capacity for both self renewal (in the laboratory) and differentiation. Such cells vary in their differentiation capacity, but it is usually limited to cell types in the organ of origin.

As used herein, the term "somatic cell" refers to any cell in the body other than gametes (egg or sperm); sometimes referred to as "adult" cells.

As used herein, the term "neural lineage cell" refers to a cell that contributes to the nervous system (both central and peripheral) or neural crest cell fates during development or in the adult. The nervous system includes the brain, spinal cord, and peripheral nervous system. Neural crest cell fates include cranial, trunk, vagal, sacral, and cardiac, giving rise to mesectoderm, cranial cartilage, cranial bone, thymus, teeth, melanocytes, iris pigment cells, cranial ganglia, dorsal root ganglia, sympathetic/parasympathetic ganglia, endocrine cells, enteric nervous system, and portions of the heart.

As used herein, the term "induced pluripotent stem cell" or "iPSC" refers to a type of pluripotent stem cell, similar to an embryonic stem cell, formed by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples, C14, C72, and the like.

As used herein, the term "specialized cell" refers to a type of cell that performs a specific function in multicellular organisms. For example, groups of specialized cells, such as neurons, work together to form a system, such as a nervous system.

As used herein, the term "nociceptor" in reference to a cell of the present invention refers to a neuron capable of an action potential and sensing noxious stimulus involved in the perception of pain. Stimuli include, but are not limited to, thermal (heat and cold), mechanical, chemical, and inflammation. Nociceptors are cells expressing specific genes and proteins, such as BRN3A, ISL1, TAC1, VGLUT2, SLC15A3, and comprising a morphology described as two distinct processes with a cell body along an axon-like structure. A "functional nociceptor" in reference to a cell of the present invention refers to a cell resulting from directed differentiation characterized by expression of genes and proteins as described herein, morphology as described herein and capable of producing an action potential such as described herein.

As used herein, the term "peptidergic neuron" in general refers to a neuron identified by expression of a distinct class of ion channels and identified by expression of small peptides such as tachykinins. For instance a peptidergic nociceptor expresses NTRK1 and the tachykinin substance P.

In contrast to a "nonpeptidergic" neuron refers to a neuron that does not express NTRK1 or substance P.

As used herein, the term "neuroectoderm" refers to a cell or cell fate found early in development or during pluripotent stem cell differentiation that can give rise to cells of the neural lineage.

As used herein, the term "markers of cell proliferation" refers to the expression of molecules associated with rapidly cycling cells which are typically not present in mature slowly cycling or noncycling cells, i.e. actively dividing vs. cells with extended cycling times or noncycling cells. Examples of such markers include a Ki67 marker of cell proliferation (Gerdes, et al., *Int J Cancer* 31:13-20 (1983), herein incorporated by reference) and phospho-histone H3 markers of G2/M-phases of mitosis (Hendzel, et al., *Chromosoma* 106:348-360 (1997), herein incorporated by reference).

As used herein, the term "proliferation" refers to an increase in cell number.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as nociceptor cells of the present inventions.

As used herein, the term "directed differentiation" in reference to a stem cell refers to the use of small molecules, growth factor proteins, and other growth conditions to promote the transition of a stem cell from the pluripotent state into a more mature or specialized cell fate (e.g. central nervous system cell, neural cell, nociceptor, etc.).

As used herein, the term "inducing differentiation" in reference to a cell refers to changing the default cell type (genotype and/or phenotype) to a non-default cell type (genotype and/or phenotype). Thus "inducing differentiation in a stem cell" refers to inducing the cell to divide into progeny cells with characteristics that are different from the stem cell, such as genotype (i.e. change in gene expression as determined by genetic analysis such as a microarray) and/or phenotype (i.e. change in expression of a protein, such as PAX6 or a set of proteins, such as HMB45 positive (+) while negative (−) for SOX10.

As used herein, the term "transdifferentiation" refers to a process by which stem or mature cells from one tissue differentiate into cells of another tissue.

As used herein, the term "undifferentiated" refers to a cell that has not yet developed into a specialized cell type.

As used herein, the term "cell differentiation" refers to a pathway by which a less specialized cell (i.e. stem cell) develops or matures to possess a more distinct form and function (for example, an iPSC progressing into a neural crest progenitor to a cell of neuronal lineage to a neural crest cell, to a neuron, to a nociceptor cell to a peptidergic nociceptor or into neuroectoderm to a cell of the central nervous system).

As used herein, the term "differentiation" as used with respect to cells in a differentiating cell system refers to the process by which cells differentiate from one cell type (e.g., a multipotent, totipotent or pluripotent differentiable cell) to another cell type such as a target-differentiated cell.

As used herein, the term "default" or "passive" in reference to a cell differentiation pathway refers to a pathway where a less specialized cell becomes a certain differentiated cell type in culture, when not treating with certain compounds i.e. normal cell cultures conditions. In other words, a default cell results when a cell is not contacted by a molecule capable of changing the differentiated cell type (i.e. a morphogen), for example a Nestin+ TUJ1− cell of the present inventions. In contrast, "non-default" in reference to a cell refers to a differentiated cell type that results in a cell type that is different from a default cell, i.e. a non-default cell is a differentiated cell type resulting from a non-default conditions, such as cell of the present inventions, including a TUJ1+Nestin− neuronal cell, a sensory neuronal cell, a peptidergic nociceptor, a melanocyte, etc. A default cell may also be a default cell after a cell has contact with a morphogen to become a non-default cell without a subsequent morphogenic compound, such as a non-default TUJ1+ Nestin− cell that subsequently becomes a default nonpeptidergic nociceptor.

As used herein, the term "fate" in reference to a cell, such as "cell fate determination" in general refers to a cell with a genetically determined lineage whose progeny cells are capable of becoming a variety of cell types or a few specific cell types depending upon in vivo or in vitro culture conditions. In other words, a cell's predetermined fate is determined by its environment to be destined for a particular differentiation pathway such that a cell becomes one cell type instead of another cell type, for example, a stem cell's progeny cells whose "neural fate" is to become a nerve cell instead of a muscle cell or a skin cell. Typically, a cell's "fate" is irreversible except under highly specific conditions. In another example, a "CNS fate" refers to a cell capable of becoming a cell associated with the central nervous system. Conversely, a cell fated to become a neural cell can be called a "neural progenitor cell."

As used herein, the term "neurite outgrowth" refers to observation of elongated, membrane-enclosed protrusions of cytoplasm from cells.

As used herein, the term "dopamine neuron" or "dopaminergic neuron" in general refers to a cell capable of expressing dopamine. "Midbrain dopamine neurons" or "mDA" refer to presumptive dopamine expressing cells in forebrain structures and dopamine expressing cells in forebrain structures.

As used herein, the term "neural stem cell" refers to a stem cell found in adult neural tissue that can give rise to neurons and glial (supporting) cells. Examples of glial cells include astrocytes and oligodendrocytes.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "cell culture" refers to a growth of cells in vitro in an artificial medium for research or medical treatment.

As used herein, the term "culture medium" refers to a liquid that covers cells in a culture vessel, such as a Petri plate, a multiwell plate, and the like, and contains nutrients to nourish and support the cells. Culture medium may also include growth factors added to produce desired changes in the cells.

As used herein, the term "feeder layer" refers to a cell used in co-culture to maintain pluripotent stem cells. For human embryonic stem cell culture, typical feeder layers include mouse embryonic fibroblasts (MEFs) or human embryonic fibroblasts that have been treated to prevent them from dividing in culture.

As used herein, the term "passage" in reference to a cell culture, refers to the process in which cells are disassociated, washed, and seeded into new culture vessels after a round of cell growth and proliferation. The number of passages a line of cultured cells has gone through is an indication of its age and expected stability.

As used herein, the term "expressing" in relation to a gene or protein refers to making an mRNA or protein which can be observed using assays such as microarray assays, antibody staining assays, and the like.

As used herein, the term "paired box gene 6" or "PAX6" refers to a marker of a nondefault neuroprogenitor cell.

As used herein, the term "TUJ1" or "neuron-specific class III beta-tubulin" in reference to a differentiating cell of the present inventions refers to a marker of early neural human cell differentiation, such as neural progenitor cells, and is found expressed in neurons of the PNS and CNS.

As used herein, the term "nestin" in reference to a differentiating cell of the present inventions refers to an intermediate filament-associated protein that is a marker of neural crest stem cells and CNS neural stem cells.

As used herein, the term "homodimer" in reference to a SMAD molecule refers to at least two molecules of SMAD linked together, such as by disulfide linkages.

As used herein, the term "EDN3" refers to a secreted peptide from the endothelin family of endothelium-derived proteins which binds the cell surface receptor EDNRB commonly found on neural crest derived cell lineages such as the bipotent glial-melanocyte stem cell. One example of a EDN3 amino acid sequence is: endothelin 3 at Accession #NP_000105; Accession PI14138 (EDN3_HUMAN) (SEQ ID NO:1): MEPGLWLLFGLTVTSAAGFVPCSQS-GDAGRRGVSQAPTAARSEGDCEETVAGPGEE TVAG-PGEGTVAPTALQGPSPGSPGQEQAAEGAPEHHRSR-RCTCFTYKDKECVYYCH LDIIWINTPEQTVPYGLSNYRGSFRGKRSAGPLPGN-LQLSHRPHLRCACVGRYDKAC LHFCTQTLDVSSN-SRTAEKTDKEEEGKVEVKDQQSKQALDLHHP-KLMPGSGLALAP STCPRCLFQEGAP.

As used herein, the term "Noggin" refers a secreted homodimeric glycoprotein that binds to and inactivates members of the transforming growth factor-beta (TGF-β) superfamily of signaling proteins, such as bone morphogenetic protein-4 (BMP4).

Noggin is typically a 65 kDa protein expressed in human cells as a glycosylated, disulfide-linked dimer. (Groppe, et al., (2002). Nature 420, 636-642; Xu, et al., (2005) Nat Methods 2, 185-190; Wang, et al., (2005) Biochem Biophys Res Commun 330:934-942). One example of a Noggin amino acid sequence is: Accession # U79163 single amino acid mouse Noggin (SEQ ID NO:2): MERCPSLGVTLY-ALVVVLGLRAAPAGGQHYLHIRPAPSDNLPLVDFTLI-EHPDPIFDP KEKDLNETLLRSLLGGHYDPGF-MATSPPEDRPGGGGGPAGGAEDLAELFTDQLLRQ RPSGAMPSEIKGLEFSEGLAQGKKQRLSKKLR-RKLQMWLWSQTFCPVLYAWNDFTL GSRFWPRYVK-VGSCFSKRSCSVPEGMVCKPSKSVHLTVLRWRCQR-RGGQRCGWIPI QYFTPIISECKCSC.

As used herein, the term "lefty" refers to a novel member of the transforming growth factor beta superfamily that inhibits TGF-beta, including but not limited to LEFTY1, LEFTY2, LEFTYA, etc., also known as "EBAF" or "endometrial bleeding associated factor" or "left-right determination, factor A". A Lefty protein is required for left-right asymmetry determination of organ systems in mammals.

As used herein, the term "activin" refers to a member of the transforming growth factor-beta (TGF-β) superfamily, such as Activin A, Activin B, etc.

As used herein, the term "transforming growth factor beta" or "TGF-β" refers to a cytokine that regulates growth and differentiation of diverse types of cells.

As used herein, the term "nodal" refers to a member of the TGF-β family of signaling molecules. Nodal signaling inhibits differentiation of human embryonic stem cells along the neuroectodermal default pathway (Vallier, et al., Dev. Biol. 275, 403-421.

As used herein, the term "ALK" or "anaplastic lymphoma kinase" or "anaplastic lymphoma receptor tyrosine kinase" or "Ki-1" refers to a membrane associated tyrosine kinase receptor.

As used herein, the term "ALK5" in reference to a type I serine/threonine kinase receptor refers to an anaplastic lymphoma receptor tyrosine kinase 5 receptor that binds to TGF-β1 to function as a TGF-β1 receptor.

As used herein, the term "ALK7" in reference to a type I serine/threonine kinase receptor refers to an anaplastic lymphoma receptor tyrosine kinase 7 receptor that binds to Nodal and Nodal-related proteins to function as a Nodal and Nodal-related protein receptor.

As used herein, the term "contacting" cells with a compound of the present inventions refers to placing the compound in a location that will allow it to touch the cell in order to produce "contacted" cells. The contacting may be accomplished using any suitable method. For example, in one embodiment, contacting is by adding the compound to a tube of cells. Contacting may also be accomplished by adding the compound to a culture of the cells.

As used herein, the term "attached cell" refers to a cell growing in vitro wherein the cell adheres to the bottom or side of the culture vessel, an attached cell may contact the vessel via extracellular matrix molecules and the like and requires the use of an enzyme for detaching this cell from the culture dish/container, i.e. trypsin, dispase, etc. As opposed to a cell in a suspension culture that is not attached and does not require the use of an enzyme for removing cells from the culture vessel.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type. For example, nociceptor cells of the present inventions express one or more markers that distinguish a nociceptor cell from a precursor less differentiated cell, i.e. TUJ1 positive and Nestin negative nociceptor, from a nonnociceptor cell or precursor cell, i.e. TUJ1 negative and Nestin positive cell.

As used herein, the term "positive cell" in relation to a stain refers to a cell that expresses a marker and thus "stains" for that marker in a detectable quantitative and/or qualitative amount above a control or comparative cell. A positive cell may also refer to a cell that stains for a molecule such as Nestin, et cetera.

As used herein, the term "negative cell," refers to a cell absent detectable signal for a marker, such as a cell failing to stain following contacting with a Nestin antibody detection method, et cetera.

As used herein, the term "DAPI" refers to a 4',6-diamidino-2-phenylindole.2HCl fluorescent stain. DAPI fluorescence staining methods are well known, as one of numerous examples, see, DAPI Nucleic Acid Stain, 2006, Molecular Probes, Inc., Eugene, Oreg., 97402, USA.

As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene).

As used herein, the term "GFP" refers to any green fluorescent protein DNA sequence capable of producing a fluorescent protein upon expression in a cell typically use as an indication marker for expression of a target gene. Examples of GFP include GFP sequences isolated from coelenterates, such as the Pacific jellyfish, *Aequoria Victoria*, and synthetic sequence derivatives thereof, such as "eGFP".

The term "sample" is used in its broadest sense. In one sense it can refer to a cell or tissue. In another sense, it is meant to include a specimen or culture obtained from any source and encompass fluids, solids and tissues. Environmental samples include environmental material such as surface matter, soil, water, and industrial samples. These examples are not to be construed as limiting the sample types applicable to the present invention.

The terms "purified," "to purify," "purification," "isolated," "to isolate," "isolation," and grammatical equivalents thereof as used herein, refer to the reduction in the amount of at least one contaminant from a sample. For example, a desired cell type is purified by at least a 10%, preferably by at least 30%, more preferably by at least 50%, yet more preferably by at least 75%, and most preferably by at least 90%, with a corresponding reduction in the amount of undesirable cell types, such as isolated differentiated neuronal cells from normeuronal cells. In other words "purify" and its equivalents, refers to the removal of certain cells (e.g., undesirable cells) from a sample. For example, for providing a purified population of TUJ1+ neuronal cells of the present inventions, TUJ1+Nestin− neuronal cells are purified by removal of contaminating Nestin+ TUJ1− neuronal cells by sorting a mixed cell population into NTRK1+ and NTRK1− cells by flow cytometry, as described herein; neuronal nociceptor cells are also purified or "selected" from non-nociceptor cells (default cells) by using a specified method of cell culture comprising compositions and methods of the present inventions. The removal or selection of non-nociceptor cells results in an increase in the percent of desired nociceptor cells in the sample.

Thus purification of a cell type results in an "enrichment," i.e., an increase in the amount, of the desired cell, i.e. nociceptors in the sample.

The term "naturally occurring" as used herein when applied to an object (such as cell, tissue, etc.) and/or chemical (such as a protein, amino acid sequence, nucleic acid sequence, codon, etc.) means that the object and/or compound are/were found in nature. For example, a naturally occurring cell refers to a cell that is present in an organism that can be isolated from a source in nature, such as an embryonic cell, wherein the cell has not been intentionally modified by man in the laboratory.

As used herein the term, "in vitro" refers to an artificial environment and to processes or reactions that occur within an artificial environment. In vitro environments exemplified, but are not limited to, test tubes and cell cultures.

As used herein the term, "in vivo" refers to the natural environment (e.g., an animal or a cell) and to processes or reactions that occur within a natural environment, such as embryonic development, cell differentiation, neural tube formation, etc.

The term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vivo, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

As used herein, the term "cell" refers to a single cell as well as to a population of (i.e., more than one) cells. The population may be a pure population comprising one cell type, such as a population of neuronal cells or a population of undifferentiated embryonic cells. Alternatively, the population may comprise more than one cell type, for example a mixed cell population. It is not meant to limit the number of cells in a population, for example, a mixed population of cells may comprise at least one differentiated cell. In one embodiment a mixed population may comprise at least one differentiated. In the present inventions, there is no limit on the number of cell types that a cell population may comprise.

As used herein, the term "highly enriched population" refers to a population of cells, such as a population of cells in a culture dish, expressing a marker at a higher percentage or amount than a comparison population, for example, treating a LSB contacted cell culture on day 2 with CHIR/ SU or CHIR/DAPT results in a highly enriched population compare to treatment with SU/DAPT.

The term, "cell biology" or "cellular biology" refers to the study of a live cell, such as anatomy and function of a cell, for example, a cell's physiological properties, structure, organelles, and interactions with their environment, their life cycle, division and death.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific snRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "melanocyte" in reference to a cell of the present inventions in general refers to a cell derived from PSC, including an early melanocyte, expressing a group of markers including Sox10, HMB45, c-kit, essential melanocyte transcription factor MITF-M or MITFM, an isoform of microphthalmia-associated transcription factor (MITF) a member of the basic helix-loop-helix leucine zipper transcription factor family expressed in melanocytes), tyrosinase (TYR), tyrosinase-related protein 1 (TYR-1)-TYR-related protein-2/dopachrome-tautomerase (DCT), etc., containing premelosomes and/or melanosomes, with or without obvious pigment (as observed by eye or by microscopy). Mature melanocytes typically contain pigmented melanosomes, are tyrosinase positive, and express melanocytes proteins such as tyrosinase related protein 1 (TRP1), etc.

As used herein, the term "early melanocyte" or "melanoblast" or "melanocyte precursor" or "melanocyte progenitor" in reference to a cell of the present inventions refers to a cell co-expressing Sox10::GFP and MITF, and c-kit, that is capable of further differentiation into a mature melanocyte. In one embodiment, Sox10::GFP is a marker for presumptive melanocyte precursors. In another embodiment, c-kit is a marker for presumptive melanocyte precursors. In a further embodiment, Sox10::GFP/c-kit double positive cells are presumptive melanocyte precursor cells.

As used herein, the term "HMB45+" in reference to a cell of the present inventions refers to a cell expressing a premelanosomal glycoprotein, i.e. human Pmel17, Theos, et al., Pigment Cell Res. 2005. 18(5):322-36, herein incorporated by reference), such as early (phase) melanocyte (i.e. an immature melanocyte), a cell capable of differentiating into a pigmented cell of the retinal pigment epithelium, mature melanocytes containing immature melanosomes, and the like.

As used herein, the term 'disease modeling' refers to the process of using an experimental organism or in vitro cell cultures to mimic specific signs or symptoms observed in humans as a result of a disorder. In one embodiment, human pluripotent stem cells derived from a person with a genetic mutation resulting in a neurological disorder can be grown and differentiated into neural cells harboring a similar defect observed within the person.

DETAILED DESCRIPTION OF THE INVENTION

Figure 1:
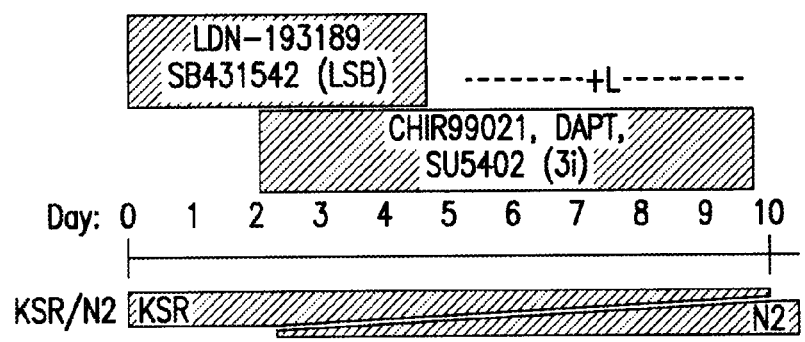
FIG. 1—Exemplary LSB3i Differentiation scheme—A preferred embodiment of the method of the present invention. When dual SMAD inhibition was induced using LDN-193189 and SB431542 (LSB), optimal neuronal differentiation was observed when CHIR99021, SU5402 and DAPT (3i) were added at day two of differentiation. Starting on day 4, N2 media was added in increasing 25% increments on subsequent days replacing KSR. hESC are plated as a single cell monolayer without the use of a stromal feeder layer. For the first five days, combined BMP (exemplified by LDN193189) and TGF/Nodal/Activin (exemplified by SB431542) inhibition (LSB) is used to restrict and promote neural differentiation. Three additional inhibitors (exemplified by CHIR99021, DAPT, SU5402; collectively called 3i) are applied 48 hours after the initial induction. Inclusion or exclusion of LDN193189 from days 5 to 10 does not make a difference in the differentiation. In summary, cells are fed daily, and media is transitioned from KSR to N2 to support the emerging neural cell population. - - - +L - - - represents duplicate cultures wherein LDN was added from days 5 to 10.

The present invention relates to the field of stem cell biology, in particular the linage specific differentiation of pluripotent or multipotent stem cells, which can include, but is not limited to, human embryonic stem cells (hESC), human induced pluripotent stem cells (hiPSC), somatic stem cells, cancer stem cells, or any other cell capable of lineage specific differentiation. Specifically described are methods to direct the lineage specific differentiation of hESC and/or hiPSC to nociceptors (i.e. nociceptor cells) using novel culture conditions. The nociceptors made using the methods of the present invention are further contemplated for various uses including, but limited to, use in in vitro drug discovery assays, pain research, and as a therapeutic to reverse disease of, or damage to, the peripheral nervous system (PNS). Further, compositions and methods are provided for producing melanocytes from human pluripotent stem cells for use in disease modeling.

From the description contained herein, one skilled in the art can easily ascertain the essential characteristics of this invention, and without departing from the spirit and scope thereof, can make changes and modifications to the present invention to adapt it to various usages and conditions and to utilize the present invention to its fullest extent. The embodiments and examples described below are to be construed as merely illustrative, and not limiting of the scope of the invention in anyway.

The inventors have previously disclosed the use of dual SMAD inhibition to direct differentiation of stem cells toward neural cell populations with the ratio of CNS and neural crest progeny being dependent on cell confluency at time of treatment initiation; high plating density, i.e. high confluency, yields CNS progeny whereas low plating density, i.e. low confluency, yields neural crest progeny. They further disclosed that patterning of differentiated CNS neuronal progeny to functional dopaminergic neurons could be achieved.

The present invention described herein discloses the unexpected and novel finding that functional nociceptors, a neural crest derived cell lineage, can be directly differentiated from high density plated embryonic or somatic stem cells in about 10 days by sequential inhibition of SMAD signaling followed by inhibition of FGF and Notch signaling and activation of Wnt signaling and such functional nociceptors can be maintained in vitro for 7 days or longer.

In particular, a combinatorial small molecule screen was done in order to discover compounds for use in directed differentiation of human pluripotent stem cells. During this screen small molecules were discovered that converted PSCs into postmitotic neurons. Specifically, a combination of five small molecules that were pathway inhibitors, i.e. SB431542, LDN-193189, CHIR99021, SU5402, and DAPT, was discovered that was sufficient under certain test conditions described herein to yield neurons at >75% efficiency from hPSCs within 10 days of differentiation in the absence of any recombinant growth factors. Accordingly, the use of compositions (including kits) and methods of the present inventions, results in at least a 50% yield of peptidergic nociceptors, or at least 60%, or at least 70%, or at least 75% efficiency from hPSCs. These resulting human neurons expressed canonical markers of nociceptive sensory fate including NTRK1, BRN3A, ISL1, NEUROG1, Substance P, and CGRP. This small molecule based acceleration of neuronal fate acquisition occurred in a time frame three to five fold faster compared to normal in vivo development (Bystron, et al., Nat Neurosci 9:880-886, (2006), herein incorporated by reference) indicating that inhibition of certain signaling pathways was sufficient to accelerate timing of human neuronal cell development. This rapid, potentially scalable (i.e. batch processing for producing large numbers of mature sensory peptidergic nociceptor neurons) and high efficiency derivation of peptidergic nociceptors allowed unprecedented access to this novel method for producing a medically relevant cell type for use in studies of human pain perception. Combinatorial small molecules screens represent a powerful method tool for a new generation of directed differentiation strategies in hPSC biology.

This discovery of compositions and methods for in vitro production of mature sensory peptidergic nociceptor neurons within 10 days represents significantly less time for producing mature sensory neurons than current methods. Prior to this discovery, in vitro derivation of postmitotic neurons from hPSCs required extended culture periods typically lasting 30 days or more (Zhang, et al., Methods Mol Biol 584:355-366 (2010); Elkabetz, et al., Genes Dev 22:152-165 (2008), herein incorporated by reference). This protracted in vitro differentiation of hPSCs was thought to reflect the chronology of human development in vivo (Perrier, Proc Natl Acad Sci USA 101:12543-12548 (2004). Thus, in one embodiment, compositions and methods for producing mature peptidergic nociceptor neurons includes less than 30 days of culture after initial contact with at least one of the five compounds, i.e. SB431542, LDN-19318, or equivalents. Accordingly, peptidergic nociceptors may be obtained in less than 29, less than 25, less than 20, less than 15, less than 12, and less than 10 days after initial contact with at least one of the five compounds.

Identifying in vitro strategies to overcome the slow human developmental pace is a major challenge for realizing the full potential of hPSCs in basic biology and human disease modeling (Saha, Cell Stem Cell 5, 584-595 (2009), herein incorporated by reference). The inventors describe herein the discovery of a novel small molecule based method to turn pluripotent cells into mature neurons. Thus in one embodiment, a pluripotent cell is directed to differentiation into a mature nociceptor cell. Further, the inventors describe materials and methods to produce mature neurons, i.e. nociceptor cells, in a variety of forms and in high numbers.

I. Cell Culturing Methods for Inducing Neuronal Precursor (Lineage) Cells: Contacting Human Pluripotent Stem Cells with SB431542 and LDN-193189 Produced Neural Lineage Cells.

The following example describes exemplary methods for providing cells of a neural lineage for use during development of the present inventions.

Dual SMAD inhibition was previously used as a rapid and highly effective method for inducing one type of neural lineage cells from hPSCs (Chambers, et al., *Nat Biotechnol* 27, (2009), herein incorporated by reference). These neural lineage cells induced by molecules including Noggin, had a default pathway that allowed development into central nervous system cells, i.e. neural cell fate. Follow up studies reported the use of a small molecule dorsomorphin (DM) instead of Noggin, that at least in part produced similar cells with differences in consistency of cultures (Kim, et al., Robust enhancement of neural differentiation from human ES and iPS cells regardless of their innate difference in differentiation propensity. *Stem Cell Rev* 6, 270-281, (2010); Zhou, et al., High-Efficiency Induction of Neural Conversion in hESCs and hiPSCs with a Single Chemical Inhibitor of TGF-beta Superfamily Receptors. *Stem Cells,* 504, (2010), herein incorporated by reference).

The inventors observed that cells generated using Noggin despite showing the same developmental stage as LDN treated cells, expression of the vast majority of the same markers, and capable of a similar developmental potential to make various neural lineages, also showed differences, such as being more anterior on an anterior-posterior axis (i.e. more forebrain, more cells express FOXG1, and the like) compared to neural cells induced using LDN. Thus although LDN was used in place of Noggin to inhibit BMP among other signaling pathways, Noggin and LDN may have other types of activities which are different, besides inhibiting BMP.

In part due to the high expense of using Noggin, the inventors contemplated that the use of a BMP inhibitor might be able to substitute for Noggin in producing cells of neural cell fate. Therefore, a small molecule BMP inhibitor, LDN-193189, (Yu, et al., *Nat Med* 14, 1363-1369, (2008), herein incorporated by reference) was used and found during the development of the present inventions to replace Noggin, in combination with SB431542, for generating primitive neuroectoderm from hPSCs, cells that have neural cell fate, i.e. CNS cells (FIG. 2A). This combination treatment was termed LSB for the combination of these two inhibitors LDN-193189 and SB431542.

In general, cell differentiation was initiated by treatment of high confluency monolayer hES or hiPS with dual inhibition of SMAD signaling. A preferred embodiment utilizes a percentage confluency of 50%-100%, with a most preferred embodiment of 70%-80% confluency. It will be obvious to one skilled in the art that the initial plating density required to achieve a preferred confluency of the present invention will be dependent on cell type, size, plating efficiency, survival, adhesion and other parameters which can be determined empirically without undue experimentation on the part of the skilled artisan. Dual inhibition of SMAD can be achieved with a variety of compounds including Noggin, SB431542, LDN193189, Dorsomorphin, or other molecules which block TGFβ, BMP, and Activin/Nodal signaling. A preferred embodiment utilizes the composition comprising SB431542 and LDN193189 (collectively, LSB) at a concentration of 0.1 μM-250 μM, or more preferable 1-25 μM, or most preferable 10 μM of SB431542 and 10-5000 nM, or most preferably 100-500 nM of LDN193189.

II. Compounds for Use in Directed Differentiation: Screening Small Molecules Using Neuronal Lineage Cells of the Present Inventions Resulted in Compounds that Produced PAX6 Low and TUJ1 High Neuronal Cells for Use in Directed Differentiation.

The following example describes using exemplary cells of a neural lineage from Example II for screening small molecule candidate compounds for use in directed differentiation.

Specifically, in the context of dual SMAD inhibition (LSB), i.e. human ES cells were first treated with LSB (LDN-193189 and SB431542) for screening candidate compounds (i.e. small molecules) under approximately 400 conditions in order to find combinations of small molecules that might accelerate the acquisition of postmitotic neuron markers starting from human ES cells. Candidate compounds were chosen from molecules that targeted (altered) cell signaling pathways known to be important and frequently used in developmental studies in order to determine cell fates (for example, signaling pathways such as FGF, Notch, WNT, SHH (Sonic Hedgehog), etc.) for determining cells capable of CNS development. As one example, 4 types of inhibitors (i.e. SU/DAPT/CHIR/Cyclopamine) were tested in different combinations (as fed to cells in cell medium) on different days of LSB treatment. Each treatment was then screened on Day 10 for TUJ1/PAX6 expression. As one example of a treatment condition: LSB was fed daily, CHIR and SU were added to the medium to feed cells daily on days 4-10.

In general, results of screening treatments resulted in large numbers of cultures containing dead cells. In other words, viable culture conditions during this screen were found much less frequently than unviable conditions (i.e. cell death), for example, when SU/DAPT was added to early cultures, i.e. prior to day 2. The inventors contemplated that CNS stem cells depend on FGF signaling and gamma-secretase activity/Notch signaling for survival, therefore when CHIR was absent when SU/DAPT induced cells to switch from CNS to neural crest, instead of switching, the cells died.

On day 10 after addition of LSB, cells that survived during the screen were monitored for the loss of the human neuroectoderm marker PAX6 (Zhang, et al., *Cell Stem Cell* 7, 90-100, (2010), herein incorporated by reference) and initiation of neuronal differentiation by TUJ1 expression (Lee, et al., *Cell Motil Cytoskeleton* 17, 118-132, (1990), herein incorporated by reference). The cells were stained for neurons (TUJ1+) and a loss of neuroectoderm (observation of fewer PAX6+ cells) using an antibody that binds the C-terminus of PX6), by immunofluorescence (immunoF). This screening was done on the numerous combinations of inhibitors (for example, SU, SU/DAPT, SU/DAPT/CHIR, DAPT/CHIR, SU/CHIR, SU/Cyclopamine, etc.) were added in variations of daily feedings on combinations of days, (for example, days 0-10, 1-10, 2-10, 3-10, etc.). In general, results were determined by observing comparative amounts of TUJ1+/PAX6− staining of cells generated by each treatment such that the conditions and compounds showing the highest amounts of TUJ1+/PAX6− staining were chosen as successful for providing cells for further analysis. One example of a small molecule that was considered a failure during the screening test for producing cells that were TUJ1+/PAX6− by immunostaining of cells was Cyclopamine. Cyclopamine appeared to have no effect on cells for producing TUJ1/PAX6 staining no matter when it was added. In other words, the cell morphology remained similar to those cells with LSB treatment alone (i.e. >90% PAX6+ and <10% TUJ1+) on day 10 by immunofluorescence.

However, during the screen the inventors discovered that a specific combination of three small molecules (SU5402, CHIR99021, and DAPT; termed 3i for three inhibitors), added on day 2 of LSB treatment (FIGS. 6A and B), abolished PAX6 expression and induced TUJ1 in hPSCs at day 10 of differentiation (FIGS. 2A and B). This was a surprising discovery because at day 2 of LSB treatment the treated cells were not yet known to have a neural cell fate or for having the capability to develop into a neural cell fate. Instead, 3i treatment directed cells away from a neural cell fate into neural crest cells which were further differentiated into the nociceptor cells of the present inventions.

The functions for each of these small molecules was then researched in order to discover which signaling pathways were contemplated to be involved in converting a PAX6+ TUJ1− human ES cell population into a PAX6-TUJ1+ population. First, S U5402 was reported as a potent inhibitor of VEGF, FGF, and PDGF tyrosine kinase signaling (Sun, et al., J Med Chem 42, 5120-5130, (1999), herein incorporated by reference). Thus in general it was contemplated that at least one of the small molecules was involved with inhibiting FGFR signally pathways. Secondly, CHIR99021 was reported as a WNT agonist by selectively inhibition of GSK-3β which stabilized β-catenin (Bennett, et al., J Biol Chem 277, 30998-31004, (2002), herein incorporated by reference). Thus in general it was contemplated that at least one of the small molecules was involved with inhibiting glycogen synthase kinase 3β (GSK3β). In one embodiment, this small molecule alternatively is capable of activating at least one of the WNT signalling pathways, such as through glycogen synthase kinase 3β (GSK3β) inhibition. And thirdly, DAFT was reported as a γ-secretase inhibitor capable of blocking Notch signaling (Dovey, et al., J Neurochem 76, 173-181 (2001), herein incorporated by reference). Thus in general it was contemplated that at least one of the small molecules was involved with inhibiting at least one Notch signaling pathway. Thus in one embodiment, one of the small molecules was contemplated as a nonselective or pan-Notch inhibitor. In another embodiment, one of the inhibitors is an inhibitor of γ-secretase molecules, capable of blocking at least one Notch signaling pathway. Therefore, in one exemplary embodiment, a combination of inhibitors would include at least one small molecule involved with inhibiting FGFR signalling pathways, at least one small molecule involved with inhibiting at least one Notch signaling pathway, and at least one small molecule involved with inibiting GSK-3β while activating at least one of the WNT signalling pathways for producing PAX6-TUJ1+ human neuronal cells of the present inventions. In further embodiments one of the inhibitors was capable of blocking at least one γ-secretase molecule in the Notch signaling pathway.

A. LSB-3i: a Combination of Two Inhibitors of FGF and Notch Signaling with an Activator of Wnt Signaling Produced TUJ1+ Neuronal Cells.

Inhibitors to FGF and Notch signaling and activators of Wnt signaling were added about 2, 3, 4, 5, 6, or 7 days after initiation of LSB treatment. Inhibition of FGF signaling can be achieved with a variety of compounds including SU5402, PD-161570, PD-173074, Suramin, or other molecules which block FGF signaling pathways. Inhibition of Notch signaling can be achieved with a variety of compounds including DAPT, L-685,458, Compound E, MK0752, or other molecules which block Notch signaling pathways.

Activation of Wnt signaling can be achieved with a variety of compounds including CHIR99021, LiCl, TDZD-8, recombinant Wnt or other molecules which activate Wnt signaling pathways. A preferred embodiment utilizes the composition comprising CHIR99021, DAPT, and SU5402 (collectively, 3i) at a concentration of 0.3-100 μM, or more preferable 3-10 μM, or most preferable 3 μM of CHIR99021; 1-100 μM, or most preferable 10 μM of DAPT; and 0.5-200 μM, or more preferable 5-20 μM, or most preferable 10 μM SU5402.

Figure 6:
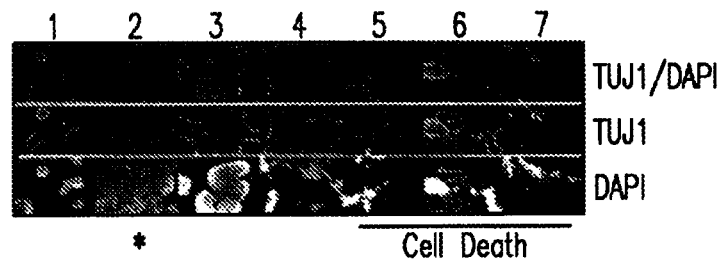
FIG. 6—Exemplary demonstration of 3i added when the cells still retain OCT4 expression—Demonstrates that a preferred embodiment of the present invention of combined use of LSB and 3i treatment drives nociceptor differentiation beginning very early in the differentiation pathway when the hESC population still retain pluripotent characteristics (A) When CHIR99021, DAPT, SU5402 are added to 7 duplicate cultures on various days (i.e. one culture on each of day 1-day 7) after LSB induction and the cells are fixed on day 11, the greatest cell survival and most homogeneous TUJ1 expression is observed for day 2. Thus the optimum day 2 time for 3i addition was discovered. (B) This corresponds to a time when the cells cultured in Noggin and SB431542 (NSB) continue to express OCT4, a marker for pluripotency, and do not yet express PAX6, a marker of neural cell fate (see lack of staining marked by an asterisk). Profound cell death is observed when 3i is added on days 5-7 at a time when the cells have committed the neural lineage, marked by PAX6 expression, see, DAPI staining in A) 3i added on days 5, 6 and 7 and B) day 6 of culture. Cells were stained for identifying antibodies that bound to OCT4 (dark) and PAX6 (light) in addition to a nuclear 4'-6 Diamidino-2-phenylindole (DAPI) stain.
Figure 6:
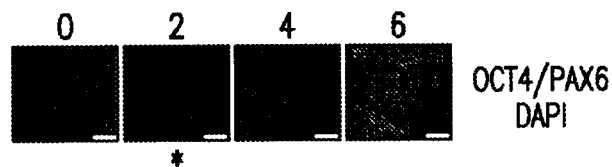

The stem cells treated with the combination of LSB and 3i were fixed on day 11 and examined for survival and expression of the neuronal marker TUJ1. The population that had been treated with 3i on day 2 of LSB treatment yielded the highest survival rate as well as high expression of the neuronal marker TUJ1 whereas the population that had been treated with 3i after day 5 of LSB treatment displayed cytotoxicity and cell death (FIG. 6A). Surprisingly, on day 2 following LSB treatment the cell population is still progenitor-like as expression of Oct4 is high (FIG. 6B). It is not until day 6 following LSB treatment that the neural commitment marker Pax6 is expressed; however treatment on day 6 with 3i results in cytotoxicity thereby indicating that the neuronal populations derived by combined LSB and 3i treatment are directly differentiating from the pluripotent stem cell and not from a neuronal intermediate. Therefore, a preferred embodiment of treatment with 3i is between 1 and 4 days following LSB treatment, with the most preferred embodiment of treatment with 3i 2 days following LSB treatment. Additionally, all 3 components of the 3i composition are required for the maximum yield of differentiated neurons (FIG. 2E).

TUJ1+ Neuronal Cells Show a Loss of Expression of Cell Proliferation Markers.

The following example describes an exemplary method for determining the maturational (cell cycle) stage of TUJ1+ neuronal cells.

Figure 2:
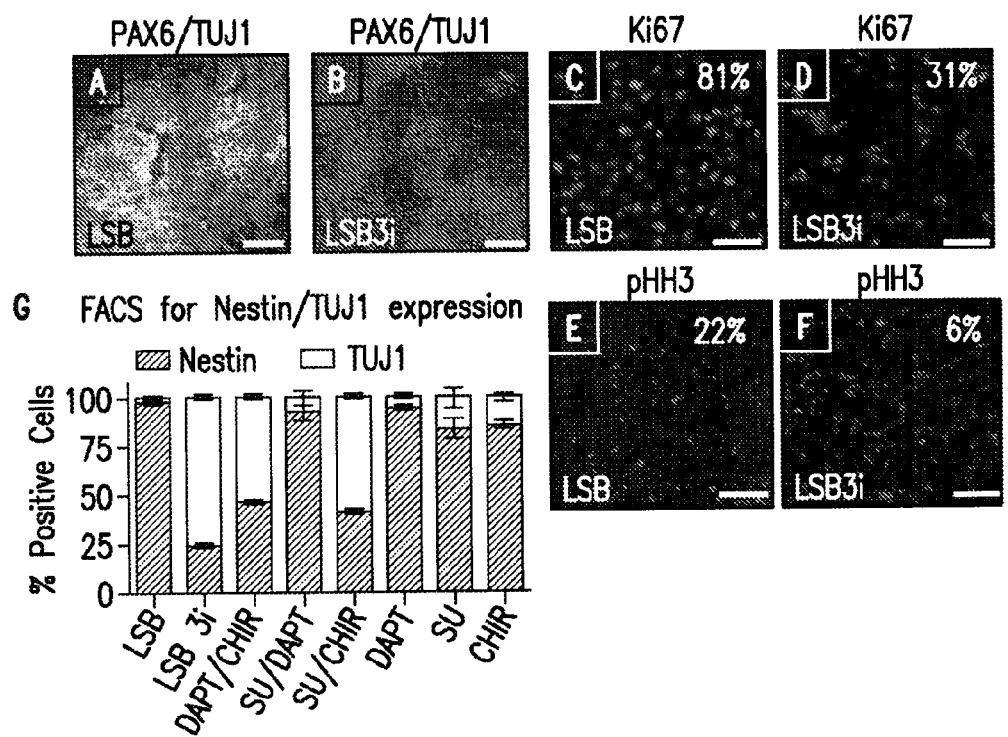
FIG. 2—Exemplary Efficiency of LSB3i—Demonstrates that a preferred embodiment of the present invention of combined use of LSB and 3i treatment efficiently promotes the generation of a neuronal like cell population compared to LSB treatment alone (A,B) Upon staining for TUJ1, a marker of neurons, far greater numbers of positive cells are observed when 3i is added (CHIR99021, DAFT, SU5402) 48 hours after treatment of hPSCs compared to LSB alone, which showed a large number of PAX6 dark cells with a few TUJ1+(light) cells. (C,D) Cells were re-spotted and Ki67 expression (light cells) was used to quantify the number of cells in cell cycle. Indicative of post-mitotic neurons, almost 3 fold less Ki67 (+) cells are observed when 3i is added compared to LSB alone. Comparing expression of Ki67 (light cells) and (E,F) phospho-histone H3 (PPH3) (light cells) in LSB (E) and LSB3i (F) treated hPSCs indicated a stark decline in proliferation by day 12. (G) Intracellular FACS was used to measure the number of progenitors (Nestin positive cells; grey bar) versus neurons (TUJ1 positive cells; white bar). In contrast to LSB treatment alone where approximately 5% of cells are TUJ1 positive, greater than 75% of cells are TUJ1 positive when 3i is added. When one or two of the three inhibitors were added compared to a preferred embodiment of the 3i composition, the same level of TUJ1 cells is not achieved. However treatment of LSB cells with CHIR (C) in addition to either SU5402 or DAPT will achieve greater than 53% neurons, indicating a requirement for CHIR, a glycogen synthase kinase 3β (GSK3β) inhibitor/activator of WNT signaling (i.e. WNT agonist) in combination with at least one inhibitor selected from a γ-secretase inhibitor and a fibroblast growth factor receptor inhibitor, in the formation of TUJ1+ neurons. Scale bar for (A,B) represents 200 μm and (C,D) represents 100 μm.

Upon maturation, neurons produced in culture ceased to undergo mitosis while loosing Ki67 and phospho-histone H3 (PHH3), markers of cell proliferation (Gerdes, et al., Int J Cancer 31, 13-20 (1983), herein incorporated by reference) and G2/M-phases of mitosis (Hendzel, et al., Chromosoma 106, 348-360 (1997), herein incorporated by reference), respectively. Therefore, cells produced using LSB in combination with 3i (i.e. LSB3i) were passaged to a lower density, approximately 10-100,000 cells/cm$^2$ and tested for cell proliferation markers, Ki67 and phospho-histone H3 (PHH3), after fixation to better assess expression, in individual cells. In particular, expression of Ki67 was known to be a better predictor of proliferation. Thus, compared to cells cultured in LSB without 3i compounds, after 12 days fewer cells, 50% and 16%, cultured in the presence of 3i showed a loss of Ki67+ and pHH3+ cells, respectively (FIG. 2 C-F).

Intercellular FACS staining for Nestin, a marker of neural progenitors, and β3-tubulin (TUJ1) a marker of neuronal differentiation, was performed to quantify the efficiency (percentage) of neuronal differentiation using LSB3i compared to LSB alone as a control in addition to LSB/CHIR (CHIR99021; C), SU/DAPT (SU5402/DAPT), SU/CHIR (SU5402/CHIR99021), DAPT, SU (SU5402), CHIR (FIG. 2G). In the presence of LSB, SU/DAPT, DAPT, SU and CHIR, the majority of cells expressed Nestin. In particular, >95% of the LSB cell population were Nestin+. Numerous cells showed Nestin staining after dual SHAD inhibition but were not quantitated while longer term cultured cells, i.e. 19 days, showed TUJI+ neurons where the majority of these cells co-expressed tyrosine hydroxylase (TH) identifying potential dopaminergic neurons (Chambers, et al., *Nat Biotechnol* 27, (2009), herein incorporated by reference). Conversely, when LSB contacted cells were contacted 2 days later with the 3i compounds, after 10 days approximately 25% of cells expressed Nestin while approximately 75% of cells expressed TUJ1, demonstrating efficient conversion to a neuronal cell fate after short-term cell culture, i.e. less than 19 days.

Surprisingly, LSB treatment followed 2 days later by contacting cells with CHIR99021 and either one of DAFT or SU resulted in 50% of the cell population differentiating into TUJ1+ cells. When each of the three inhibitors was used alone after LSB treatment, 20% or fewer cells were TUJ1+. Therefore CHIR99021 was discovered as the key contributor to directed differentiation of this cell population into TUJ1+ neuronal cells. The inventors contemplated directed differentiation of nestin+ TUJ1− cells into nestin−TUJ1+ neuronal cells was dependent on inibition of GSK-3β while activating at least one of the WNT signalling pathways in addition to inhibiting either FGF receptor pathways or a gamma secrease within a Notch signalling pathway. Further, the addition of the 3i compounds resulted in a conversion of an additional 25% nestin−TUJ1+ neuronal cells, see, FIG. 2G.

In summary, the neuronal population derived from a preferred embodiment of 3i treatment 2 days after LSB treatment was further examined. This population showed high expression of the neuronal marker TUJ1 compared to cells treated with LSB alone (FIG. 2A,B) as well as loss of Ki67 (FIG. 2C,D). Loss of Ki67 indicates reduction in cell cycle which is characteristic of post-mitotic differentiated neurons. Additionally, FACS analysis revealed that over 75% of the cell population treated with a preferred composition consisting of LSB and 3i expressed TUJ1 compared to 99% of the population treated with LSB alone which expressed Nestin, a progenitor marker (FIG. 2G).

The neuronal population derived from a preferred embodiment of 3i treatment 2 days after LSB treatment was further examined. This population showed high expression of the neuronal marker TUJ1 compared to cells treated with LSB alone (FIG. 2A,B) as well as loss of Ki67 (FIG. 2C,D). Loss of Ki67 indicates reduction in cell cycle which is characteristic of post-mitotic differentiated neurons. Additionally, FACS analysis revealed that over 75% of the cell population treated with a preferred composition consisting of LSB and 3i expressed TUJ1 compared to 99% of the population treated with LSB alone which expressed Nestin, a progenitor marker (FIG. 2E).

B. TUJ1+ Neuronal Cells Expressed PNS Rather than CNS Cell Markers.

The following example describes an exemplary method for identifying the type of TUJ1 positive neuron produced during the development of the present inventions.

To further characterize the subtype of neurons obtained from a preferred embodiment of 3i treatment 2 days after LSB treatment, the TUJ1 positive population was stained for markers of various neuronal subtypes. Specifically, the dual-SMAD-inhibition protocol was known to generate PAX6+ neuroepithelial cells biased towards anterior forebrain identity expressing FOXG1 (Forkhead box protein G1) (Chambers, et al., *Nat Biotechnol* 27, (2009), herein incorporated by reference). Therefore, in order to determine the neuronal subtype identity following LSB3i treatment, cells were passaged to a lower density, approximately 10-100,000 cells/cm$^2$ at day 10 and assessed for a range of marker expression at day 12

Since the expected neuronal type was a CNS fate, the majority of initial markers tested were for identification of CNS type cells. In fact, a CNS forebrain neuron was expected since LSB cells default to this subtype (PAX6, FOXG1 positive). Surprisingly, at least 12 negative results (an exemplary 10 are shown below) for CNS markers were obtained before staining for ISL1, a marker for PNS cells, was discovered. ISL1 is expressed by motoneurons and peripheral sensory neurons. BRN3A expression was tested and found to be expressed by LSB/3i cells. Therefore, the inventors discovered BRN3A+/ISL1+ neurons which indicated development of peripheral sensory neurons, see Table A, below.

TABLE A

The following list of genes/proteins that represent numerous CNS fate molecules that were expected to be positive (expressed) on cells using the LDN/3i induced differentiation as described herein. However, these results showed an exemplary lack of CNS markers, results which were supported by the subsequent finding of potential markers for PNS lineage, i.e. ISL1 and BRN3A.

| Gene/Protein | Marks (neuron type) | Result (IF or FACS) |
| --- | --- | --- |
| FOXG1 | Forebrain | Negative |
| FOXA2 | Midbrain | Negative |
| TBR1 | Cortical | Negative |
| PAX6 | Forebrain | Negative |
| AADC | Dopamine | Negative |
| TH | Dopamine | Negative |
| DCX | Pan-neuronal | >75%, costained with TUJ1 |
| Nestin | Progenitors | <25%, counterstained with TUJ1 |
| ChAT | Cholinergic | Negative |
| GAD65 | GABA | Negative |
| Reelin | Cortical and juvenile neurons | Positive |
| GABA | GABA | Negative |
| MASH1 | Autonomic | Negative |
| BRN3A | Peripheral sensory | Positive |
| ISL1 | Motoneurons, Peripheral sensory | Positive |

Surprisingly, homogenous expression of ISL1 and BRN3A (red/darker areas within cells) (FIGS. 3A and B) were observed on TUJ1+ cells (green/lighter cell bodies compared to red staining) of the present inventions. ISL1 and BRN3A are key markers for sensory neurons (ISL1: Sun, et al., *Nat Neurosci* 11, 1283-1293, (2008); BRN3A: Gerrero, et al., *Proc Natl Acad Sci USA* 90, 10841-10845 (1993), all of which are herein incorporated by reference). This discovery indicated that the neurons that resulted from LSB3i treatment were PNS rather than CNS cells. These results were in contrast to LSB cells that default to a CNS forebrain neuron subtype (PAX6+, FOXG1 positive). This is quite a unexpected finding as the high confluency of the stem cells upon initiation of the treatment, as represented by plating density, according to the teachings of the prior art, should have resulted in CNS derived neuronal populations. However, nociceptors are derived from neural crest cell populations which, according to the teachings of the prior art, are derived from low confluency of the stem cells upon initiation of the treatment, as represented by plating density. In other words, the expectation was that a high initial plating density>20,000 cells/cm$^2$ of pluripotent stem cells at the time of initiation of LSB treatment would result in a committed CNS neuronal population. In contrast, a low initial plating density approximately 10,000 cells/cm$^2$ was known to be necessary to result in neural crest cells (Chambers et al, Nature Biotech, 2009 (See lower half of FIG. 4), herein incorporated by reference in its entirety).

Figure 3:
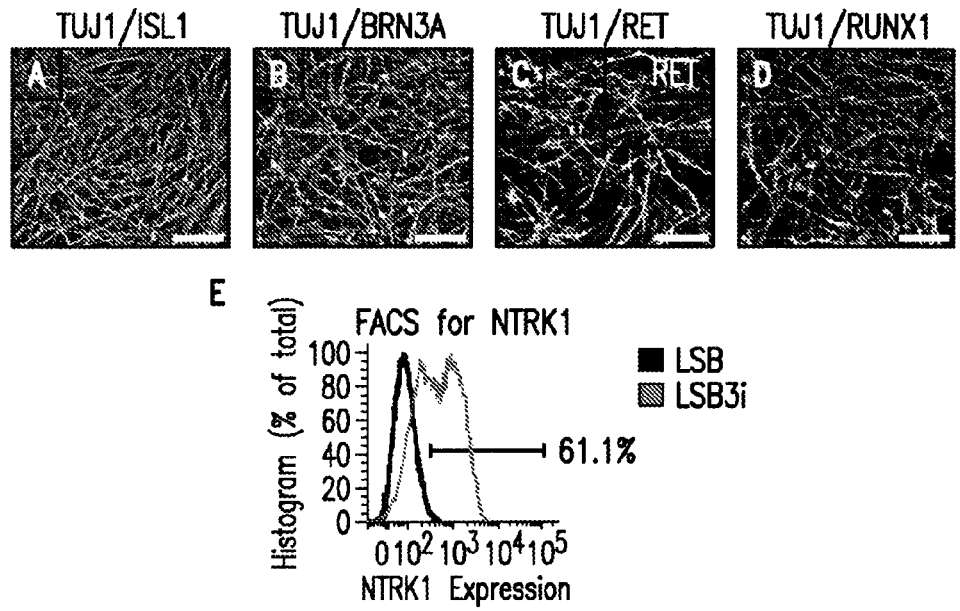
FIG. 3—Exemplary LSB3i neurons were nociceptors—Demonstrates that a preferred embodiment of the present invention of combined use of LSB and 3i treatment efficiently promotes the generation of nociceptors compared to LSB treatment alone. TUJ1 positive neurons from the combined use of LSB and 3i treatment express (A) ISL1, (B) BRN3A, (C) RET, and (D) RUNX1 measured by immunofluorescence on Day 12. (E) Greater than 61% of-cells express NTRK1 on Day 10 while LSB3i treated hiPSCs form neurons at a moderate efficiency as measured by FACS. These results taken together indicate the vast majority of neurons generated using the combined use of LSB and 3i treatment are nociceptors. Scale bar represents 100 μm.
Figure 4:
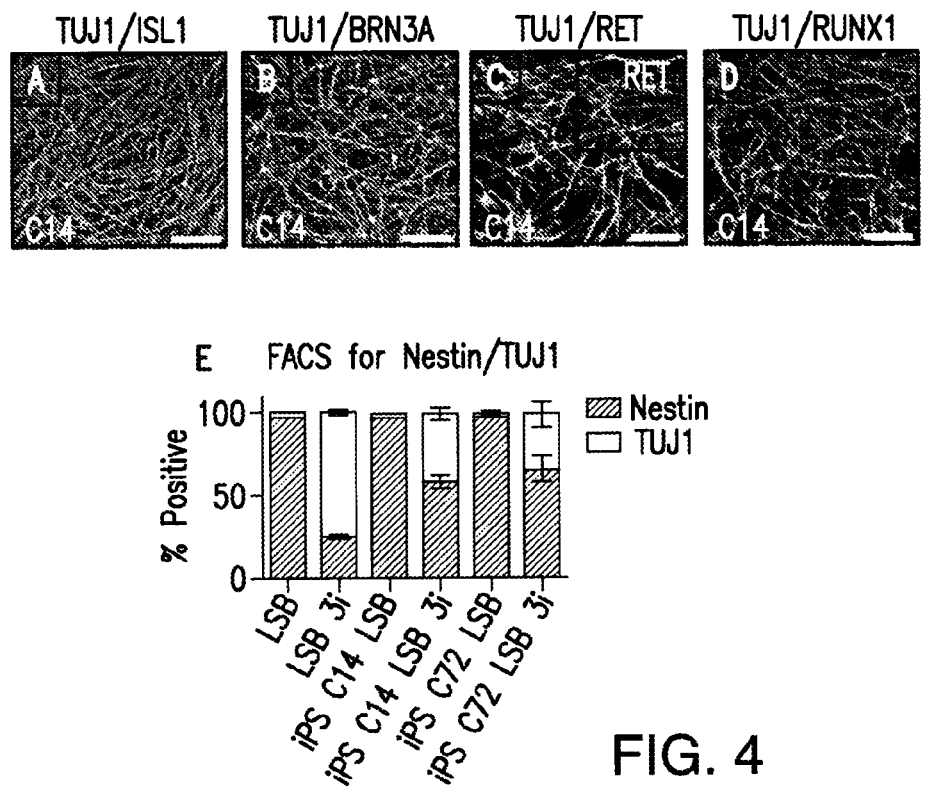
FIG. 4—Exemplary iPS cells were induced to nociceptors using LSB3i—Neurons similar to those shown in FIG. 3 are observed when hiPSC lines (for example, C14) are treated with LSB3i. Demonstrates that a preferred embodiment of the present invention of combined use of LSB and 3i treatment efficiently promotes the generation of a nociceptor compared to LSB treatment alone from hiPSC populations. TUJ1 positive neurons from a preferred embodiment of combined use of LSB and 3i treatment of a hiPSC line (C14) express (A) ISL1, (B) BRN3A, (C) RET, and (D) RUNX1 measured by immunofluorescence on Day 12. Two different hiPSC lines (C14 and C72) are also able to generate nociceptors. (E) Intracellular FACS was used to measure the number of progenitors (Nestin positive cells; grey bar) versus neurons (TUJ1 positive cells; white bar) for the treatments shown. Scale bar represents 100 μm.

To further characterize the subtype of neurons obtained from a preferred embodiment of 3i treatment 2 days after LSB treatment, the TUJ1 positive population was stained for markers of various neuronal subtypes. This population was positive for expression of ISL1, BRN3A, RET, and RUNX1 (FIG. 3 A-D). FACS analysis revealed that greater than 60% of these neurons were positive for NTRK1 (FIG. 3E).

These markers collectively indicate that the neuronal population are peripheral sensory neurons, in particular nociceptors. This is quite a unexpected finding as the high confluency of the stem cells upon initiation of the treatment, as represented by plating density, according to the teachings of the prior art, should have resulted in CNS derived neuronal populations. However, nociceptors are derived from neural crest cell populations which, according to the teachings of the prior art, are derived from low confluency of the stem cells upon initiation of the treatment, as represented by plating density. Therefore a preferred embodiment of the combination of LSB with 3i treatment on day 2 results in unexpected formation of neural crest derived populations, namely nociceptors. To establish the generality of the present invention, the inventors repeated a preferred embodiment of the present invention combining 3i treatment 2 days after LSB treatment using hiPSC as the source of stem cells. The current art describes any number of methods to produce hiPSC and will be known to those skilled in the art. hiPSC cells plated at a high confluency treated with LSB followed by 3i on day 2 results in the formation of neuronal cells positive for the nociceptor markers ISL1, BRN3A, RET, and RUNX1 (FIG. 4A-D).

C. PNS TUJ1+ Neuronal Cells Expressed Nociceptor– Peptidergic Cell Markers

The following example describes using exemplary methods for determining which type(s) of peripheral nervous system (PNS) neurons were produced using methods described herein.

It was not known what type(s) of PNS neurons were produced by the methods described herein as there were several types of candidate neurons, such as sensory neurons and motor neurons, and further there were at least three major subsets of known sensory neurons in the PNS including proprioceptor cells, mechanoceptor cells, and nociceptor cells.

During development, early stage nociceptors were both peptidergic and nonpeptidergic and uniquely expressed NTRK1, RUNX1, followed by RET expression (for an example of information on RET, see, Woolf, et al., *Neuron* 55, 353-364, (2007), herein incorporated by reference). Duplicate early stage LSB3i-cultures with TUJ1+ neurons were tested for RET expression (FIG. 3C), and discovered to be positive for this marker (red/darker areas within cells in the larger box compared to TUJ1+ staining (green/lighter cell bodies compared to RET staining) and lighter stained areas within inserted RET box). (FIG. 3D), and greater than 60% of all cells in culture expressed NTRK1 when measured by FACS at day 10 (FIG. 3E).

In summary, this population was positive for expression of ISL1, BRN3A, RET, and RUNX1 (FIG. 3A-D) indicating the production of early stage nociceptors (both peptidergic and nonpeptidergic). FACS analysis revealed that greater than 60% of these neurons were positive for NTRK1 (FIG. 3E). These markers collectively indicate that the neuronal population are peripheral sensory neurons, in particular nociceptors.

Therefore a preferred embodiment of the combination of LSB with 3i treatment on day 2 results in unexpected formation of neural crest derived populations, namely nociceptors.

Further, the inventors combined information from several tests, including initial immunofluorescence results, i.e., BRN3A+, ISL1+, array data, i.e. TACT (Substance P) expression, then choosing a NTRK1 marker and finding NTRK1+ cells, in addition to observations described herein where cells obtained by LSB/3i treatment transitioned through neural crest and transiently expressing Neurogenin1 (NEUROG1) instead of differentiating into a CNS fate. Thus the inventors contemplated that the resulting PNS cell was most likely a peptidergic nociceptor.

D. LSB-3i Reproducibly Induced PNS TUJ1+ Nociceptor– Peptidergic Neuronal Cells.

The following example describes using exemplary methods of the present inventions for determining reproducibility.

To establish the generality of the present invention, the inventors repeated a preferred embodiment of the present invention combining 3i treatment 2 days after LSB treatment using hiPSC as the source of stem cells. Reproducibility of LSB3i treatment was accessed across additional hPSC lines including induced pluripotent stem cell (hiPSC) lines. The current art describes any number of methods to produce hiPSC and will be known to those skilled in the art. In particular, two hiPSC lines (C14 and C72) were used that were generated by inserting genes such as Oct4 (octamer-binding transcription factor 4), Sox2 (SRY (sex determining region Y)-box 2), Klf4 (Kruppel-like factor 4), and c-Myc (Transcription factor p64) and shown to efficiently neuralize (see, (Papapetrou, et al., *Proc Natl Acad Sci., USA* 106, (2009), herein incorporated by reference)).

PAX6 expression was then examined by ImmunoF. LSB and LSB3i treatment of C14 and C72 cell lines showed similar neuronal staining results when compared to human cell lines shown in FIG. 3A-D. Exemplary C14 staining results are shown in FIG. 4A-D while exemplary C72 staining results are shown in FIG. 8A-D for ISL1, BRN3A, RET, RUNX1 and TUJ1, as described above.

Figure 9:
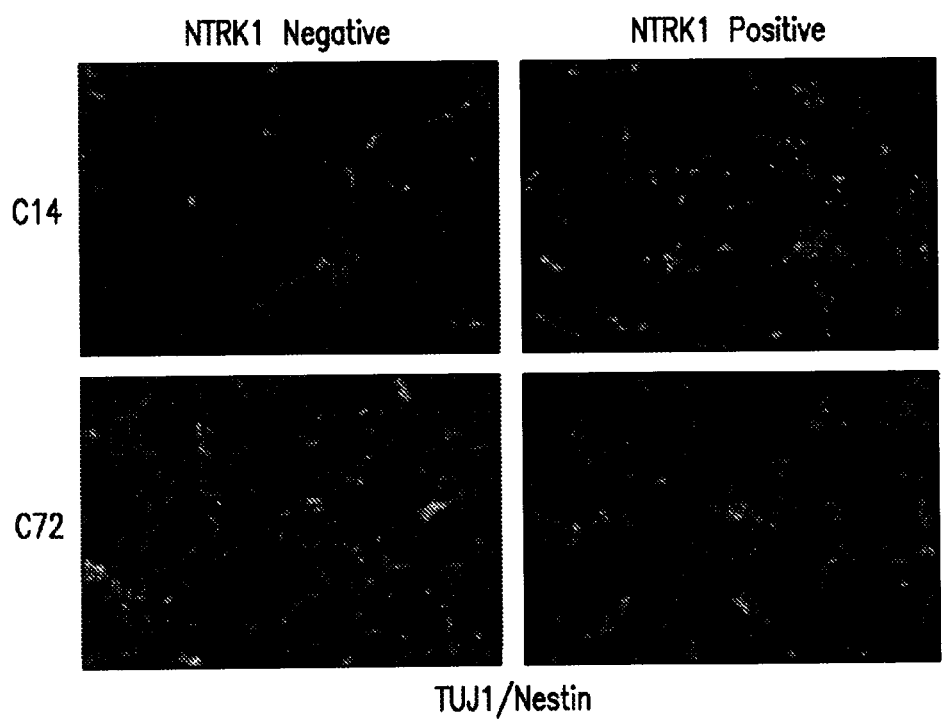
FIG. 9—Exemplary NTRK1 FACS sorting enriched hiPSC-derived LSB3i neurons. NTRK1 FACS sorting on day 10 of differentiation increased TUJ1 positive (light axonal stain) neurons in NTRK1+ cells and removed nestin positive progenitor (NTRK1−) cell populations from both C14 and C72 cell lines. Cells were immunostained with TUJ1 and Nestin in addition to DAPI 24 hours after plating onto a matrigel coated culture vessel.

LSB treatment of C14 and C72 cell lines homogeneously gave rise to Nestin positive cells (>95% of the treated cell population) and were capable of forming TUJ+ cells when treated with combination of LSB3i as measured by FACS (40% for C14 and 33% for C72; FIG. 4E). These results were compared to H9 cell line (i.e. a hESC line) treated with LSB and LSB3i shown for LSB and LSB3i results in (FIG. 4E). Even higher neuron yields, from 40% and 33% measured by FACS, became >90% of nuclei staining are neurons when sorted on NTRK1 were obtained in those two hiPSC lines upon passaging of bulk cultures into culture vessels coated with Matrigel™ containing N2 media after sorting on NTRK1 (Neurotrophic tyrosine kinase receptor type 1) marker expression. Cells were disaggregated with accutase, re-suspended in N2, and incubated on ice with APC-conjugated NTRK1 antibody (R&D) for 15 minutes, washed, and re-suspended in N2 for FACS. After sorting the cells were cultured for 24 hours in N2 media, and fixed in place. Cells were collected and stained for BRN3A, ISL1, TUJ1 and DAPI. In particular, numerous Nestin+ cells (red/dark staining) are shown for both C14 and C72 NTRK1− cells from LSB3i treated cells compared to few Nestin+ cells in the representative NTRK1+ LSB3i treated cell population (FIG. 9). Further, while few C14 NTRK1− cells expressed TUJ1 cell line C27 showed a higher number of NTRK1− TUJ1+ (green; bright staining). Both cell lines showed high numbers of Nestin−TUJ1+ cells as observed compared to cell bodies identified by DAPI (blue; light nuclear) staining.

In summary, hiPSC cells plated at a high confluency treated with LSB followed by 3i on day 2 resulted in the formation of neuronal cells positive for the nociceptor markers ISL1, BRN3A, RET, and RUNX1 (FIG. 4A-D, FIG. 8A-D and FIG. 9.

The speed with which stable, mature neuronal cell fates can differentiate from hPSCs using this combined small molecule approach (FIG. 4) remains the most surprising finding. The time frame of 10-15 days for the generation of a mature neuron phenotype is far accelerated as compared with estimates of nociceptor emergence during human development (30-50 days) (Kitao, et al., *J Comp Neurol* 371, 249-257, (1996), herein incorporated by reference). Upregulation of ISL1 and BRN3A are concomitant with expression of SOX10, starting between days 5 and 7. The optimal time to add 3i is day 2 of dual SMAD inhibition reflecting a previous finding from the inventor's lab that treatment with sonic hedgehog at day 2 is most effective at promoting FOXA2 expression and human floor plate differentiation (Fasano, et al., *Cell Stem Cell* 6, 336-347, (2010), herein incorporated by reference). This suggests that neural patterning can occur prior to the loss of OCT4 protein expression and that the presence of OCT4 protein does not appear to restrict pre-patterning events. The potent role of CHIR99021 in the derivation of neural crest derived sensory neurons is likely related to activation of canonical WNT signaling, known to be essential during early neural crest specification of (Dorsky, et al., *Nature* 396, 370-373, (1998), herein incorporated by reference), and capable of instructing naive neural crest precursors towards sensory neuron lineage (Lee, et al., *Science* 303, 1020-1023, (2004), herein incorporated by reference).

Transcription factor-based lineage reprogramming of mouse cells has garnered much deserved attention as a means to derive neurons directly from fibroblast (Vierbuchen, et al., *Nature* 463, 1035-1041, (2010), herein incorporated by reference), and in time this method may be used on human cells. The data shown herein demonstrated that LSB3i was capable of rapid derivation of human postmitotic neurons. Some of the key advantages of using methods comprising LSB3i were speed and efficiency of production of human postmitotic neurons from human precursor cells, i.e. PSCs. Furthermore, the protocol did not require genetic manipulation or mechanical intervention, such as passaging, resulting in highly enriched populations of neurons within 10 days in a single culture step.

LSB3i is also one of the first examples of using combinatorial small molecule screens to drive lineage specification in hPSCs. Given the limited number of developmental pathways used iteratively at developmental decision points (Brivanlou, et al., *Science* 295, 813-818, (2002), herein incorporated by reference) the approach described herein should be generally applicable to specify human pluripotent lineages. The majority of the five small molecules used in LSB3i were known signaling pathway inhibitors indicating that suppression of endogenous signaling pathways is particularly effective at directing hPSC fate. Although off-target effects are an important consideration when using small molecules, such that small molecules often produce unintended or unexpected results, the data obtained during the development of the present inventions demonstrated that in this particular invention wherein combined small molecule inhibition of endogenous signaling pathways provided efficient, non-genetic (no changes in DNA coding sequences), cross-species, cost effective, rapid, and reversible means to modulate hPSC cell fates.

III. LSB-C: CHIR99021 was Required for the Generation of LSB3i Nociceptors and Discovered to Direct Differentiation into Neural Crest Stem Cells.

During the development of the present inventions, the inventors discovered that LSB contacted cells were capable of being directed to differentiate a high numbers into nociceptors when contacted, on Day 2 after LSB treatment, with CHR/SU or CHR/DAPT but not SU/DAPT. Upon further investigation the inventors were surprised to discover that LSB-C, LSB treated cells contacted with CHIR resulted in a neural crest stem cell population.

A. CHIR99021 (C) is the Key Factor for Inducing Neuronal Differentiation as from LSB Cultured Cells (i.e. LSB-C)

The following example describes using exemplary methods for testing the efficacy of each compound for inducing directed neuronal differentiation.

In order to gain mechanistic insights into the sufficiency of each compound found to associated with the induction of TUJ1+ cells of Example III, specific combinations of 3i compounds were tested for inducing cellular expression of Nestin and TUJ1 as measured using intercellular FACS (shown in FIG. 1G). Nestin was used as a marker of the LSB neural lineage cells while TUJ1 was used to identify a downstream (i.e. more differentiated) neuronal cell.

Although none of the individual factors yielded high numbers (greater than 60%) of TUJ1+ neurons, CHIR99021 in combination with either one of the other two signal inhibition factors was capable of generating moderate numbers of TUJ1+ neurons (53% for DAPT and 58% for SU5402). These data indicate that under the test conditions used herein, CHIR99021 was the key factor for accelerating neuronal differentiation while SU5402 and DAPT provided important, yet additive stimuli.

Additionally, all 3 components of the 3i composition are required for the maximum yield of differentiated neurons (FIG. 2G).

B. Neural Crest Stem Cells were Derived from LSB Contacted Cells (D0) Further Contacted with CHIR (D2).

The inventors found that BMP signaling and TGF-β signaling was optimized for neural crest induction through experiments that used early withdrawal of theses respective inhibitors. Wnt signaling was activated in turn along with GSK3β inhibition, a using a small molecule GSK3β inhibitor (CHIR99021). Thus the inventors found that a narrow window (Day 2) of Wnt signaling governs neural crest induction in the context of the dual SMAD inhibition protocol. A modified dual SMAD inhibition protocol (LSB-C) that combined optimized signaling for these three pathways enhanced the induction of Sox10::GFP expressing neural crest in up to 65% of the population.

IV. LSB-3i and LSB-C Induced Artificial SOX10+ Cells are Capable of Producing Nociceptor Cells.

The following example describes using exemplary methods of the present inventions for directed differentiation of engineered SOX10+ GFP expressing human cells.

Nociceptor cells are contemplated to arise from two types of cell intermediates during human development: specifically SOX10+ chick embryo neural crest cells were found to be capable of generating trunk nociceptor cells flanking the spinal cord (George, et al., Nat Neurosci 10:1287-1293, (2007), herein incorporated by reference). Additionally, Xenopus laevis head placode tissue contributed to the trigeminal nociceptor cell population in facial tissue (Schlosser, et al., J Comp Neurol 418:121-146, (2000); Schlosser, et al., Dev Biol 294:303-351, (2006), herein incorporated by reference).

Thus, in order to determine if a neural crest intermediate cell fate marked by SOX10 (Aoki, et al., Dev Biol 259, 19-33, (2003); Lee, et al., Nat Biotechnol 25, 1468-1475, (2007), herein incorporated by reference) in human cells would be observed during differentiation using a transgenic SOX10::GFP bacterial artificial chromosome (BAC) hPSC line. This SOX10:: GFP (BAC) cell line was generated with enriched neural crest gene markers that co-expressed with a GFP gene using methods previously reported (Placantonakis, et al., Stem Cells 27:521-532, (2009), herein incorporated by reference). The SOX10:GFP cell line was a subclone of the H9 hESC line. Cells were dissociated and gene delivery was performed using reagents (solution V), protocol (B-16), and equipment from Amaxa. The DNA nucleofected (transfected into the nucleus) was a bacterial artificial chromosome (BAC) containing the SOX10 gene with an inserted GFP, obtained from Gene Expression Nervous System Atlas [GENSAT] (accession number: GENSAT1-BX1086). The BAC was then modified to include a neomycin resistance gene for selection (see Tomishima, et al. Stem cells 25(1):39-45. Epub 2006 Sep. 21 (2007, herein incorporated by reference) using cre/LoxP recombination from a selection cassette excised from the pL452 plasmid into the GENSAT BAC. After gene delivery hESCs were seeded as single cells in the presence of G418 for neomycin resistance selection and clones were manually picked and screened for the presence of GFP upon differentiation. GFP cells were sorted to confirm the expression of SOX10 and other neural crest markers by qRT-PCR.

GFP expression was measured by FACS identification and sorting of SOX10::GFP+ cells at 4, 8, 12, and 16 days after initiating differentiation with LSB when two additional duplicate samples were contacted each with one of LSB then CHIR99021 (LSB/C) or LSB with 3i.

Figure 5:
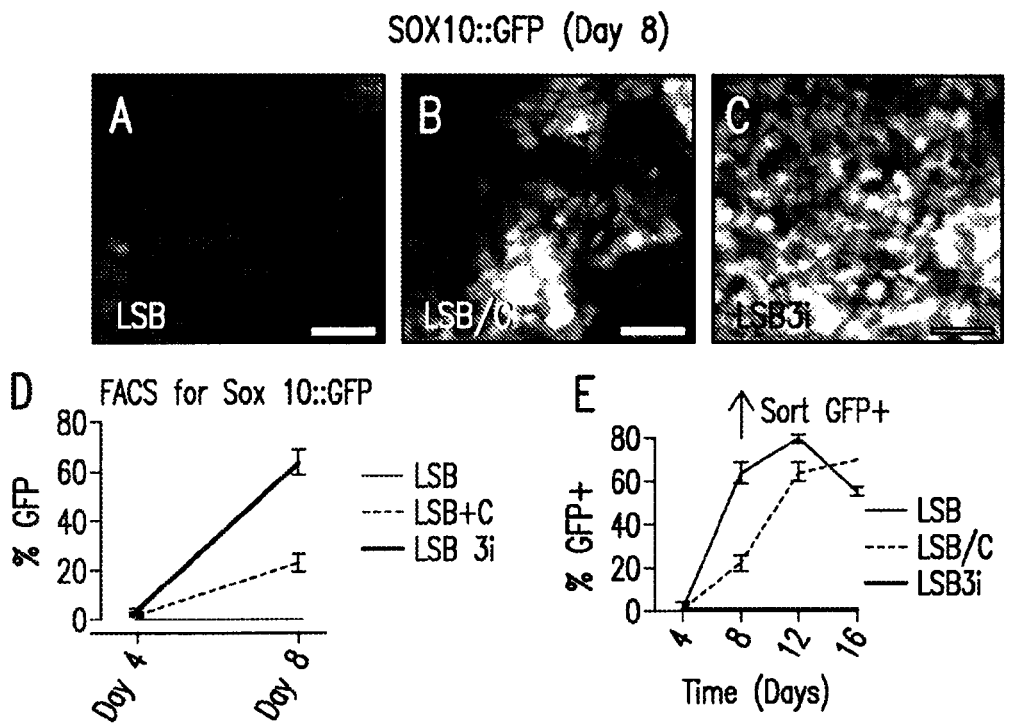
FIG. 5—Exemplary SOX10 expression—Demonstrates that a preferred embodiment of the present invention of combined use of LSB and 3i treatment drives nociceptor differentiation through a pathway involving a neural crest stem cell-like state. To monitor the emergence of neural crest stem cells, a transgenic SOX10::GFP BAC hESC cell line was treated with A) LSB, B) LSB and CHIR99021 (LSB/C), and C) LSB3i which showed numerous (bright GFP+ cells in B) and C) by fluorescence microscopy. D) and E) show quantitative expression of GFP in treated cell populations after flow cytometry analysis Using a transgenic SOX10::GFP BAC hESC line, expression of SOX10, a marker of neural crest stem cells, can be detected in greater than 64% of cells by day 8. SOX10::GFP+ expression was accelerated and maximal expression (80% GFP+ by day 12) where larger GFP+ populations occurred earlier compared to LSB and CHIR99021 (LSB/C) or LSB treatment alone as shown in D) and E) LSB values are just above baseline, LSB/C points are black lines (in between LSB and LSB3i) and LSB3i values are connected by a red (light) line. Scale bars=50 μm.

When CHIR99021 was present greater than 70% of these treated cells in culture became SOX10::GFP+ by day 12 of differentiation for the culture conditions (70% for LSB/C and 80% for LSB3i; FIGS. 5D and E). This result indicated that the majority of cells develop a neural crest identity, supporting the inventors' observation that CHIR99021 was required for the generation of LSB3i nociceptor cells. Thus combined inhibition by these small molecules which inhibited tyrosine receptor kinase receptors and Notch signaling, in addition to contacting SU5402 and DAPT, respectively, accelerated neural crest cell fate, since LSB3i treated cells acquired a neural crest fate more rapidly in comparison to LSB/C treated hPSCs (FIGS. 5D and E). The inventors contemplated that CHIR induced neural crest and sensory neurons while SU accelerated neural crest marker expression and neuronal differentiation. Finally, the inventors contemplated that DAFT in combination with CHIR and SU accelerated neuronal differentiation. Further, the use of CHIR99021 in combination with LSB, i.e. LSB/C resulted in a slower conversion rate of over 60% of Nestin–TUJ1+ neuronal cells compared to LSB3i between days 12 and 16 when using the engineered SOX::GFP cells as a read-out.

V. NTRK1+ Human Nociceptor Cells Produced by Methods Described Herein Showed Electrophysiology Responses Similar to Rat Nociceptor Cells In Situ.

The following example describes using exemplary methods of the present inventions for determining the functional capability of nociceptor cells produced by methods described herein.

Figure 12:
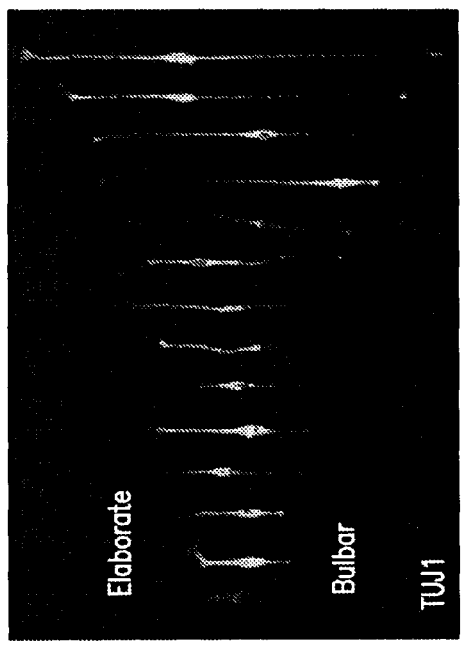
FIG. 12—Exemplary LSB3i nocicepors have two distinct growth cones. When passaged at day 12 following initial contact with LSB, LSB3i nociceptors were fixed and stained with TUJ1 antibodies (light areas) and DAPI (dark nuclei) two distinct growth cones can be observed in these representative cells with a cell body marked by DAPI (darker oval areas) nuclear area in between with a variety of axon-like shapes and sizes. One end exhibited an elaborate arborization (top) similar to dendrites and the other a bulbar shape (bottom) similar to synaptic ends. In general, the morphology of peptidergic nociceptors of the present inventions matched morphology of sensory neurons.

LSB3i treated cells were examined for function, maturation stages, and behaviors in order to confirm that LSB3i derived neurons were bona fide nociceptor neuronal cells. After LSB3i treatment of pluripotent stem cells resulted in nociceptor cells were obtained long term cultures were established from a plating density of 10-100,000 cells/cm$^2$ and passaged Day 10, 30 days in culture in N2 medium supplemented with human-beta NGF, BDNF, and GDNF (see, Example I for additional details). Survival rate of these cells under longer-term culture conditions was found to be NGF dependent compatible with NTRK1+ nociceptor status. LSB3i nociceptors expressed high levels of TUJ1, ISL1, BRN3A (FIG. 7A-C) as shown previously, in addition to glutamate (FIG. 7C). Glutamate production was consistent with an excitatory glutamatergic neuron, i.e. a nociceptive afferent fiber that releases glutamate, and the capsaicin receptor TRPV1 (FIG. 7D), an important ion channel for noxious stimulus. On day 15 in culture two distinct growth processes could be identified for each neuron (FIG. 7E, FIG. 12).

Figure 7:
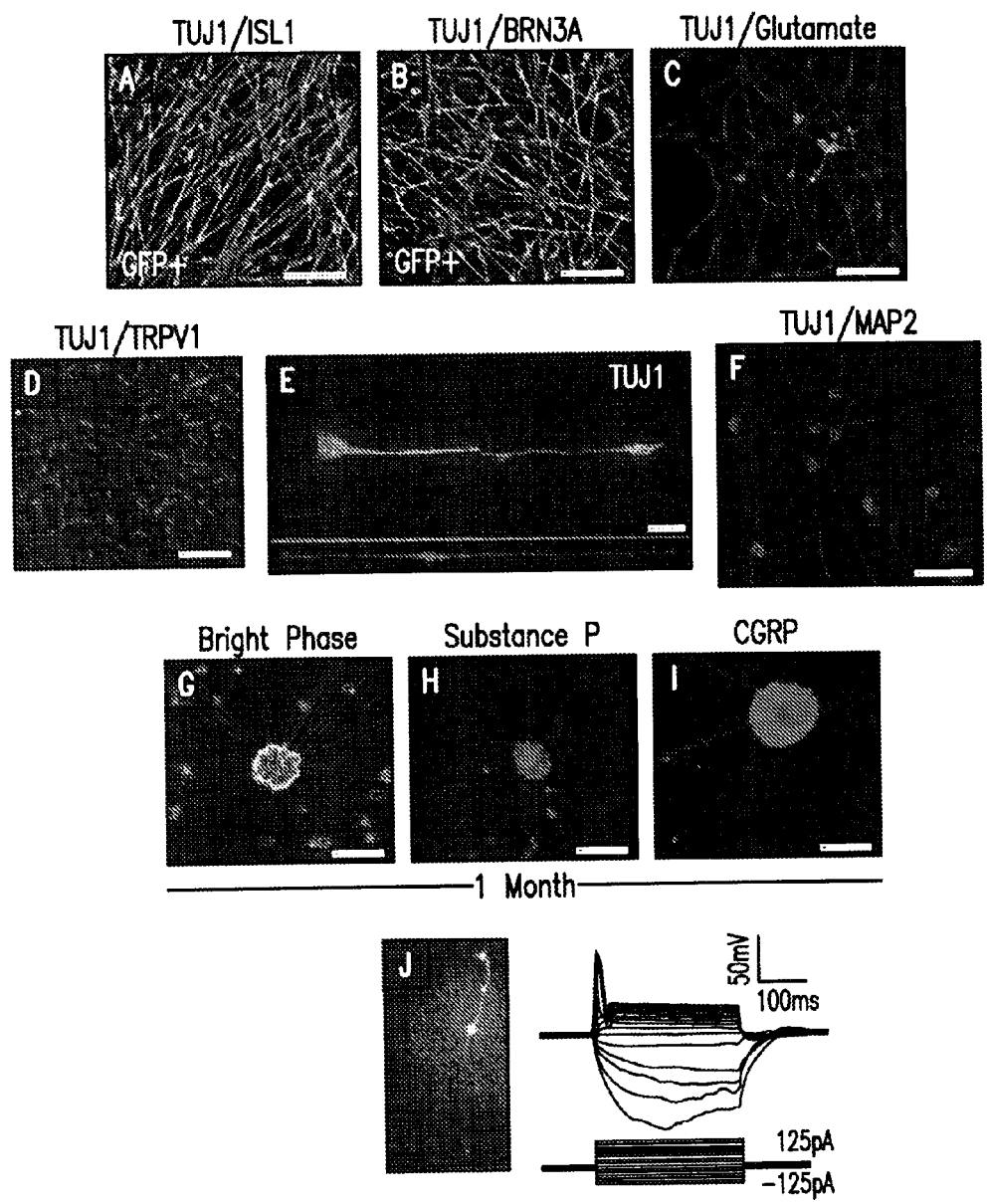
FIG. 7—Exemplary LSB3i treated artificial hPSCs (SOX10::GFP cells) demonstrated development of a neural crest intermediate cell with accelerated maturation into bipolar nociceptors capable of producing an action potential. Flow Cytometry was used to sort SOX10::GFP+ cells from SOX10::GFP negative cells. When SOX10::GFP+ were treated with LSB3i they gave rise to (produced) (A) ISL1 and (B) BRN3A positive neurons. LSB3i neurons stained for (C) glutamate and (D) TRPV1. (E) Each TUJ1 positive neuron exhibited a bipolar morphology with two distinct growth cones and (F) expressed polarized MAP2. After 1 month, (G) neuron cell bodies cluster to form ganglia positive for (H) Substance P and (I) CGRP. (J) 95 pA is sufficient to elicit a mature single action potential from LSB3i nociceptors. Scale bar represents 100 µm (A-D and F-I) and 50 µm (E).
Figure 8:
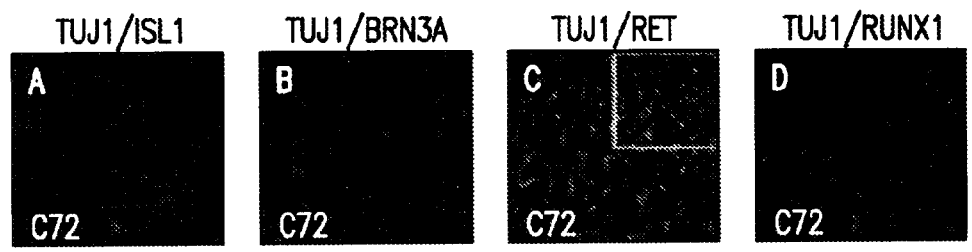
FIG. 8—Exemplary LSB3i treated iPSC clone C72 rapidly acquired a nociceptor phenotype. TUJ1 positive cells (light axonal stain) from LSB3i treated iPSC clone C72 cells expressed A) ISL1, B) BRN3A, C) RET and D) RUNX1 (stained cell bodies).

The dendrite marker MAP2 was expressed primarily in one of the two processes in a polarized fashion (FIG. 7F). The bipolar nature of the neurons was in agreement with the role of sensory neuron in the peripheral ganglia with the cell body is located in the dorsal root ganglion projecting processes both towards the spinal cord and towards the periphery (Woolf, et al., Neuron 55, 353-364, (2007); George, et al., Nat Neurosci 10, 1287-1293, (2007), herein incorporated by reference).

In the presence of nerve growth factor (NGF), neurons were cultured long-term (for example, cells passaged day 10 and cultured up to day 30). LSB was withdrawn on day 5, 3i withdrawn from cells on day 10 when NGF/GDNF/BDNF were added into medium. The neurons were fed NGF/GDNF/BDNF from day 10 up to day 30. On Day 30, the number of days from initial LSB treatment, the neurons was observed to have started to self-organize into ganglia-like structures. This type of morphology is common to peripheral sensory neurons (Marmigere, et al., Nat Rev Neurosci 8, 114-127, (2007), herein incorporated by reference) (FIGS. 7G, H, and I).

Mature nociceptors are typically either peptidergic or non-peptidergic depending on expression of neuropeptides, such as calcitonin gene related peptide (CGRP) and Substance P (a neuropeptide) expressed by peptidergic sensory neurons, (Woolf, et al., Neuron 55, 353-364, (2007), herein incorporated by reference). In contrast, non-peptidergic neurons do not express CGRP nor Substance P and have other markers such as binding to the lectin $IB_4$.

Therefore, LSB3i induced neurons were sorted for NTRK1 expression (see methods described above), using FACs, into NTRK1+ and NTRK1− populations (for example of a sorted cell, see, FIG. 7G. NTRK1+ cells were positive for both Substance P and CGRP indicating primarily a peptidergic nocicieptors phenotype (FIGS. 7H and I; day 30 of differentiation).

A primary functional hallmark of sensory neuron identity (i.e. function) is their electrophysiological signature (Fang, et al., *J Physiol* 565, 927-943, (2005), herein incorporated by reference). NTRK1+ sorted neurons were also tested by standard electrophysiology techniques for cultured neurons (Placantonakis, et al. Stem Cells. 2009, FIG. 5 has an example, herein incorporated in its entirety)

NTRK1+ cells exhibited a characteristic single action potential (AP), electrophysiological signature, firing pattern with an average membrane resting potential of 67±4 mV by day 21 after initial LSB3i treatment. The resulting AP timing and shape of action curve in LSB3i human neurons are shown in FIG. 7J, see thick red line) and Table 1 below. These results were similar to those described previously in electrophysiological reports of primary anaesthetized adult rat nociceptors (Fang, et al., *J Physiol* 565, 927-943, (2005), herein incorporated by reference).

TABLE 1

Electrophysiology of human LSB3i Cultured Cells compared to rat nociceptive and non-nociceptive dorsal root ganglion neurones in vivo.

| Action Potential | LSB3i Cells | Nociceptor Cells* | Mechanoreceptor Cells* |
|---|---|---|---|
| Duration at base (milli-second; ms) | 9.5 | 6 | 2 |
| Rise time (milli-second; ms) | 3.8 | 2 | 0.8 |
| Fall Time, Tussman and Misc. (milli-second; ms) | 5.8 | 3.5 | 1 |
| Overshoot (milli-volt; mV) | 29 | 22.5 | 5 |
| 80% Recovery (milli-second; ms) | 15.1 | 21 | 5 |

*Fang, et al., J Physiol 565.3: 927-943 (2005).

VI. Global Gene Expression Analysis Shows an Exemplary Timing of Gene Expression.

The following example describes using exemplary methods for determining global gene expression of nociceptor cells and other cells types produced by methods described herein.

Figure 10:
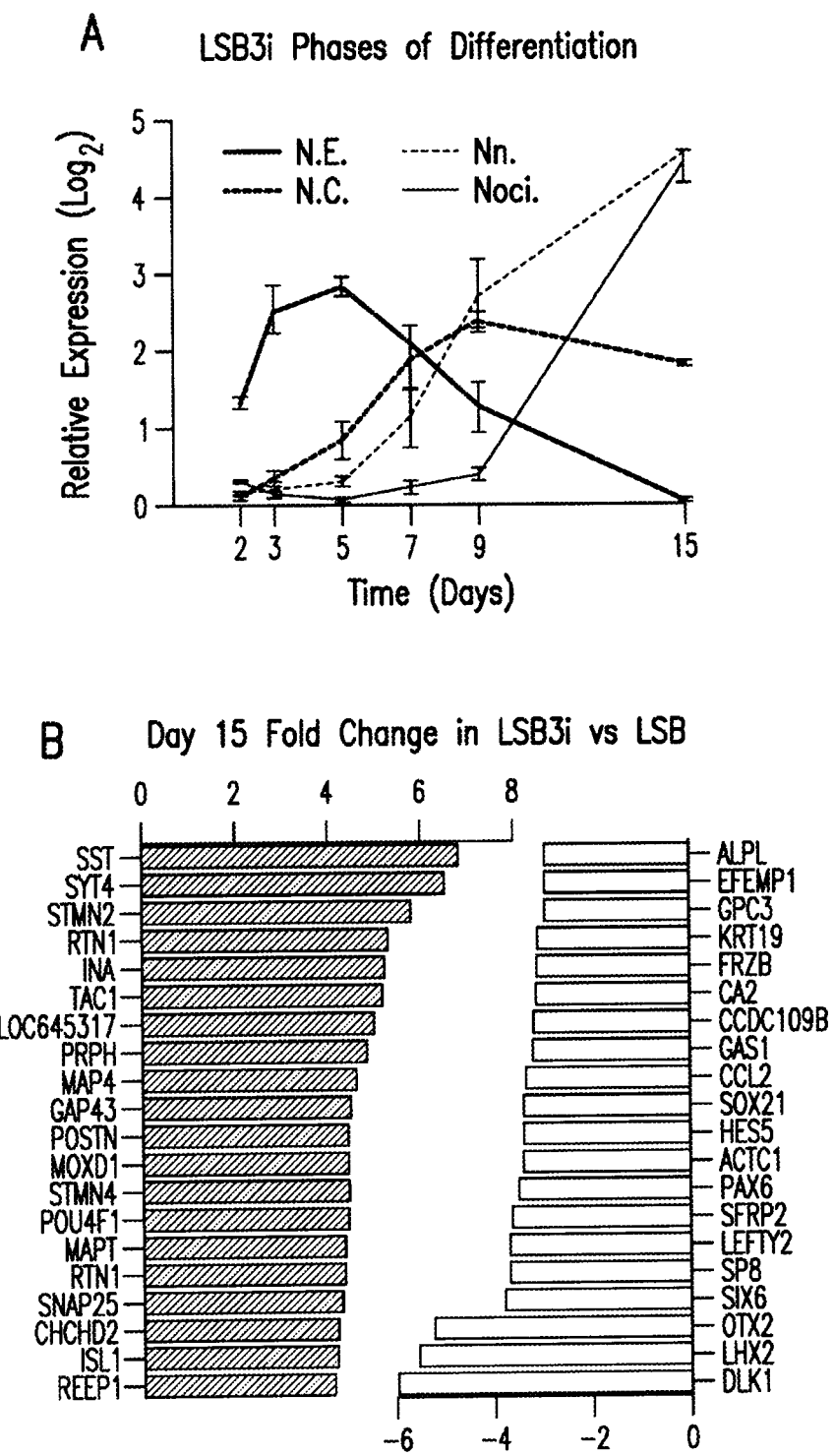
FIG. 10—Exemplary Gene expression of LSB3i nociceptors—Gene expression analysis was performed on days 2, 3, 5, 7, 9, and 15 for both LSB and LSB3i treated cells. (a) Distinct phases of differentiation are observed when examining markers for neuroectoderm, neural crest, neurons, and nociceptors (N.E., N.C., Nn., and Noci., respectively). (b) Top twenty significant up- and downregulated genes by fold change at day 15 for LSB3i were compared to LSB treated cells. (c) Expression of OCT4, DLK1, PAX6, SOX10, POU4F1 (BRN3A), ISL1, NEUROG2, NEUROG1, NTRK1, VGLUT2, TAC1, and TRPV1 are consistent with emergence of a peptidergic nociceptor.
Figure 10:
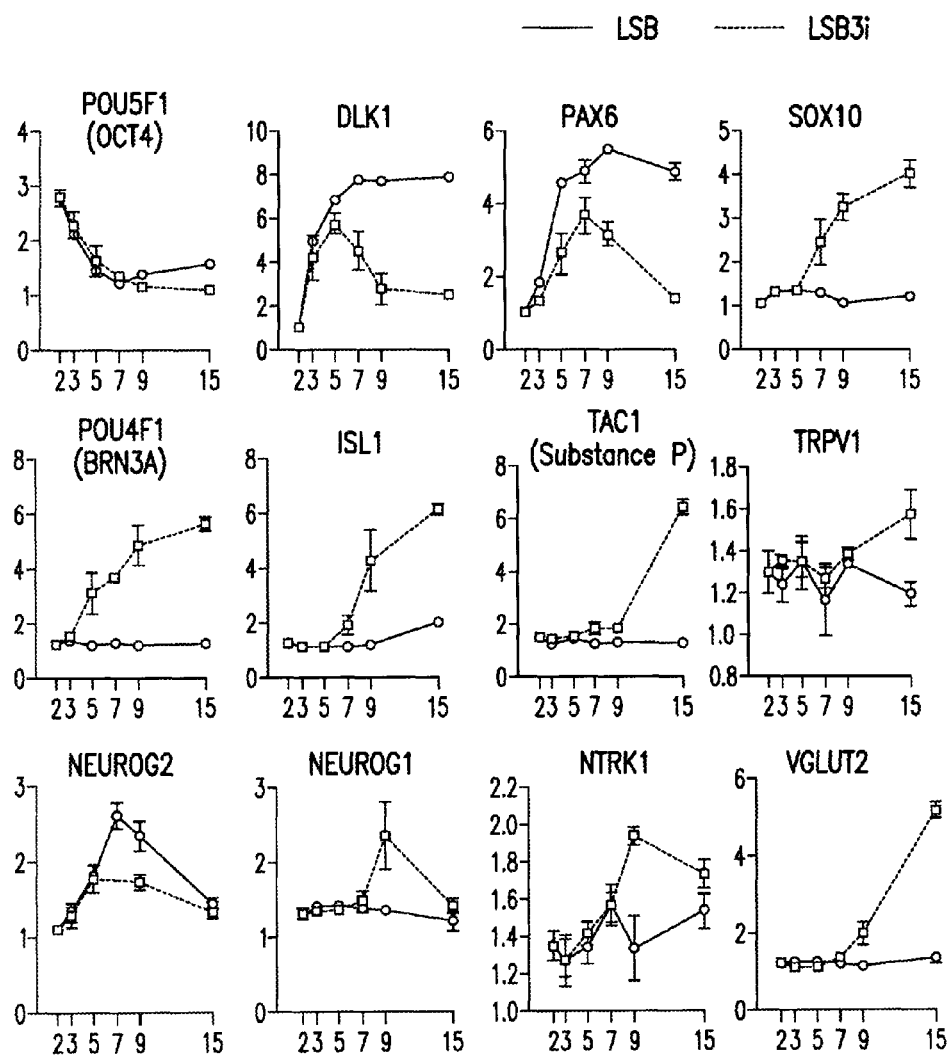
Figure 11:
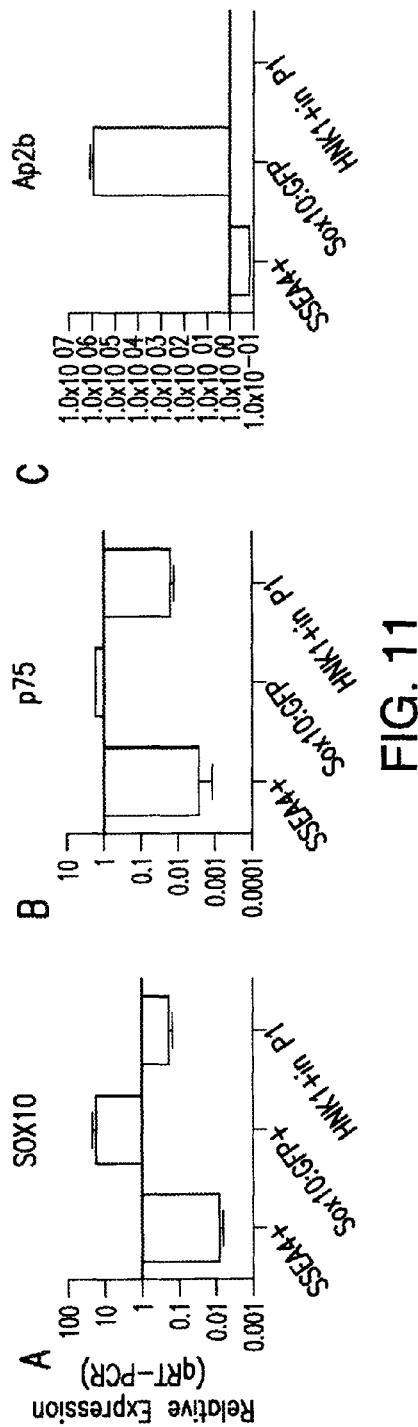
FIG. 11—Exemplary qRT-PCR validation of genes induced in a SOX10::GFP BAC cell line. Compared to hPSCs sorted for SSEA-4 and a previous method to enrich for neural crest stem cells by sorting for HNK1+ cells from neural cultures (Lee, et al., Nat Biotechnol 25, 1468-1475, herein incorporated by reference), GFP+ cells sorted using the SOX10::GFP BAC greatly enriched for cells expressing neural crest genes SOX10, p75, and AP2B as measured by qRT-PCR.

Global gene expression analysis was performed at fine temporal resolution (days 2, 3, 5, 7, 9, and 15, NCBI Gene Expression Omnibus (GEO) accession number GSE26867; for both LSB and LSB3i treated hPSCs to further characterize the timing of events (i.e. marker expression) during the induced differentiation process. When select markers for neuroectoderm, neural crest, neurons, and nociceptors were analyzed (see Table 2 below), distinct phases of differentiation for each could be observed (FIG. 10).

TABLE 2

Gene expression assigned to specific phases of differentiation during directed differentiation after contact with LSB-3i. See also, FIG. 10A.

| Phases of Differentiation | Genes Expressed |
|---|---|
| Neurectoderm | PAX6, OTX2, DLK1, DKK1, CUZD1 |
| Neural Crest | SOX10, MSX1, ID2, AP2B, ETS1, FOXD3 |
| Neuron | NGN1, DCX, TUBB3, SYT4, STMN2, INA, GAP43, ISL1, POU4F1 |
| Nociceptor | TAC1, VGLUT2, SLC15A3 |

This gene expression analysis (FIG. 10B,C and Table 2 above) was consistent with the majority of immunofluorescence results. For example, gene analysis showed that in maturing neurons, ISL1, POU4F1 (BRN3A), SOX10, TAC1 (pro-peptide to Substance P), NTRK1, and the glutamate vesicular transporter VGLUT2 genes were all upregulated (i.e. the number of cells in culture increased the expression of these markers over time). Concurrently while these markers were observed to be increased on induced cells, markers for hESC-derived primitive neuroectoderm were observed to be downregulated (i.e. expressed on fewer cells in culture), in particular DLK1, LHX2, OTX2, LEFTY2, PAX6, and HES5.

However, expression of somatostatin (SST) and SOX10 was found at day 15 in LSB3i treated cell cultures, which is expected to be expressed in mature nociceptors. However, SST was also shown expressed in developing sensory neurons. Therefore, the inventors contemplated that this marker was indicating the presence of immature cells at day 15. Though somewhat down-regulated, SOX10 expression was also observed at a time when most cells appeared to be neurons. This finding was unexpected since SOX10 was expected to be downregulated as the cells differentiate into neurons. This unexpected discovery of SST and SOX10 expression in cells of day 15 cultures was contemplated as not all of the become nociceptors cells, approximately 20-30%. This indicated that other mature cell types (such as Schwann cells) continue to express SOX10.

hESC-derived primitive neuroectoderm cell cultures produced by dual SMAD inhibition in Chambers, et al., Nat Biotechnol 27, (2009); Fasano, et al., Cell Stem Cell 6, 336-347, (2010), each of which are herein incorporated by reference), demonstrated high expression of DLK1, LHX2, OTX2, LEFTY2, PAX6, and HES5 genes. Likewise, similar high expression for these genes was observed when hESC-derived primitive neuroectoderm cell cultures were produced by dual SMAD inhibition using LSB (see FIG. 10B,C and Table 3 below). These genes were reduced during LSB3i treatment while producing nociceptors during the development of the present inventions.

TABLE 3

Timing of gene expression during directed differentiation with LSB-3i compared to LSB.

| LSB-3i Differentiation compared to LSB control | Genes upregulated | Genes downregulated |
|---|---|---|
| Day 7 | ISL1, POU4F1 (BRN3A), SOX10, NTRK1, and the glutamate vesicular transporter VGLUT2 | DLK1 |

TABLE 3-continued

Timing of gene expression during directed differentiation with LSB-3i compared to LSB.

| LSB-3i Differentiation compared to LSB control | Genes upregulated | Genes downregulated |
|---|---|---|
| Day 9 | ISL1, POU4F1 (BRN3A), SOX10, NTRK1, and the glutamate vesicular transporter VGLUT2 | DLK1 and PAX6 |
| Day 15 | ISL1, POU4F1 (BRN3A), SOX10, TAC1 (pro-peptide to Substance P), and the glutamate vesicular transporter VGLUT2 | DLK1, LHX2, OTX2, LEFTY2, PAX6, and HES5 |

In addition, the temporal transcriptome analysis provided further evidence for nociceptor intermediate cell fates, distinct from mechanoceptor cells and proprioceptor cells. The neurogenin basic helix-loop-helix proteins mediate two sequential waves of neurogenesis in the dorsal root ganglia during mouse development (Marmigere, et al., *Nat Rev Neurosci* 8, 114-127, (2007); Ma, et al., *Genes Dev* 13, 1717-1728 (1999), herein incorporated by reference). The first wave, marked by NEUROG2 (Neurogenin-2) gives rise to mechanoceptor cells and proprioceptor cells, and the second marked by NEUROG1 (Neurogenin-1) gives rise to nociceptor cells. When hPSCs are treated with LSB, NEUROG2 expression is strongly induced by day 7 (FIG. 10C and Table 4 below). In contrast, hPSCs treated with LSB3i show a less pronounced induction of NEUROG2 by day 7 but selective induction of NEUROG1 by day 9 (FIG. 10C).

TABLE 4

Timing of gene expression during directed differentiation with LSB-3i compared to LSB.

| neurogenin basic helix-loop-helix genes expressed in treated hPSCs | Day 7 | Day 9 |
|---|---|---|
| LSB-3i | No difference in NEUROG1 compared to LSB control cells No change in % of cells expressing NEUROG2 | NEUROG1 induction No change in % of cells expressing NEUROG2 |
| LSB control | No difference in NEUROG1 NEUROG2 induction | No difference in NEUROG1 Downregulation of NEUROG2 |

VII. Contemplated Large Scale Culture Using Compositions and Methods of the Present Inventions for Providing Exemplary Nociceptor Cells.

The following contemplated description shows exemplary methods and uses for large-scale production of nociceptor cells produced by methods described herein.

The scalable generation (i.e. methods contemplated to be successful for generating nociceptor cells from both cultures containing a relatively small number of cells, for example, $1.5 \times 10^4$ cells/well of 48 well plates such as described in Examples, supra), and contemplated $5 \times 10^3$ cells/well in 96 well plate, up to large batch cultures of hPSC derived nociceptors, (for example, $1 \times 10^7$-$1 \times 10^8$ cells in batches of 18 15 cm dishes (approximately $5.5 \times 10^7$ cells), using LSB3i. These methods are contemplated to provide hPSC derived nociceptor cells for use in testing compounds for use in basic biology studies and for drug discovery applicable to medical applications in humans and animals. In particular, the inventors' contemplate the use of compositions and methods of the present inventions for treatments to reduce acute and chronic pain in humans and animals.

In particular, large batch cultures are contemplated wherein exemplary $1 \times 10^8$-$1 \times 10^9$ hPSC cells are grown in batch embryoid body cultures using culture medium and exemplary compounds as described herein for providing exemplary nociceptor cells, for example, peptidergic nociceptor cells, in exemplary nonlimiting ranges of $7 \times 10^7$-$7 \times 10^8$ (wherein a 70% efficiency of nociceptor cell harvest is contemplated). Exemplary nociceptor cells are contemplated to express genes (i.e. mRNA and protein) identifying nociceptor cells, such as TAC1, VGLUT2, and SLC15A3. Exemplary nociceptor cells are contemplated to express identification markers, such as ISL1, BRN3A, RET, RUNX1, Substance P, CGRP, etc.

In summary, the inventors' contemplate using compositions and methods of the present inventions to provide novel platforms in basic biology and drug discovery for the study and treatment of conditions associated with nociceptor cells, in particular pain, in humans and animals.

VIII. Derivation of Melanocytes from Human Pluripotent Stem Cells: LSB-MeI. LDN-193189, SB431542, CHIR99021, EDNR3 and BMP Melanocytes are pigment-producing cells found predominantly in the epidermis where they establish a photo-protective barrier against UV-irradiation induced DNA damage. Defects in melanocyte biology are associated with a number of pigmentation disorders including albinism, vitiligo, and piebaldism. Melanocytes are the cell-of-origin for malignant melanoma. However, understanding/treatment of these disorders is limited by the lack of experimental systems suitable for the study of human melanocytes in vitro.

During the development of the present inventions, a protocol was discovered that caused the rapid and highly efficient differentiation of human pluripotent cells into both neural cell precursors and neural crest (NC) precursors. Because skin melanocytes derive from neural crest cell precursors, the inventors discovered ways to use LSB-C derived neural crest cell lineage cells in order to direct differentiation along the melanocyte lineage into mature melanocytes.

In other words, pluripotent ESCs (embryonic stem cells) were induced to become neural crest precursor cells (LSB-C) which were induced to become melanocyte progenitors then induced to become differentiated melanocytes. This progression was modeled as a progressive specification along the melanocytic lineage, from pluripotent ESCs through neural crest precursor, towards more committed melanocyte progenitors before establishing a terminally differentiated state (see, schematic which shows an exemplary markers for each of these stages in FIG. 16). The inventors contemplate the use of these directed differentiated melanocytes in novel assays for identifying molecular mechanisms of melanocyte development. In particular, the inventors contemplate assays that use these directed differentiated melanocytes in combination with a recently established approach for deriving patient-specific induced pluripotent stem cells (iPSCs). This novel directed differentiated melanocytes are contemplated to generate assays for melanocyte-related models of human disease, such as including albinism, vitiligo, piebaldism, melanoma, and malignant melanoma, etc.

A. Derivation of Neural Crest from Human ESCs (a First Step in Directed Differentiation for Producing Melanocytes).

Melanocytes arise from a transient, migratory population of cells unique to vertebrates known as the neural crest (NC) that arises during gastrulaion at the border between the neural and non-neural ectoderm. The multipotent neural crest differentiates into an extensive range of derivatives determined, in part, by the anatomic location (axial level) of the NC cell.

Considerable evidence in the literature identified Wnt, BMP, and TGF-β signaling as key requirements in early neural crest specification. Of these, the two latter pathways are actively inhibited by the small molecule treatment of a dual SMAD inhibition protocol. As described herein, the inventors discovered that BMP and TGF-β signaling were optimized for neural crest induction through early withdrawal of their respective inhibitors. Further, as described herein, the use of a small molecule GSK3β inhibitor (CHIR99021) which in turn activated Wnt signaling was discovered to produce populations expressing neural crest stem cell markers when added to LSB treated cells at Day 2 of treatment. Thus a modified dual SMAD inhibition protocol combining optimized signaling for all three pathways was used on the Sox10::GFP cell line and found to enhance the induction of Sox10::GFP expressing neural crest to 65% of the population (LSB-C treatment).

B. Lineage Specification and Isolation of Neural Crest-Derived Melanoblasts.

The Sox10:: GFP expressing NC derived with LSB-C was then tested for competency to differentiate along the melanocyte lineage. Through the identification of cells co-expressing Sox10::GFP and MITF, a marker expressed in but not unique to the melanocyte lineage, the presence of putative melanocyte precursors was confirmed at day 11 of the modified differentiation protocol (LSB-C) (FIG. 13A).

A cell surface marker was needed that would allow identification of melanocyte lineages in order to further optimize the induction of these cell populations and subsequently isolate or purify specific types of melanocyte precursors. After a literature search, c-kit was identified as a candidate marker for presumptive melanocyte precursors. Markers for c-kit tested on the Sox10::GFP+ cells confirmed the presence of a low percentage (approximately 9%) of Sox10::GFP/c-kit co-expressing cells (FIG. 13B) that greatly enriched for the expression of early melanocyte markers (FIG. 13C). Further optimization of the differentiation protocol revealed that the abundance of Sox10::GFP/c-kit double positive cells were increased nearly four-fold through additional treatment with BMP4 and Endothelin-3 (LSB-MeI, FIG. 13D-E), two factors implicated in melanocyte specification.

C. Expansion and Maturation of Melanocytes.

The inventors discovered that presumptive melanocyte precursors can be matured to a pigmented state following as little as six additional days in culture post-sort (FIG. 14A-B). Surprisingly, the inventors' observed that both Sox10::GFP/c-kit double positive and single positive populations for each of the two markers gave rise to pigmented cells, although with different kinetics (FIG. 14C), indicating a lineage hierarchy between the three populations (cKit+/SOX10−, cKit−/SOX10+, cKit+/SOX10+). The identification of these 3 melanocyte lineage cells was contemplated to allow the isolation of differentiation intermediates along the melanocyte lineage.

With the use of these melanocyte precursor cells the optimal maturation conditions capable of inducing and supporting cells which possess mature melanocyte phenotypes was identified using a large number of compounds contemplated to support such maturation. Melanocyte characteristics evaluated included induction of spindle morphology, pigmentation, and melanosome formation.

The inventors discovered that addition of BMP4 and cAMP to the culture medium promoted a mature spindle-like morphology and pigmentation (FIG. 14D). Pure cultures of melanocytes were obtained when cells were propagated for eight weeks (long-term) in culture media containing SCF, EDN3, FGF, Wnt (CHIR), BMP4, and cAMP on the basis of expression of the mature melanocyte markers MITF, SOX10, Tyrp1, and HMB45 (FIG. 15A). A dark pellet was observed when long-term LSB-MEL cells were centrifuged to estimate pigment concentration (FIG. 15B). Electron microscopic ultrastructural characterization of mature melanocytes revealed the presence of numerous darkly pigmented melanosomes in the cytoplasm of LSB-MeI derived melanocytes (FIG. 15C) at various developmental stages (FIG. 15D).

D. Melanocytes are Derived from Human Pluripotent Stem Cells: LSB-Melanocytes (LSB-MeI).

The following describes exemplary compositions and methods for providing melanocytes for use in related disease modeling.

Figure 14:
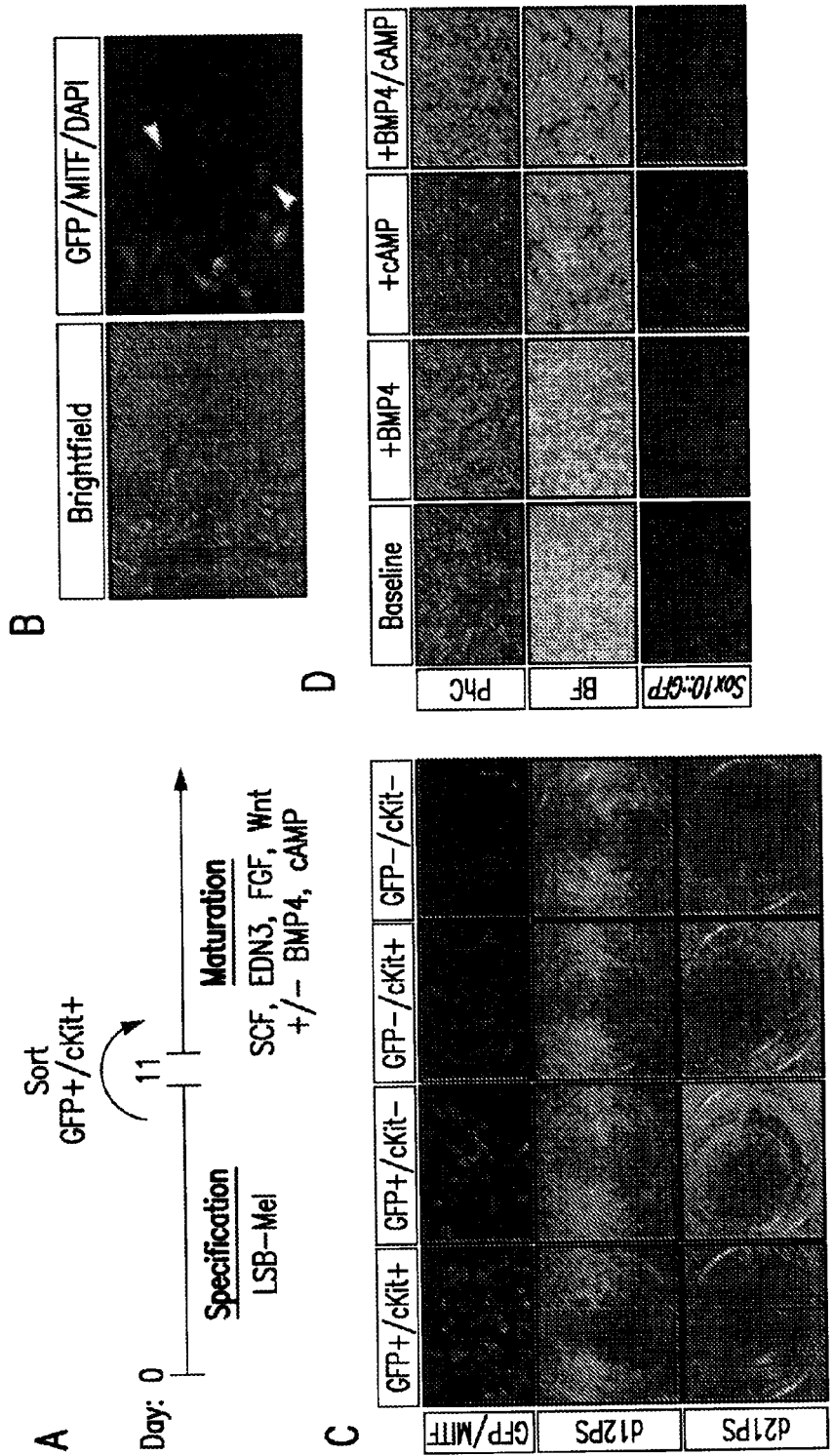
FIG. 14—Exemplary Expansion and Maturation of Melanocyte Precursors—Summary of differentiation conditions (A). Following specification in LSB-C conditions with BMP4 and EDN3 (LSB-MeI) cells were sorted at day 11 and replated. Post-sort (PS) cells were maintained in maturation media containing c-kit ligand (SCF), endothelin 3 (EDN3), fibroblast growth factor (FGF), and CHIR. Pigmented cells observed by brightfield microscopy at day 6 PS were positive for the melanocyte marker MITF but appeared to have downregulated the Sox/0::GFP reporter (B). All populations except the Sox10::GFP, c-kit double negative eventually gave rise to MITF expressing cells and macroscopic pigmented clusters, but at differing rates (C). Treatment with BMP4 and cAMP enhanced the differentiation into pigmented cells exhibiting a spindle-like morphology typical of melanocytes (D).

A Sox10::GFP Bacterial Artificial Chromosome (BAC) human embryonic stem cell (hESC) reporter line was generated that allowed monitoring of neural crest cell induction in vitro as this cell line responds to contact with small molecules. Sox10 was the most robust early marker of multipotent neural crest stem cells and was also found expressed in some neural crest derivatives, including melanocyte progenitors. This reporter system was used to prospectively identify and isolate neural crest populations in the development of a directed differentiation scheme in order to produce melanocyte cultures with higher purity and numbers than obtained with previous maturation schemes (FIG. 14, LSB-C).

In a dual SMAD inhibition protocol (Chambers, et al. Nat. Biotech. (2009), herein incorporated by reference), human pluripotent stem cells (hPSCs) treated with two small molecules to inhibit SMAD signaling efficiently produced CNS neural tissues. Additionally when hESC was plated at lower densities, low levels of spontaneous neural crest cell induction was observed (for example, approximately 3% Sox10:: GFP+ neural crest type cells were observed). However, for use in research and for medical studies, larger numbers of neural crest type cells were needed. Further, for melanocyte research, a purer population with larger numbers of cells were necessary that were not provided with the low level spontaneous differentiation.

During the development of the present inventions the inventors discovered methods to optimize the dual SMAD inhibition protocol for neural crest induction in a manner that would produce highly pure yields of melanocyte precursors, maturing melanocytes and mature melanocytes.

Specifically, the following time line of culturing conditions was developed that produced melanocytes of the present inventions: Feed on Day 0 and 1 with LDN and SB (using the same concentration ranges as LDN and SB in methods comprising 3i); Feed on Day 2 with LDN, SB, CHIR (using the same concentration ranges as LDN, SB, and CHIR in methods comprising 3i as described herein); In one embodiment, Feed on Day 3 with SB, CHIR (using the same concentration ranges as SB and CHIR in methods comprising 3i as described herein), in another embodiment Feed on Day 3 with LDN, SB, CHIR (using the same concentration ranges as LDN, SB, and CHIR in methods comprising 3i as described herein); Feed on Day 4 and 5 CHIR (using the same concentration ranges as CHIR in methods comprising 3i as described herein); Feed on Day 6 to 11 CHIR, BMP4, and EDN3 (using the same concentration ranges as CHIR in methods comprising 3i as described herein, see concentration ranges below for BMP4 and EDN3). On day 11 cells were passaged and fed with MEL media (including CHIR) up to 8 weeks.

MEL media enriched for melanocytes such that by 8 weeks the cell cultures showed up to 100% of apure population. Thus this LSB-MEL method/protocol had a high efficiency of melanocyte production. The inventors also discovered during the development of melanocytes that Linoleic Acid was at least one required ingredient in the MEL medium (see, FIG. 16).

Figure 13:
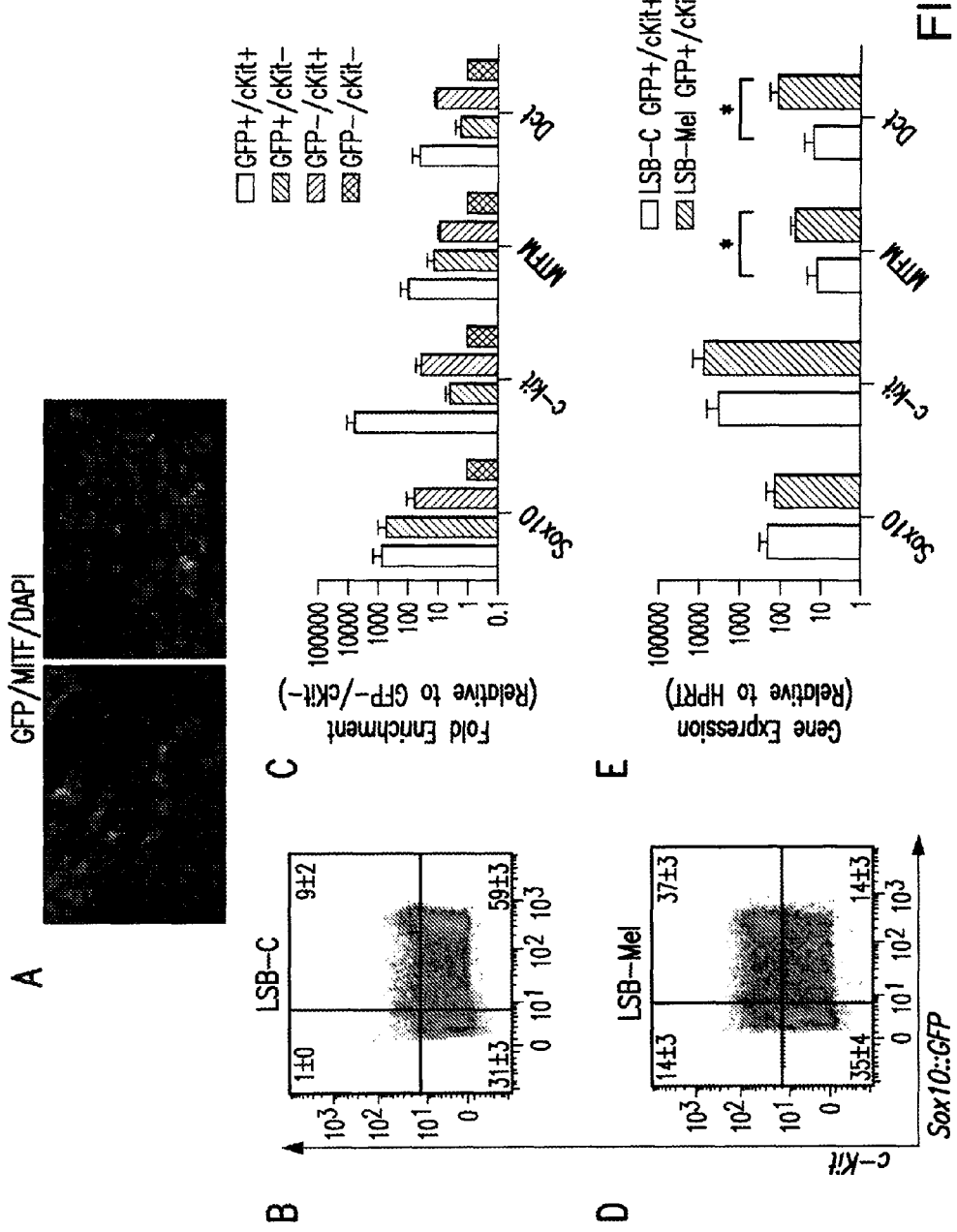
FIG. 13—Exemplary Specification and isolation of melanocyte progenitors/melanoblasts—The 11-day LSB-C protocol supported the derivation of Sox10::GFP, MITF co-expressing melanocyte progenitors (A, right panel). MITF single positive populations were also observed (A, left panel). c-Kit was identified as a potential marker of melanocyte progenitors. A low percentage of Sox10::GFP, c-kit co-expressing cells were observed after LSB-C differentiation (B). qRT-PCR analysis confirmed the enrichment of melanocyte markers MITFM and Dct in the double positive population (C). Treatment with BMP4 and EDN3 ("LSB-MeI") enhanced induction of the Sox10::GFP, c-kit double positive putative melanocyte progenitor population (D). Sox10:: GFP, c-kit double positive cells isolated following LSB-MeI treatment exhibited significantly higher levels of melanocyte markers MITFM and Dct (E). All error bars represent s.e.m. * p<0.05.

During the development of melanocytes, multiple precursor stages were observed in the following order: neural crest stem cell, embryonic glial-melanoblast stem cell, adult melanocyte stem cell, melanocyte, see, exemplary schematic in FIG. 13. FIG. 13. Specification and isolation of melanocyte progenitors/melanoblasts. The 11-day LSB-C protocol supported the derivation of Sox10::GFP, MITF co-expressing melanocyte progenitors (A, right panel). MITF single positive populations was observed (A, left panel). c-Kit was identified as a potential marker of melanocyte progenitors. A low percentage of Sox10::GFP, c-kit co-expressing cells were observed after LSB-C differentiation (B, orange population). qRT-PCR analysis confirmed the enrichment of melanocyte markers MITFM (a basic-helix-loop-helix-leucine zipper protein) and Dct (Dopachrome tautomerase (dopachrome delta-isomerase, tyrosine-related protein 2)) in the double positive population (C). Treatment with BMP4 and EDN3 ("LSB-Mel") enhanced induction of the Sox10::GFP, c-kit double positive putative melanocyte progenitor population (D). Sox10::GFP, c-kit double positive cells isolated following LSB-Mel treatment exhibited significantly higher levels of melanocyte markers MITFM and Dct (E). Error bars represent s.e.m. * $p<0.05$.

FIG. 14. Expansion and Maturation of Melanocyte Precursors.

Summary of differentiation conditions (A). Following specification in LSB-C conditions with BMP4 and EDN3 (LSB-Mel) cells were sorted at day 11 and replated. Post-sort (PS) cells were maintained in maturation media containing c-kit ligand (SCF), endothelin 3 (EDN3), fibroblast growth factor (FGF), and Wnt activators. Pigmented cells observed by brightfield microscopy at day 6 PS were positive for the melanocyte marker MITF but appeared to have downregulated the Sox10::GFP reporter (B). All populations except the Sox10::GFP, c-kit double negative eventually gave rise to MITF expressing cells and macroscopic pigmented clusters, but at differing rates (C). Treatment with BMP4 and cAMP enhanced the differentiation into pigmented cells exhibiting a spindle-like morphology typical of melanocytes (D).

Figure 15:
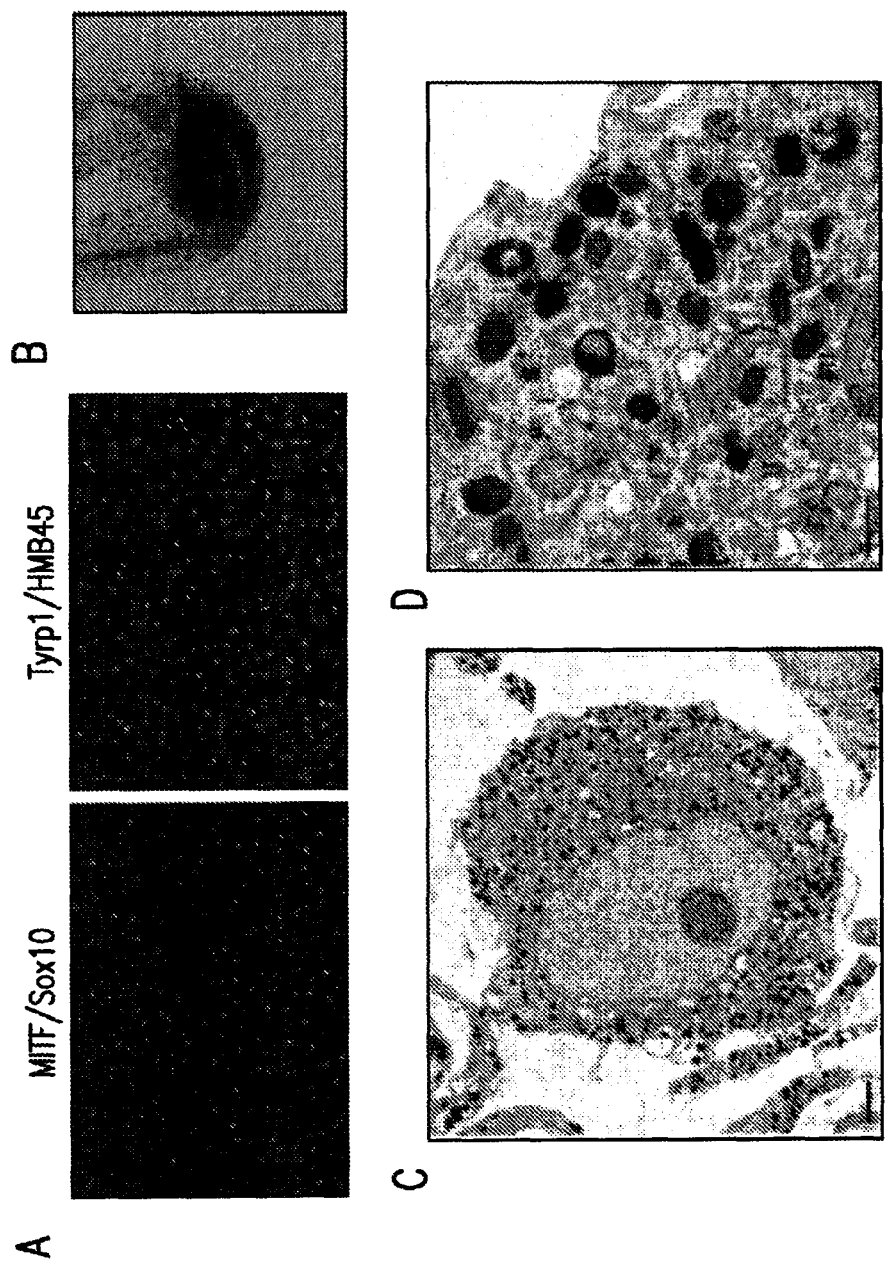
FIG. 15—Exemplary Characterization of Mature Melanocytes—Pure populations of mature melanocytes derived with the LSB-MeI protocol maintain the expression of common melanocyte markers including MITF, Sox10, Tyrp1, and HMB45 after greater than 8 weeks in culture (A). Melanocytes retain their darkly pigmented phenotype over several weeks in passage (B). $1 \times 10^6$ cells were pelleted and photographed to assess pigmentation levels. Electron microscopic ultrastructural characterization of mature melanocytes (C, D). The presence of numerous darkly pigmented melanosomes in the cytoplasm of LSB-MeI derived melanocytes can be observed by TEM (C). Note the presence and progressive deposition of melanin pigment with the maturation of melanosome vesicles from stages I through IV (D).

FIG. 15. Characterization of Mature Melanocytes.

Pure populations of mature melanocytes derived with the LSB-Mel protocol maintain the expression of common melanocyte markers including MITF, Sox10, Tyrp1 (Tyrosinase-related protein 1), and HMB45 after greater than 8 weeks in culture (A). Melanocytes retain their darkly pigmented phenotype over several weeks in passage (B). $1\times10^6$ cells were pelleted and photographed to assess pigmentation levels. Electron microscopic ultrastructural characterization of mature melanocytes (C, D). The presence of numerous darkly pigmented melanosomes in the cytoplasm of LSB-Mel derived melanocytes were observed by TEM (C). Note the presence and progressive deposition of melanin pigment with the maturation of melanosome vesicles from stages I through IV (D).

Therefore, the inventors demonstrated that a dual SMAD inhibition protocol, LSB, rapidly and efficiently generated Sox10:: GFP expressing neural crest populations from human embryonic stem cells. This modified protocol supported the induction of low levels of melanocyte progenitors, which were prospectively identified and isolated by c-kit expression. Induction of these cells was further enhanced through treatment with BMP4 and EDN3. Melanocyte progenitors were subsequently matured to a pigmented state following additional culture in vitro in the presence of BMP4 and cAMP.

Cell Medium for LSB-MEL:

| Mel-1 Media: | | |
|---|---|---|
| NeuroBasal | Invitrogen 21103049 | 50% |
| DMEM Low Glucose | Invitrogen 11885 | 30% |
| MCDB201 | Sigma M6770 | 20% |
| B27 | Invitrogen 17504-044 | 2% |
| ITS | Sigma I314 | 1% |
| Linoleic Acid-BSA | Sigma L9530 | 1% |
| L-glut | Gibco 25030-164 | 250 nM |
| Dexamethasone | Sigma D2915 | 0.05 uM |
| Cholera Toxin | Sigma C8052 | 50 ng/ml |
| L-AA | Sigma A5960 | 100 uM |
| SCF | Peprotech 300-07 | 50 ng/ml |
| EDN3 | American Peptide Company 88-5-10B | 100 nM |
| FGF2 | R&D 233-FB-001MG/CF | 4 ng/ml |
| cAMP | Sigma D-0260 | 500 uM |
| BMP4 | R&D 314-bp | 25 ng/ml |
| Chir | Stemgent 04-0004 | 3 uM |
| Day 6-11: | | |
| BMP4 | R&D 314-bp | 25 ng/ml |
| EDN3 | American Peptide Company 88-5-10B | 100 nM |

Concentration ranges for BMP4 from R&D: used between 10 ng/ml to 100 ng/ml (in one embodiment at 25 ng/ml), and EDN from American Peptide Company is used at 25-300 nM (in one embodiment at 100 nM).

Figure 16:
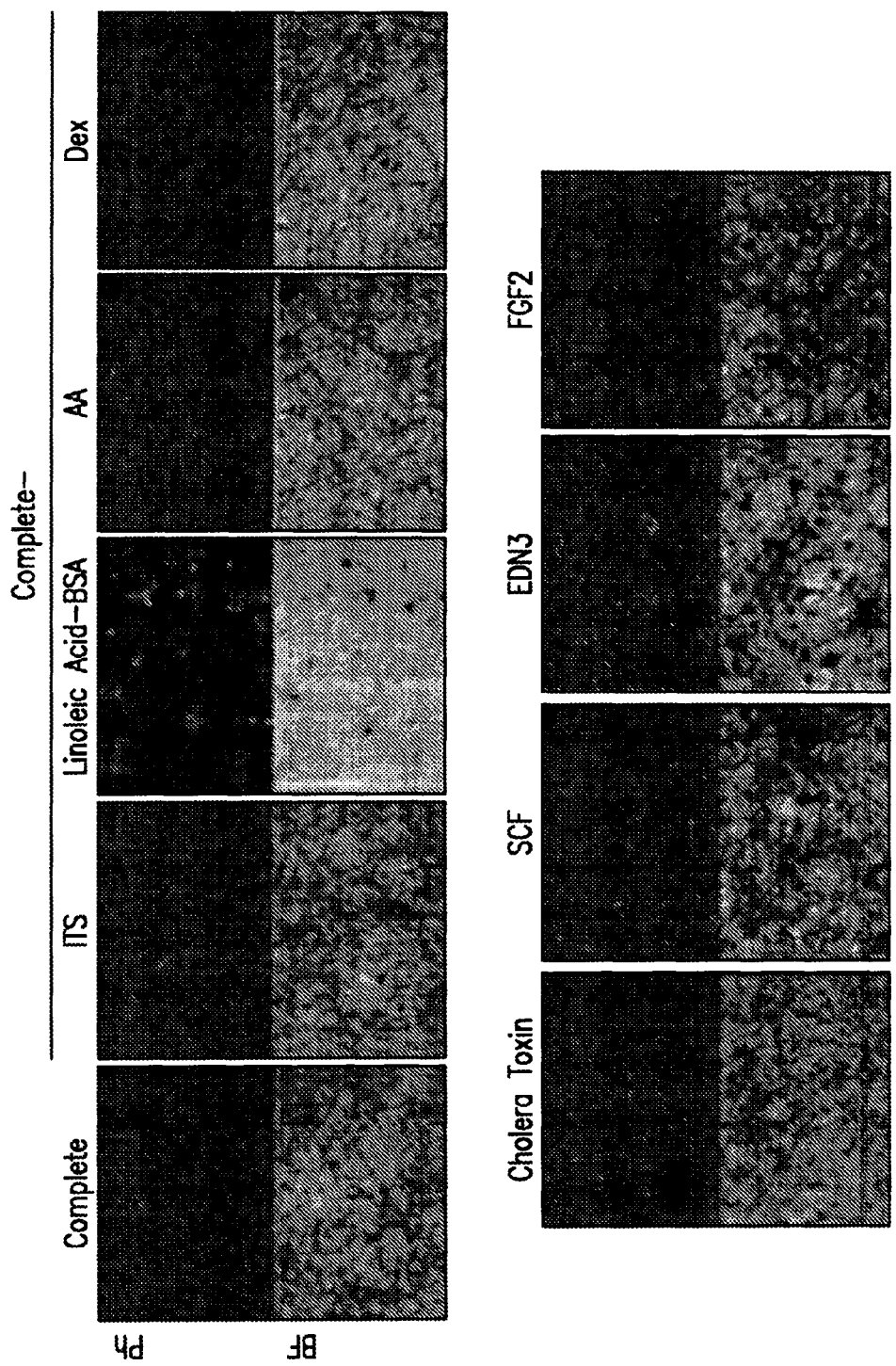
FIG. 16—Shows an exemplary LSB-MEL medium formulation required Linoleic Acid for growth of melanocytes and schematic of a melanocyte lineage. Medium component shown above microscopic views represent the medium component left out of the formulation; Ph=phase contrast; BF=bright filed. An exemplary schematic shows melanocyte progenitor markers used for identifying cells of a melanocyte lineage developed during the present inventions.
Figure 16:
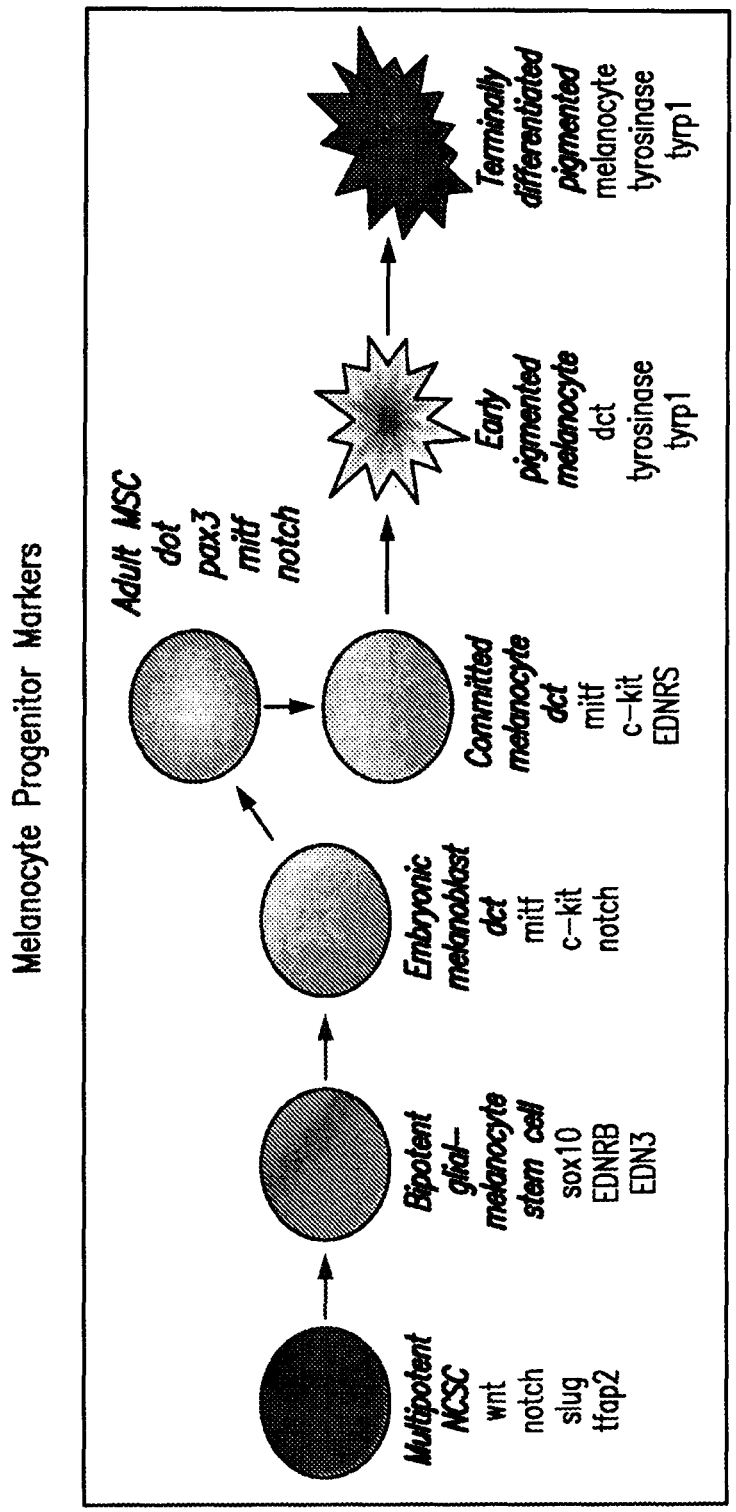
Figure 17:
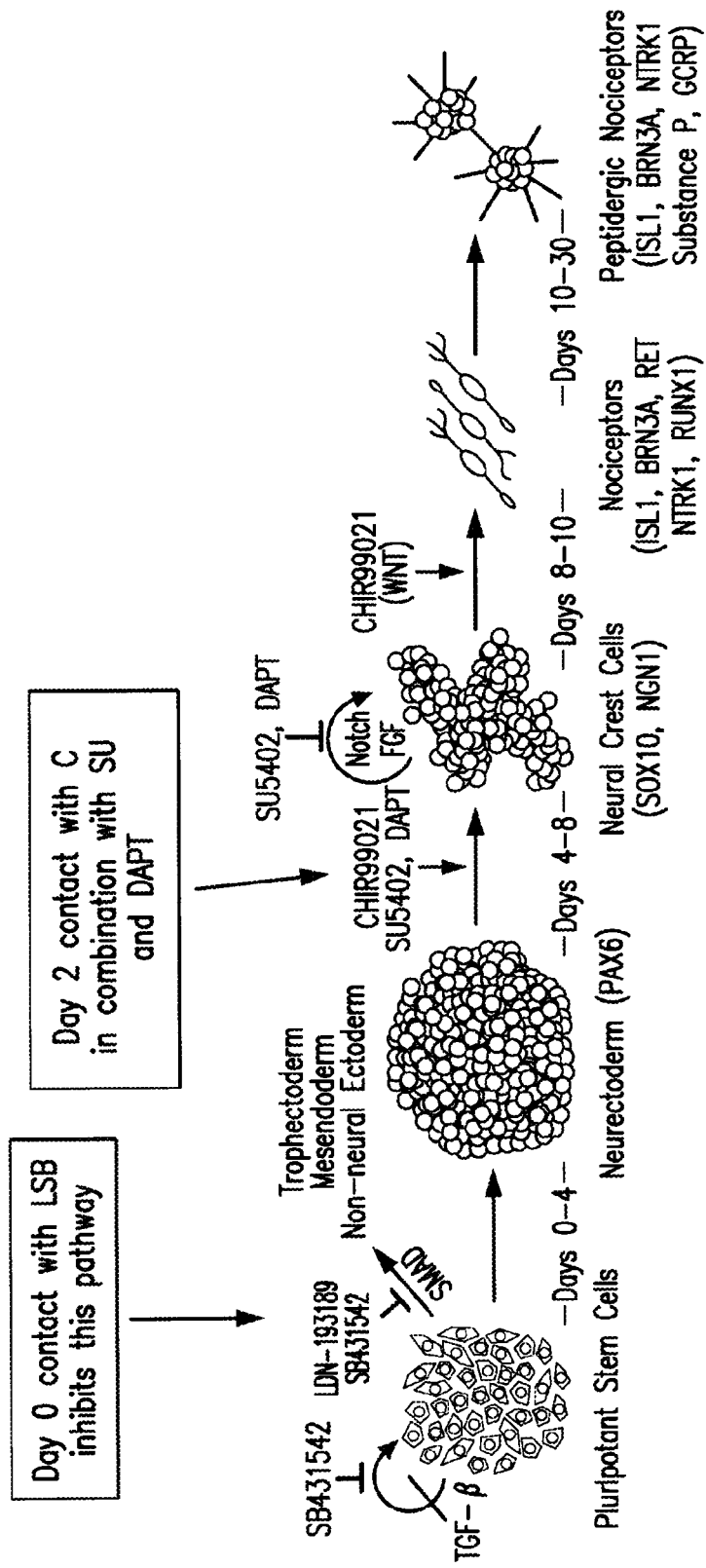
FIG. 17—Exemplary Differentiation model—Early LSB treatment of pluripotent embryonic human stem cells inhibited trophectoderm, mesendodenn, and non-neural ectoderm cell fates yielding cells with a neuroectoderm fate. The addition of CHIR99021, SU5402 and DAPT (3i) on day 2 after the initial LSB treatment induced and accelerated (over LSB-C and LSB treatment) neural crest stem cell identity markers by day 8 and promoted rapid differentiation of the neural crest stem cells into peptidergic nociceptors by day 10.

FIG. 16. Shows an exemplary LSB-MEL medium formulation that required Linoleic Acid for growth of melanocytes. Medium component shown above microscopic views represent the medium component left out of the formulation; Ph=phase contrast; BF=bright filed. An exemplary schematic shows melanocyte progenitor markers used for identifying cells of the present inventions.

Thus the inventors discovered and developed a rapid and defined protocol for the induction of neural crest in vitro. Further, the inventors used this rapid and defined protocol for the induction of neural crest cells in vitro for developing compositions and methods for directed differentiation of these cells into melanocytes. These melanocytes were unique in their capability for long-term culture and continuous production of eumelanin.

Therefore the derivation of melanocytes from human embryonic stem cells (hESCs) is contemplated to provide a valuable tool for further investigations into melanocyte disease biology.

EXPERIMENTAL

The following examples serve to illustrate certain embodiments and aspects of the present invention and are not to be construed as limiting the scope thereof. In the experimental disclosures which follow, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); pg (picograms); L and (liters); ml (milliliters); µl (microliters); cm (centimeters); mm (millimeters); µm (micrometers); nm (nanometers); U (units); min (minute); s and sec (second); deg (degree); pen (penicillin); strep (streptomycin) and ° C. 10 (degrees Centigrade/Celsius).

The following formulations describe exemplary cell culture medium for use in developing embodiments of the present inventions.

hESC Medium for Maintenance (1 Liter): 800 mL DMEM/F12, 200 mL of Knockout Serum Replacement, 5 mL of 200 mM L-Glutamine, 5 mL of Pen/Strep, 10 mL of 10 mM MEM minimum non-essential amino 15 acids solution, 55 µM of 13-mercaptoethanol, and bFGF (final concentration is 4 ng/mL).

KSR Medium for hESC Differentiation (1 liter): 820 mL of Knock out DMEM, 150 mL of Knock out Serum Replacement, 10 mL of 200 mM L-Glutamine, 10 mL of Pen/Strep, 10 mL of 10 mM MEM, and 55 µM of 13-mercaptoethanol.

N2 Medium for hESC Differentiation (1 liter): 985 ml dist. $H_2O$ with DMEM/F12 powder, 1.55 g of glucose (Sigma, cat. no. G7021), 2.00 g of sodium bicarbonate (Sigma, cat. no. S5761), putrescine (100 uL aliquot of 1.61 g dissolved in 100 mL of distilled water; Sigma, cat. no. P5780), progesterone (20 uL aliquot of 0.032 g dissolved in 100 mL 100% ethanol; Sigma, cat. no. P8783), sodium selenite (60 uL aliquot of 0.5 mM solution in distilled water; Bioshop Canada, cat. no. SEL888), and 100 mg of transferrin (Celliance/Millipore, cat. no. 4452-01), and 25 mg of insulin (Sigma, cat. no. 16634) in 10 mL of 5 mM NaOH.

Dulbecco's Modification of Eagles Medium (DMEM), with 10% FBS for Preparing PMEF ((Primary Mouse Embryo Fibroblast (PMEF)) Feeder Cells)

(1 liter): 885 mL of DMEM, 100 mL of FBS, 10 mL of Pen/Strep, and 5 mL of L-Glutamine.

Alpha Minimum Essential Medium (MEM) with 10% FBS for Preparing MS-5 Feeder Cell Medium (1 liter): 890 mL of Alpha MEM, 100 mL of FBS, 10 mL of Pen/Strep Gelatin solution (500 ml): Dissolve 0.5 g of gelatin in 500 ml of warm (50-60° C.) Milli-Q water. Cool to room temperature.

Example I

Materials And Methods

The following examples describe exemplary materials and methods used during the development of the present inventions.

Cells and Culture Conditions.

Human embryonic stem cell (hESC) cell (WA-09; passages 32-50) and hiPSC lines (C14, C72; passages 10-20) were cultured with mouse embryonic fibroblasts (MEFs, Globalstem, Rockville, State of Maryland, United States of America (USA)) pre-plated at 12-15,000 cells/$cm^2$. Human induced pluripotent stem cell (hiPSC) lines were generated as reported (Papapetrou, et al., *Proc Natl Acad Sci USA* 106, (2009), herein incorporated by reference). Medium containing Dulbecco's Modified Eagle Medium (DMEM)/F12, 20% knockout serum replacement, 1 mM L-glutamine (Invitrogen, Carlsbad, State of California, USA), 100 µM MEM non-essential amino acids (Invitrogen), and 0.1 mM β-mercaptoethanol (Invitrogen) was made. 6 ng/ml Fibroblast growth factor 2 (FGF-2, R&D Systems, Minneapolis, State of Minnesota) was added after sterile filtration and cells were fed daily and passaged weekly using 6 U/mL dispase (Worthington Biochemical, Lakewood, State of New Jersey, USA). The SOX10::GFP bacterial artificial chromosome cell line was generated as reported (Placantonakis, et al., *Stem Cells* 27, 521-532, (2009), herein incorporated by reference).

Neural and Nociceptor Induction.

Neural induction was performed as previously reported (Chambers, et al., *Nat Biotechnol* 27, (2009), herein incorporated by reference). Briefly, cells were collected then rendered to a single cell suspension using ACCUTASE (Sigma-Aldrich Corp. St. Louis, Mo., USA) and plated on gelatin for 30 minutes to remove Mouse Embryonic Fibroblast (MEF) Feeder Cells (MEFs) (MEFs adhere to gelatin coated plate). Non-adherent cells were collected and plated on matrigel treated dishes at a density of 20-40,000 cells/$cm^2$ in the presence of MEF-conditioned hESC media containing 10 ng/ml FGF-2 and 10 µM Y-27632 (rho-kinase inhibitor—Tocris Bioscience). Neural differentiation was initiated when the cells were confluent using Knockout Serum Replacement (KSR) media containing 820 ml of Knockout DMEM, 150 ml Knockout Serum Replacement, 1 mM L-glutamine, 100 µM MEM non-essential amino acids, and 0.1 mM β-mercaptoethanol. To inhibit SMAD signaling, 100 nM LDN-193189 and 10 µM SB431542 were added daily from day 0 (when SMAD signaling inhibitors LSB were added) through day 5. Cells were fed daily (i.e. 6 feedings with inhibitors, D0, D1, D2, D3, D4 and D5), and N2 media was added to the initial medium in increasing 25% increments every other day starting on day 4 (up to 100% N2 on day 10). Nociceptor induction was initiated by the addition of the three inhibitors (unless otherwise indicated) at 3 µM CHIR99021, 10 µM SU5402, and 10 DAPT daily from days 2 through 10. After day 10, long-term culture media consisted of N2 media containing 10-100 ng/ml human-β-nerve growth factor (NGF), 10-100 ng/ml brain-derived neurotrophic factor (BDNF), and 10-100 ng/ml glial cell-derived neurotrophic factor (GDNF).

Microscopy, Antibodies, and Flow Cytometry (FACS).

Cells were fixed with 4% paraformaldehyde for 20 minutes, washed with phosphate buffered saline (PBS), permeablized using 0.5% Triton X in PBS, and blocked using 1% BSA (bovine serum albumin) in phosphate buffered saline (PBS). For glutamate staining, 0.05% gluteraldehyde was added to the fixative. Primary antibodies used for microscopy included PAX6; Paired box gene 6 (aniridia, keratitis) (Covance, Princeton, N.J., USA), TUJ1; Neuron-specific class III beta-tubulin (Covance, Princeton, N.J., USA), Ki67; Antigen KI-67; MKI67 (Sigma-Aldrich Corp. St. Louis, Mo., USA), ISL1 (Developmental Studies Hybridoma Bank; DSHB), BRN3A; Brain-specific homeobox/POU domain protein 3A (Chemicon, Billerica, Mass., USA), RET; Proto-oncogene Tyrosine-protein Kinase Receptor (R&D), RUNX1; Runt-related transcription factor 1 (Sigma-Aldrich Corp. St. Louis, Mo., USA), MAP2; Microtubule-associated protein 2 (Sigma-Aldrich Corp. St. Louis, Mo., United States of America), TRPV1; transient receptor potential cation channel subfamily V member 1 (Neuromics Inc., Minneapolis, United States of America), Substance P (Neuromics Inc., Minneapolis, United States of America), CGRP; Calcitonin gene related peptide (Neuromics Inc., Minneapolis, United States of America). For flow cytometry, cells were fixed using the BD Cytofix/Cytoperm Kit (BD Biosciences Pharmingen), in one embodiment cells were additionally fixed in 4% paraformaldehyde. Primary conjugated antibodies for flow cytometry were NTRK1 (neurotrophic tyrosine kinase, receptor, type 1)-APC (R&D Systems, Inc., Minneapolis, Minn., USA), Nestin-Alexa647 (BD Biosciences Pharmingen, San Diego, Calif., USA), TUJ1-Alexa488 (BD Biosciences Pharmingen, San Diego, Calif., USA).
Electrophysiology.

Neurotrophic tyrosine kinase, receptor, type 1 (NTRK1)+ sorted cells were plated on polyornithine/laminin/fibronectin treated glass cover slips on days 10-12 and allowed to mature for an additional 3 weeks in long term culture media. Cover slips were transferred to an artificial cerebral spinal fluid containing (in mM): 125 NaCl, 2.5 KCl, 1.25 $KH_2PO_4$, 1 $MgCl_2$, 2 $CaCl_2$, 25 $NaHCO_3$, 1.3 ascorbate, 2.4 pyruvate, and 25 glucose, bubbled with 95% $O_2$ and 5% $CO_2$) at room temperature. An infrared-Differential Interference Contrast (DIC) microscope (Olympus) equipped with epifluorescence illumination, a charge coupled device camera, and two water immersion lenses (×10 and ×60) were used to visualize and target recording electrodes to the cells. The glass recording electrodes (7-9 MΩ resistance) were filled with an intracellular solution consisting (in mM, pH 7.25) of 130 mM potassium gluconate, 16 mM KCl, 2 mM $MgCl_2$, 0.2 mM EGTA, 10 mM HEPES, 4 mM $Na_2ATP$, 0.4 mM $Na_3GTP$, and 0.2% Alexa-568. Action potential properties at threshold currents were determined from cell recordings after application of an increasing series of 300-ms current steps of 25 pA. Recordings were collected and analyzed using Axopatch 700B amplifier and pCLAMP10 software (Molecular Devices, Sunnyvale, Calif., United States).
Gene Expression Profiling.

Total RNA was isolated at days 2, 3, 5, 7, 9, and 15 of differentiation of LSB or LSB3i treated hPSCs using Trizol LS. Samples were processed by the Memorial Sloan-Kettering Cancer Center (MSKCC) Genomics Core Facility and hybridized to the Illumina Human HT-12 v4 Expression BeadChip. Normalization and model-based expression measurements were calculated using the Illumina analysis package (LUMI) from the Bioconductor project (www.bioconductor.org) with in the statistical programming language R (http://cran.r-project.org/). Expression values are $log_2$ of the fold change. Pair-wise comparison cut-off was significant if the multiple test corrected p-value was <0.05.
Quantitative Real-Time PCR.

Total RNA was extracted using an RNeasy kit (Qiagen). For each sample, 1 μg of total RNA was treated for DNA contamination and reverse transcribed using the Quantitect RT kit (Qiagen). Amplified material was detected using Quantitect SYBR green probes and PCR kit (Qiagen) on a Mastercycler RealPlex2 (Eppendorf). All results were normalized to a HPRT control and are from 4-6 technical replicates of 2-3 independent biological samples at each data point.

Example II

Contacting Human Pluripotent Stem Cells with SB431542 and LDN-193189 (LSB) Produced Neural Lineage Cells The following example describes exemplary methods for providing cells of a neural lineage for use during development of the present inventions.

Dual SMAD inhibition was previously used as a rapid and highly effective method for inducing one type of neural lineage cells from hPSCs (Chambers, et al., *Nat Biotechnol* 27, (2009), herein incorporated by reference). These neural lineage cells induced by molecules including Noggin, had a default pathway that allowed development into central nervous system cells, i.e. neural cell fate. Follow up studies reported the use of a small molecule dorsomorphin (DM) instead of Noggin, that at least in part produced similar cells with differences in consistency of cultures (Kim, et al., Robust enhancement of neural differentiation from human ES and iPS cells regardless of their innate difference in differentiation propensity. *Stem Cell Rev* 6, 270-281, (2010); Zhou, et al., High-Efficiency Induction of Neural Conversion in hESCs and hiPSCs with a Single Chemical Inhibitor of TGF-beta Superfamily Receptors. *Stem Cells*, 504, (2010), herein incorporated by reference).

The inventors observed that cells generated using Noggin despite showing the same developmental stage as LDN treated cells, expression of the vast majority of the same markers, and capable of a similar developmental potential to make various neural lineages, also showed differences, such as being more anterior on an anterior-posterior axis (i.e. more forebrain, more cells express FOXG1, and the like) compared to neural cells induced using LDN. Thus although LDN was used in place of Noggin to inhibit BMP among other signaling pathways, Noggin and LDN may have other types of activities which are different, besides inhibiting BMP.

In part due to the high expense of using Noggin, the inventors contemplated that the use of a BMP inhibitor might be able to substitute for Noggin in producing cells of neural cell fate. Therefore, a small molecule BMP inhibitor, LDN-193189, (Yu, et al., *Nat Med* 14, 1363-1369, (2008), herein incorporated by reference) was used and found during the development of the present inventions to replace Noggin, in combination with SB431542, for generating primitive neuroectoderm from hPSCs, cells that have neural cell fate, i.e. CNS cells (FIG. 2A). This combination treatment was termed LSB for the combination of these two inhibitors LDN-193189 and SB431542.

Example III

Screening Small Molecules Using Neuronal Lineage Cells of the Present Inventions Resulted in Compounds that Produced PAX6 Low and TUJ1 High Neuronal Cells The following example describes using exemplary cells of a neural lineage from Example II for screening small molecule candidate compounds for use in directed differentiation.

Specifically, in the context of dual SMAD inhibition (LSB), i.e. human ES cells were first treated with LSB (LDN-193189 and SB431542) for screening candidate compounds (i.e. small molecules) under approximately 400 conditions in order to find combinations of small molecules that might accelerate the acquisition of postmitotic neuron markers starting from human ES cells. Candidate compounds were chosen from molecules that targeted (altered) cell signaling pathways known to be important and frequently used in developmental studies in order to determine cell fates (for example, signaling pathways such as FGF, Notch, WNT, SHH (Sonic Hedgehog), etc.) for determining cells capable of CNS development. As one example, 4 types of inhibitors (i.e. SU/DAPT/CHIR/Cyclopamine) were tested in different combinations (as fed to cells in cell medium) on different days of LSB treatment. Each treatment was then screened on Day 10 for TUJ1/PAX6 expression. As one example of a treatment condition: LSB was fed daily, CHIR and SU were added to the medium to feed cells daily on days 4-10.

In general, results of screening treatments resulted in large numbers of cultures containing dead cells. In other words, viable culture conditions during this screen were found much less frequently than unviable conditions (i.e. cell death), for example, when SU/DAPT was added to early cultures, i.e. prior to day 2. The inventors contemplated that CNS stem cells depend on FGF signaling and gamma-secretase activity/Notch signaling for survival, therefore when CHIR was absent when SU/DAPT induced cells to switch from CNS to neural crest, instead of switching, the cells died.

On day 10 after addition of LSB, cells that survived during the screen were monitored for the loss of the human neuroectoderm marker PAX6 (Zhang, et al., Cell Stem Cell 7, 90-100, (2010), herein incorporated by reference) and initiation of neuronal differentiation by TUJ1 expression (Lee, et al., Cell Motil Cytoskeleton 17, 118-132, (1990), herein incorporated by reference). The cells were stained for neurons (TUJ1+) and a loss of neuroectoderm (observation of fewer PAX6+ cells) using an antibody that binds the C-terminus of PX6), by immunofluorescence (immunoF). This screening was done on the numerous combinations of inhibitors (for example, SU, SU/DAPT, SU/DAPT/CHIR, DAPT/CHIR, SU/CHIR, SU/Cyclopamine, etc.) were added in variations of daily feedings on combinations of days, (for example, days 0-10, 1-10, 2-10, 3-10, etc.). In general, results were determined by observing comparative amounts of TUJ1+/PAX6− staining of cells generated by each treatment such that the conditions and compounds showing the highest amounts of TUJ1+/PAX6− staining were chosen as successful for providing cells for further analysis. One example of a small molecule that was considered a failure during the screening test for producing cells that were TUJ1+/PAX6− by immunostaining of cells was Cyclopamine. Cyclopamine appeared to have no effect on cells for producing TUJ1/PAX6 staining no matter when it was added. In other words, the cell morphology remained similar to those cells with LSB treatment alone (i.e. >90% PAX6+ and <10% TUJ1+) on day 10 by immunofluorescence.

However, during the screen the inventors discovered that a specific combination of three small molecules (SU5402, CHIR99021, and DAPT; termed 3i for three inhibitors), added on day 2 of LSB treatment (FIGS. 6A and B), abolished PAX6 expression and induced TUJ1 in hPSCs at day 10 of differentiation (FIGS. 2A and B). This was a surprising discovery because at day 2 of LSB treatment the treated cells were not yet known to have a neural cell fate or for having the capability to develop into a neural cell fate. Instead, 3i treatment directed cells away from a neural cell fate into neural crest cells which were further differentiated into the nociceptor cells of the present inventions.

The functions for each of these small molecules was then researched in order to discover which signaling pathways were contemplated to be involved in converting a PAX6+ TUJ1− human ES cell population into a PAX6-TUJ1+ population. First, SU5402 was reported as a potent inhibitor of VEGF, FGF, and PDGF tyrosine kinase signaling (Sun, et al., J Med Chem 42, 5120-5130, (1999), herein incorporated by reference). Thus in general it was contemplated that at least one of the small molecules was involved with inhibiting FGFR signally pathways. Secondly, CHIR99021 was reported as a WNT agonist by selectively inhibition of GSK-3β which stabilized β-catenin (Bennett, et al., J Biol Chem 277, 30998-31004, (2002), herein incorporated by reference). Thus in general it was contemplated that at least one of the small molecules was involved with activating at least one of the WNT signalling pathways through glycogen synthase kinase 3β (GSK3β) inhibition. And thirdly, DAPT was reported as a γ-secretase inhibitor capable of blocking Notch signaling (Dovey, et al., J Neurochem 76, 173-181 (2001), herein incorporated by reference). Thus in general it was contemplated that at least one of the small molecules was involved with inhibiting at least one Notch signaling pathway. Thus in one embodiment, one of the small molecules was contemplated as a nonselective or pan-Notch inhibitor. In another embodiment, one of the inhibitors is an inhibitor of γ-secretase molecules, capable of blocking at least one Notch signaling pathway. Therefore, in one exemplary embodiment, a combination of inhibitors would include at least one small molecule involved with inhibiting FGFR signalling pathways, at least one small molecule involved with inhibiting at least one Notch signaling pathway, and at least one small molecule involved with inhibiting GSK-3β while activating at least one of the WNT signalling pathways for producing PAX6-TUJ1+ human neuronal cells of the present inventions. In further embodiments one of the inhibitors was capable of blocking at least one γ-secretase molecule in the Notch signaling pathway.

Example IV

TUJ1+ Neuronal Cells Show a Loss of Expression of Cell Proliferation Markers

The following example describes an exemplary method for determining the maturational (cell cycle) stage of TUJ1+ neuronal cells.

Upon maturation, neurons produced in culture ceased to undergo mitosis while loosing Ki67 and phospho-histone H3 (PHH3), markers of cell proliferation (Gerdes, et al., Int J Cancer 31, 13-20 (1983), herein incorporated by reference) and G2/M-phases of mitosis (Hendzel, et al., Chromosoma 106, 348-360 (1997), herein incorporated by reference), respectively. Therefore, cells produced using LSB in combination with 3i (i.e. LSB3i) were passaged to a lower density, approximately 10-100,000 cells/cm$^2$ and tested for cell proliferation markers, Ki67 and phospho-histone H3 (PHH3), after fixation to better assess expression, in individual cells. In particular, expression of Ki67 was known to be a better predictor of proliferation. Thus, compared to cells cultured in LSB without 3i compounds, after 12 days fewer cells, 50% and 16%, cultured in the presence of 3i showed a loss of Ki67+ and pHH3+ cells, respectively (FIG. 2 C-F).

Intercellular FACS staining for Nestin, a marker of neural progenitors, and β3-tubulin (TUJ1) a marker of neuronal differentiation, was performed to quantify the efficiency (percentage) of neuronal differentiation using LSB3i compared to LSB alone as a control in addition to LSB/CHIR (CHIR99021; C), SU/DAPT (SU5402/DAPT), SU/CHIR (SU5402/CHIR99021), DAPT, SU (SU5402), CHIR (FIG. 2G). In the presence of LSB, SU/DAPT, DAPT, SU and CHIR, the majority of cells expressed Nestin. In particular, >95% of the LSB cell population were Nestin+. Numerous cells showed Nestin staining after dual SMAD inhibition but were not quantitated while longer term cultured cells, i.e. 19 days, showed TUJI+ neurons where the majority of these cells co-expressed tyrosine hydroxylase (TH) identifying potential dopaminergic neurons (Chambers, et al., Nat Biotechnol 27, (2009), herein incorporated by reference). Conversely, when LSB contacted cells were contacted 2 days later with the 3i compounds, after 10 days approximately 25% of cells expressed Nestin while approximately 75% of cells expressed TUJ1, demonstrating efficient conversion to a neuronal cell fate after short-term cell culture, i.e. less than 19 days.

Surprisingly, LSB treatment followed 2 days later by contacting cells with CHIR99021 and either one of DAPT or SU resulted in 50% of the cell population differentiating into TUJ1+ cells. When each of the three inhibitors was used alone after LSB treatment, 20% or fewer cells were TUJ1+. Therefore CHIR99021 was discovered as the key contributor to directed differentiation of this cell population into TUJ1+ neuronal cells. The inventors contemplated directed differentiation of nestin+ TUJ1− cells into nestin−TUJ1+ neuronal cells was dependent on inibition of GSK-3β while activating at least one of the WNT signalling pathways in addition to inhibiting either FGF receptor pathways or a gamma secrease within a Notch signalling pathway. Further, the addition of the 3i compounds resulted in a conversion of an additional 25% nestin−TUJ1+ neuronal cells, see, FIG. 2G.

In summary, the neuronal population derived from a preferred embodiment of 3i treatment 2 days after LSB treatment was further examined. This population showed high expression of the neuronal marker TUJ1 compared to cells treated with LSB alone (FIG. 2A,B) as well as loss of Ki67 (FIG. 2C,D). Loss of Ki67 indicates reduction in cell cycle which is characteristic of post-mitotic differentiated neurons. Additionally, FACS analysis revealed that over 75% of the cell population treated with a preferred composition consisting of LSB and 3i expressed TUJ1 compared to 99% of the population treated with LSB alone which expressed Nestin, a progenitor marker (FIG. 2G).

Example V

TUJ1+ Neurons were Surprisingly Peripheral Nervous System (PNS) Cells Instead of Expected Central Nervous System (CNS) Cells The following example describes an exemplary method for identifying the type of TUJ1 positive neuron produced during the development of the present inventions.

To further characterize the subtype of neurons obtained from a preferred embodiment of 3i treatment 2 days after LSB treatment, the TUJ1 positive population was stained for markers of various neuronal subtypes. Specifically, the dual-SMAD-inhibition protocol was known to generate PAX6+ neuroepithelial cells biased towards anterior forebrain identity expressing FOXG1 (Forkhead box protein G1) (Chambers, et al., Nat Biotechnol 27, (2009), herein incorporated by reference). Therefore, in order to determine the neuronal subtype identity following LSB3i treatment, cells were passaged to a lower density, approximately 10-100,000 cells/cm$^2$ at day 10 and assessed for a range of marker expression at day 12

Since the expected neuronal type was a CNS fate, the majority of initial markers tested were for identification of CNS type cells. In fact, a CNS forebrain neuron was expected since LSB cells default to this subtype (PAX6, FOXG1 positive). Surprisingly, at least 12 negative results (an exemplary 10 are shown below) for CNS markers were obtained before staining for ISL1, a marker for PNS cells, was discovered. ISL1 is expressed by motoneurons and peripheral sensory neurons. BRN3A expression was tested and found to be expressed by LSB/3i cells. Therefore, the inventors discovered BRN3A+/ISL1+ neurons which indicated development of peripheral sensory neurons, see Table A, below.

TABLE A

The following list of genes/proteins that represent numerous CNS fate molecules that were expected to be positive (expressed) on cells using the LDN/3i induced differentiation as described herein. However, these results showed an exemplary lack of CNS markers, results which were supported by the subsequent finding of potential markers for PNS lineage, i.e. ISL1 and BRN3A.

| Gene/Protein | Marks (neuron type) | Result (IF or FACS) |
|---|---|---|
| FOXG1 | Forebrain | Negative |
| FOXA2 | Midbrain | Negative |
| TBR1 | Cortical | Negative |
| PAX6 | Forebrain | Negative |
| AADC | Dopamine | Negative |
| TH | Dopamine | Negative |
| DCX | Pan-neuronal | >75%, costained with TUJ1 |
| Nestin | Progenitors | <25%, counterstained with TUJ1 |
| ChAT | Cholinergic | Negative |
| GAD65 | GABA | Negative |
| Reelin | Cortical and juvenile neurons | Positive |
| GABA | GABA | Negative |
| MASH1 | Autonomic | Negative |
| BRN3A | Peripheral sensory | Positive |
| ISL1 | Motoneurons, Peripheral sensory | Positive |

Surprisingly, homogenous expression of ISL1 and BRN3A (red/darker areas within cells) (FIGS. 3A and B) were observed on TUJ1+ cells (green/lighter cell bodies compared to red staining) of the present inventions. ISL1 and BRN3A are key markers for sensory neurons (ISL1: Sun, et al., Nat Neurosci 11, 1283-1293, (2008); BRN3A: Gerrero, et al., Proc Natl Acad Sci USA 90, 10841-10845 (1993), all of which are herein incorporated by reference). This discovery indicated that the neurons that resulted from LSB3i treatment were PNS rather than CNS cells. These results were in contrast to LSB cells that default to a CNS forebrain neuron subtype (PAX6+, FOXG1 positive). This is quite a unexpected finding as the high confluency of the stem cells upon initiation of the treatment, as represented by plating density, according to the teachings of the prior art, should have resulted in CNS derived neuronal populations.

However, nociceptors are derived from neural crest cell populations which, according to the teachings of the prior art, are derived from low confluency of the stem cells upon initiation of the treatment, as represented by plating density. In other words, the expectation was that a high initial plating density>20,000 cells/cm² of pluripotent stem cells at the time of initiation of LSB treatment would result in a committed CNS neuronal population. In contrast, a low initial plating density approximately 10,000 cells/cm² was known to be necessary to result in neural crest cells (Chambers et al, Nature Biotech, 2009 (See lower half of FIG. 4), herein incorporated by reference in its entirety).

Example VI

Peripheral Nervous System (PNS) Neurons were Discovered to be Early Stage Nociceptor Cells The following example describes using exemplary methods for determining which type(s) of peripheral nervous system (PNS) neurons were produced using methods described herein.

It was not known what type(s) of PNS neurons were produced by the methods described herein as there were several types of candidate neurons, such as sensory neurons and motor neurons, and further there were at least three major subsets of known sensory neurons in the PNS including proprioceptor cells, mechanoceptor cells, and nociceptor cells.

During development, early stage nociceptors were both peptidergic and nonpeptidergic and uniquely expressed NTRK1, RUNX1, followed by RET expression (for an example of information on RET, see, Woolf, et al., *Neuron* 55, 353-364, (2007), herein incorporated by reference). Duplicate early stage LSB3i-cultures with TUJ1+ neurons were tested for RET expression (FIG. 3C), and discovered to be positive for this marker (red/darker areas within cells in the larger box compared to TUJ1+ staining (green/lighter cell bodies compared to RET staining) and lighter stained areas within inserted RET box). (FIG. 3D), and greater than 60% of all cells in culture expressed NTRK1 when measured by FACS at day 10 (FIG. 3E).

In summary, this population was positive for expression of ISL1, BRN3A, RET, and RUNX1 (FIG. 3A-D) indicating the production of early stage nociceptors (both peptidergic and nonpeptidergic). FACS analysis revealed that greater than 60% of these neurons were positive for NTRK1 (FIG. 3E). These markers collectively indicate that the neuronal population are peripheral sensory neurons, in particular nociceptors.

Therefore a preferred embodiment of the combination of LSB with 3i treatment on day 2 results in unexpected formation of neural crest derived populations, namely nociceptors.

Further, the inventors combined information from several tests, including initial immunofluorescence results, i.e., BRN3A+, ISL1+, array data, i.e. TAC1 (Substance P) expression, then choosing a NTRK1 marker and finding NTRK1+ cells, in addition to observations described herein where cells obtained by LSB/3i treatment transitioned through neural crest and transiently expressing Neurogenin1 (NEUROG1) instead of differentiating into a CNS fate. Thus the inventors contemplated that the resulting PNS cell was most likely a peptidergic nociceptor.

Example VII

LSB3i Treatment is Reproducible

The following example describes using exemplary methods of the present inventions for determining reproducibility.

To establish the generality of the present invention, the inventors repeated a preferred embodiment of the present invention combining 3i treatment 2 days after LSB treatment using hiPSC as the source of stem cells. Reproducibility of LSB3i treatment was accessed across additional hPSC lines including induced pluripotent stem cell (hiPSC) lines. The current art describes any number of methods to produce hiPSC and will be known to those skilled in the art. In particular, two hiPSC lines (C14 and C72) were used that were generated by inserting genes such as Oct4 (octamer-binding transcription factor 4), Sox2 (SRY (sex determining region Y)-box 2), Klf4 (Kruppel-like factor 4), and c-Myc (Transcription factor p64) and shown to efficiently neuralize (see, (Papapetrou, et al., *Proc Natl Acad Sci.*, USA 106, (2009), herein incorporated by reference)).

PAX6 expression was then examined by ImmunoF. LSB and LSB3i treatment of C14 and C72 cell lines showed similar neuronal staining results when compared to human cell lines shown in FIG. 3A-D. Exemplary C14 staining results are shown in FIG. 4A-D while exemplary C72 staining results are shown in FIG. 8A-D for ISL1, BRN3A, RET, RUNX1 and TUJ1, as described above.

LSB treatment of C14 and C72 cell lines homogeneously gave rise to Nestin positive cells (>95% of the treated cell population) and were capable of forming TUJ+ cells when treated with combination of LSB3i as measured by FACS (40% for C14 and 33% for C72; FIG. 4E). These results were compared to H9 cell line (i.e. a hESC line) treated with LSB and LSB3i shown for LSB and LSB3i results in (FIG. 4E). Even higher neuron yields, from 40% and 33% measured by FACS, became >90% of nuclei staining are neurons when sorted on NTRK1 were obtained in those two hiPSC lines upon passaging of bulk cultures into culture vessels coated with Matrigel™ containing N2 media after sorting on NTRK1 (Neurotrophic tyrosine kinase receptor type 1) marker expression. Cells were disaggregated with accutase, re-suspended in N2, and incubated on ice with APC-conjugated NTRK1 antibody (R&D) for 15 minutes, washed, and re-suspended in N2 for FACS. After sorting the cells were cultured for 24 hours in N2 media, and fixed in place. Cells were collected and stained for BRN3A, ISL1, TUJ1 and DAPI. In particular, numerous Nestin+ cells (red/dark staining) are shown for both C14 and C72 NTRK1− cells from LSB3i treated cells compared to few Nestin+ cells in the representative NTRK1+ LSB3i treated cell population (FIG. 9). Further, while few C14 NTRK1− cells expressed TUJ1 cell line C27 showed a higher number of NTRK1− TUJ1+ (green; bright staining). Both cell lines showed high numbers of Nestin−TUJ1+ cells as observed compared to cell bodies identified by DAPI (blue; light nuclear) staining.

In summary, hiPSC cells plated at a high confluency treated with LSB followed by 3i on day 2 resulted in the formation of neuronal cells positive for the nociceptor markers ISL1, BRN3A, RET, and RUNX1 (FIG. 4A-D, FIG. 8A-D and FIG. 9.

Example VIII

CHIR99021 (C) is the Key Factor for Inducing Neuronal Differentiation from LSB Cultured Cells (i.e. LSB-C)

The following example describes using exemplary methods for testing the efficacy of each compound for inducing directed neuronal differentiation.

In order to gain mechanistic insights into the sufficiency of each compound found to associated with the induction of TUJ1+ cells of Example III, specific combinations of 3i compounds were tested for inducing cellular expression of Nestin and TUJ1 as measured using intercellular FACS (shown in FIG. 1G). Nestin was used as a marker of the LSB neural lineage cells while TUJ1 was used to identify a downstream (i.e. more differentiated) neuronal cell.

Although none of the individual factors yielded high numbers (greater than 60%) of TUJ1+ neurons, CHIR99021 in combination with either one of the other two signal inhibition factors was capable of generating moderate numbers of TUJ1+ neurons (53% for DAPT and 58% for SU5402). These data indicate that under the test conditions used herein, CHIR99021 was the key factor for accelerating neuronal differentiation while SU5402 and DAPT provided important, yet additive stimuli.

Additionally, all 3 components of the 3i composition are required for the maximum yield of differentiated neurons (FIG. 2G).

Example IX

Artificial SOX10+ Cells are Capable of Producing Nociceptor Cells

The following example describes using exemplary methods of the present inventions for directed differentiation of engineered SOX10+ GFP expressing human cells.

Nociceptor cells are contemplated to arise from two types of cell intermediates during human development: specifically SOX10+ chick embryo neural crest cells were found to be capable of generating trunk nociceptor cells flanking the spinal cord (George, et al., Nat Neurosci 10:1287-1293, (2007), herein incorporated by reference). Additionally, Xenopus laevis head placode tissue contributed to the trigeminal nociceptor cell population in facial tissue (Schlosser, et al., J Comp Neurol 418:121-146, (2000); Schlosser, et al., Dev Biol 294:303-351, (2006), herein incorporated by reference).

Thus, in order to determine if a neural crest intermediate cell fate marked by SOX10 (Aoki, et al., Dev Biol 259, 19-33, (2003); Lee, et al., Nat Biotechnol 25, 1468-1475, (2007), herein incorporated by reference) in human cells would be observed during differentiation using a transgenic SOX10::GFP bacterial artificial chromosome (BAC) hPSC line. This SOX10:: GFP (BAC) cell line was generated with enriched neural crest gene markers that co-expressed with a GFP gene using methods previously reported (Placantonakis, et al., Stem Cells 27:521-532, (2009), herein incorporated by reference). The SOX10:GFP cell line was a subclone of the H9 hESC line. Cells were dissociated and gene delivery was performed using reagents (solution V), protocol (B-16), and equipment from Amaxa. The DNA nucleofected (transfected into the nucleus) was a bacterial artificial chromosome (BAC) containing the SOX10 gene with an inserted GFP, obtained from Gene Expression Nervous System Atlas [GENSAT] (accession number: GENSAT1-BX1086). The BAC was then modified to include a neomycin resistance gene for selection (see Tomishima, et al. Stem cells 25(1):39-45. Epub 2006 Sep. 21 (2007, herein incorporated by reference) using cre/LoxP recombination from a selection cassette excised from the pL452 plasmid into the GENSAT BAC. After gene delivery hESCs were seeded as single cells in the presence of G418 for neomycin resistance selection and clones were manually picked and screened for the presence of GFP upon differentiation. GFP cells were sorted to confirm the expression of SOX10 and other neural crest markers by qRT-PCR.

GFP expression was measured by FACS identification and sorting of SOX10::GFP+ cells at 4, 8, 12, and 16 days after initiating differentiation with LSB when two additional duplicate samples were contacted each with one of LSB then CHIR99021 (LSB/C) or LSB with 3i.

When CHIR99021 was present greater than 70% of these treated cells in culture became SOX10::GFP+ by day 12 of differentiation for the culture conditions (70% for LSB/C and 80% for LSB3i; FIGS. 5D and E). This result indicated that the majority of cells develop a neural crest identity, supporting the inventors' observation that CHIR99021 was required for the generation of LSB3i nociceptor cells. Thus combined inhibition by these small molecules which inhibited tyrosine receptor kinase receptors and Notch signaling, in addition to contacting SU5402 and DAPT, respectively, accelerated neural crest cell fate, since LSB3i treated cells acquired a neural crest fate more rapidly in comparison to LSB/C treated hPSCs (FIGS. 5D and E). The inventors contemplated that CHIR induced neural crest and sensory neurons while SU accelerated neural crest marker expression and neuronal differentiation. Finally, the inventors contemplated that DAPT in combination with CHIR and SU accelerated neuronal differentiation. Further, the use of CHIR99021 in combination with LSB, i.e. LSB/C resulted in a slower conversion rate of over 60% of Nestin–TUJ1+ neuronal cells compared to LSB3i between days 12 and 16 when using the engineered SOX::GFP cells as a read-out.

Example X

NTRK1+ Human Nociceptor Cells Produced by Methods Described Herein Showed Gene Expression Consistent with Peptidergic Cells and Electrophysiology Responses Similar to Rat Nociceptor Cells In Situ The following example describes using exemplary methods of the present inventions for determining the functional capability of nociceptor cells produced by methods described herein.

LSB3i treated cells were examined for function, maturation stages, and behaviors in order to confirm that LSB3i derived neurons were bona fide nociceptor neuronal cells. After LSB3i treatment of pluripotent stem cells resulted in nociceptor cells were obtained long term cultures were established from a plating density of 10-100,000 cells/cm$^2$ and passaged Day 10, 30 days in culture in N2 medium supplemented with human-beta NGF, BDNF, and GDNF (see, Example I for additional details). Survival rate of these cells under longer-term culture conditions was found to be NGF dependent compatible with NTRK1+ nociceptor status. LSB3i nociceptors expressed high levels of TUJ1, ISL1, BRN3A (FIG. 7A-C) as shown previously, in addition to glutamate (FIG. 7C). Glutamate production was consistent with an excitatory glutamatergic neuron, i.e. a nociceptive afferent fiber that releases glutamate, and the capsaicin receptor TRPV1 (FIG. 7D), an important ion channel for noxious stimulus. On day 15 in culture two distinct growth processes could be identified for each neuron (FIG. 7E, FIG. 12).

The dendrite marker MAP2 was expressed primarily in one of the two processes in a polarized fashion (FIG. 7F). The bipolar nature of the neurons was in agreement with the role of sensory neuron in the peripheral ganglia with the cell body is located in the dorsal root ganglion projecting processes both towards the spinal cord and towards the periphery (Woolf, et al., Neuron 55, 353-364, (2007); George, et al., Nat Neurosci 10, 1287-1293, (2007), herein incorporated by reference).

In the presence of nerve growth factor (NGF), neurons were cultured long-term (for example, cells passaged day 10 and cultured up to day 30). LSB was withdrawn on day 5, 3i withdrawn from cells on day 10 when NGF/GDNF/BDNF were added into medium. The neurons were fed NGF/GDNF/BDNF from day 10 up to day 30. On Day 30, the number of days from initial LSB treatment, the neurons was observed to have started to self-organize into ganglia-like structures. This type of morphology is common to peripheral sensory neurons (Marmigere, et al., Nat Rev Neurosci 8, 114-127, (2007), herein incorporated by reference) (FIGS. 7G, H, and I).

Mature nociceptors are typically either peptidergic or non-peptidergic depending on expression of neuropeptides, such as calcitonin gene related peptide (CGRP) and Substance P (a neuropeptide) expressed by peptidergic sensory neurons, (Woolf, et al., Neuron 55, 353-364, (2007), herein incorporated by reference). In contrast, non-peptidergic neurons do not express CGRP nor Substance P and have other markers such as binding to the lectin IB$_4$.

Therefore, LSB3i induced neurons were sorted for NTRK1 expression (see methods described above), using FACs, into NTRK1+ and NTRK1- populations (for example of a sorted cell, see, FIG. 7G. NTRK1+ cells were positive for both Substance P and CGRP indicating primarily a peptidergic nocicieptors phenotype (FIGS. 7H and I; day 30 of differentiation).

A primary functional hallmark of sensory neuron identity (i.e. function) is their electrophysiological signature (Fang, et al., J Physiol 565, 927-943, (2005), herein incorporated by reference). NTRK1+ sorted neurons were also tested by standard electrophysiology techniques for cultured neurons (Placantonakis, et al. Stem Cells. 2009, FIG. 5 has an example, herein incorporated in its entirety)

NTRK1+ cells exhibited a characteristic single action potential (AP), electrophysiological signature, firing pattern with an average membrane resting potential of 67±4 mV by day 21 after initial LSB3i treatment. The resulting AP timing and shape of action curve in LSB3i human neurons are shown in FIG. 7J, see thick red line) and Table 1 below. These results were similar to those described previously in electrophysiological reports of primary anaesthetized adult rat nociceptors (Fang, et al., J Physiol 565, 927-943, (2005), herein incorporated by reference).

TABLE 1

Electrophysiology of human LSB3i Cultured Cells compared to rat nociceptive and non-nociceptive dorsal root ganglion neurones in vivo.

| Action Potential | LSB3i Cells | Nociceptor Cells* | Mechanoreceptor Cells* |
|---|---|---|---|
| Duration at base (milli-second; ms) | 9.5 | 6 | 2 |

TABLE 1-continued

Electrophysiology of human LSB3i Cultured Cells compared to rat nociceptive and non-nociceptive dorsal root ganglion neurones in vivo.

| Action Potential | LSB3i Cells | Nociceptor Cells* | Mechanoreceptor Cells* |
|---|---|---|---|
| Rise time (milli-second; ms) | 3.8 | 2 | 0.8 |
| Fall Time, Tussman and Misc. (milli-second; ms) | 5.8 | 3.5 | 1 |
| Overshoot (milli-volt; mV) | 29 | 22.5 | 5 |
| 80% Recovery (milli-second; ms) | 15.1 | 21 | 5 |

*Fang, et al., J Physiol 565.3: 927-943 (2005)

Example XI

Gene Expression of Cells Produced by Compositions and Methods Described Herein

The following example describes using exemplary methods for determining global gene expression of nociceptor cells and other cells types produced by methods described herein.

Global gene expression analysis was performed at fine temporal resolution (days 2, 3, 5, 7, 9, and 15, NCBI Gene Expression Omnibus (GEO) accession number GSE26867; for both LSB and LSB3i treated hPSCs to further characterize the timing of events (i.e. marker expression) during the induced differentiation process. When select markers for neuroectoderm, neural crest, neurons, and nociceptors were analyzed (see Table 2 below), distinct phases of differentiation for each could be observed (FIG. 10).

TABLE 2

Gene expression assigned to specific phases of differentiation during directed differentiation after contact with LSB-3i. See also, FIG. 10A.

| Phases of Differentiation | Genes Expressed |
|---|---|
| Neurectoderm | PAX6, OTX2, DLK1, DKK1, CUZD1 |
| Neural Crest | SOX10, MSX1, ID2, AP2B, ETS1, FOXD3 |
| Neuron | NGN1, DCX, TUBB3, SYT4, STMN2, INA, GAP43, ISL1, POU4F1 |
| Nociceptor | TAC1, VGLUT2, SLC15A3 |

This gene expression analysis (FIG. 10B,C and Table 2 above) was consistent with the majority of immunofluorescence results. For example, gene analysis showed that in maturing neurons, ISL1, POU4F1 (BRN3A), SOX10, TAC1 (pro-peptide to Substance P), NTRK1, and the glutamate vesicular transporter VGLUT2 genes were all upregulated (i.e. the number of cells in culture increased the expression of these markers over time). Concurrently while these markers were observed to be increased on induced cells, markers for hESC-derived primitive neuroectoderm were observed to be downregulated (i.e. expressed on fewer cells in culture), in particular DLK1, LHX2, OTX2, LEFTY2, PAX6, and HES5.

However, expression of somatostatin (SST) and SOX10 was found at day 15 in LSB3i treated cell cultures, which is expected to be expressed in mature nociceptors. However, SST was also shown expressed in developing sensory neurons. Therefore, the inventors contemplated that this marker was indicating the presence of immature cells at day 15. Though somewhat down-regulated, SOX10 expression was also observed at a time when most cells appeared to be neurons. This finding was unexpected since SOX10 was expected to be downregulated as the cells differentiate into neurons. This unexpected discovery of SST and SOX10 expression in cells of day 15 cultures was contemplated as not all of the become nociceptors cells, approximately 20-30%. This indicated that other mature cell types (such as Schwann cells) continue to express SOX10.

hESC-derived primitive neuroectoderm cell cultures produced by dual SMAD inhibition in Chambers, et al., Nat Biotechnol 27, (2009); Fasano, et al., Cell Stem Cell 6, 336-347, (2010), each of which are herein incorporated by reference), demonstrated high expression of DLK1, LHX2, OTX2, LEFTY2, PAX6, and HES5 genes. Likewise, similar high expression for these genes was observed when hESC-derived primitive neuroectoderm cell cultures were produced by dual SMAD inhibition using LSB (see FIG. 10B,C and Table 3 below). These genes were reduced during LSB3i treatment while producing nociceptors during the development of the present inventions.

TABLE 3

Timing of gene expression during directed differentiation with LSB-3i compared to LSB.

| LSB-3i Differentiation compared to LSB control | Genes upregulated | Genes downregulated |
| --- | --- | --- |
| Day 7 | ISL1, POU4F1 (BRN3A), SOX10, NTRK1, and the glutamate vesicular transporter VGLUT2 | DLK1 |
| Day 9 | ISL1, POU4F1 (BRN3A), SOX10, NTRK1, and the glutamate vesicular transporter VGLUT2 | DLK1 and PAX6 |
| Day 15 | ISL1, POU4F1 (BRN3A), SOX10, TAC1 (pro-peptide to Substance P), and the glutamate vesicular transporter VGLUT2 | DLK1, LHX2, OTX2, LEFTY2, PAX6, and HESS |

In addition, the temporal transcriptome analysis provided further evidence for nociceptor intermediate cell fates, distinct from mechanoceptor cells and proprioceptor cells. The neurogenin basic helix-loop-helix proteins mediate two sequential waves of neurogenesis in the dorsal root ganglia during mouse development (Marmigere, et al., Nat Rev Neurosci 8, 114-127, (2007); Ma, et al., Genes Dev 13, 1717-1728 (1999), herein incorporated by reference). The first wave, marked by NEUROG2 (Neurogenin-2) gives rise to mechanoceptor cells and proprioceptor cells, and the second marked by NEUROG1 (Neurogenin-1) gives rise to nociceptor cells. When hPSCs are treated with LSB, NEUROG2 expression is strongly induced by day 7 (FIG. 10C and Table 4 below). In contrast, hPSCs treated with LSB3i show a less pronounced induction of NEUROG2 by day 7 but selective induction of NEUROG1 by day 9 (FIG. 10C).

TABLE 4

Timing of gene expression during directed differentiation with LSB-3i compared to LSB.

| neurogenin basic helix-loop-helix genes expressed in treated hPSCs | Day 7 | Day 9 |
| --- | --- | --- |
| LSB-3i | No difference in NEUROG1 compared to LSB control cells No change in % of cells expressing NEUROG2 | NEUROG1 induction No change in % of cells expressing NEUROG2 |
| LSB control | No difference in NEUROG1 NEUROG2 induction | No difference in NEUROG1 Downregulation of NEUROG2 |

Example XII

Contemplated Large Scale Culture Using Compositions and Methods of the Present Inventions for Providing Exemplary Nociceptor Cells The following contemplated description shows exemplary methods and uses for large-scale production of nociceptor cells produced by methods described herein.

The scalable generation (i.e. methods contemplated to be successful for generating nociceptor cells from both cultures containing a relatively small number of cells, for example, $1.5 \times 10^4$ cells/well of 48 well plates such as described in Examples, supra), and contemplated $5 \times 10^3$ cells/well in 96 well plate, up to large batch cultures of hPSC derived nociceptors, (for example, $1 \times 10^7$-$1 \times 10^8$ cells in batches of 18 15 cm dishes (approximately $5.5 \times 10^7$ cells), using LSB3i. These methods are contemplated to provide hPSC derived nociceptor cells for use in testing compounds for use in basic biology studies and for drug discovery applicable to medical applications in humans and animals. In particular, the inventors' contemplate the use of compositions and methods of the present inventions for treatments to reduce acute and chronic pain in humans and animals.

In particular, large batch cultures are contemplated wherein exemplary $1 \times 10^8$-$1 \times 10^9$ hPSC cells are grown in batch embryoid body cultures using culture medium and exemplary compounds as described herein for providing exemplary nociceptor cells, for example, peptidergic nociceptor cells, in exemplary nonlimiting ranges of $7 \times 10^7$-$7 \times 10^8$ (wherein a 70% efficiency of nociceptor cell harvest is contemplated). Exemplary nociceptor cells are contemplated to express genes (i.e. mRNA and protein) identifying nociceptor cells, such as TAC1, VGLUT2, and SLC15A3. Exemplary nociceptor cells are contemplated to express identification markers, such as ISL1, BRN3A, RET, RUNX1, Substance P, CGRP, etc.

In summary, the inventors' contemplate using compositions and methods of the present inventions to provide novel platforms in basic biology and drug discovery for the study and treatment of conditions associated with nociceptor cells, in particular pain, in humans and animals.

TABLE 5

Primer pairs used for amplification and identification of gene expression by PCR.

| SEQ NO. | | | Tm (° C.) | Product (bp) | | Reference |
|---|---|---|---|---|---|---|
| | NANOG | | | | | |
| 03 | Forward | CAGCTGTGTGTACTCAATGATAGATTTC | 58 | 461 | mRNA | This study |
| 04 | Reverse | GGAGAATTTGGCTGGAACTGCATG | 60 | 1840 | genomic | |
| | POU5F1 (OCT3/4) | | | | | |
| 05 | Forward | CCTGAAGCAGAAGAGGATCACC | 58 | 422 | mRNA | This study |
| 06 | Reverse | CATAGTCGCTGCTTGATCGC | 57 | 1191 | genomic | |
| | POU5F1 (OCT3/4) (qPCR) | | | | | |
| 07 | Forward | GAACCGAGTGAGAGGCAACCT | 60 | 80 | in exon | This study |
| 08 | Reverse | GGGCGATGTGGCTGATCT | 58 | | | |
| | SOX2 | | | | | |
| 09 | Forward | CAACATGATGGAGACGGAGC | 57 | 377 | in exon | This study |
| 10 | Reverse | GCAGCGTGTACTTATCCTTCTTC | 57 | | | |
| | GAPDH | | | | | |
| 11 | Forward | AGCCACATCGCTCAGACACC | 61 | 305 | mRNA | Joannides et al. |
| 12 | Reverse | GTACTCAGCGCCAGCATCG | 59 | 2153 | genomic | (2006) Stem Cells |
| | GAPDH (qPCR) | | | | | |
| 13 | Forward | GCACCGTCAAGGCTGAGAAC | 59 | 93 | mRNA | This study |
| 14 | Reverse | CGCCCCACTTGATTTTGG | 55 | 222 | genomic | |
| | BMP4 | | | | | |
| 15 | Forward | CCAACACCGTGAGGAGCTTC | 59 | 397 | mRNA | This study |
| 16 | Reverse | GTCCGAGTCTGATGGAGGTG | 58 | 1360 | genomic | |
| | AFP | | | | | |
| 17 | Forward | GTGCTTCCACCACTGCCAATAAC | 60 | 283 | mRNA | This study |
| 18 | Reverse | GTTCATCTCCAGTGGGTTTCTCAA | 59 | 2057 | genomic | |
| | BRACHYURY | | | | | |
| 19 | Forward | GATCACCAGCCACTGCTTCC | 59 | 161 | mRNA | This study |
| 20 | Reverse | CTCCGGGTTCCTCCATCATCT | 59 | 1138 | genomic | |
| | PAX6 | | | | | |
| 21 | Forward | GGAGTGAATCAGCTCGGTGG | 59 | 441 | mRNA | This study |
| 22 | Reverse | GGTCTGCCCGTTCAACATCC | 59 | 2072 | genomic | |
| | NCAM1 | | | | | |
| 23 | Forward | GGGCACTTATCGCTGTGAGG | 59 | 334 | mRNA | This study |
| 24 | Reverse | CTCGCCAGCCTTGTTCTCAG | 59 | 1868 | genomic | |
| | SOX1 | | | | | |
| 25 | Forward | GCAAGATGGCCCAGGAGAAC | 59 | 203 | in exon | This study |
| 26 | Reverse | CTTGTCCTTCTTGAGCAGCGT | 59 | | | |
| | SOX1 (qPCR) | | | | | |
| 27 | Forward | GAGAACCCCAAGATGCACAA | 56 | 70 | in exon | This study |
| 28 | Reverse | CCTCGGACATGACCTTCCA | 57 | | | |
| | BF1 | | | | | |
| 29 | Forward | ACTCAGAACTCGCTGGGCAAC | 60 | 226 | in exon | Yan et al. |
| 30 | Reverse | CGTGGGGGAAAAAGTAACTGG | 57 | | | (2005) Stem Cells |
| | HASH1 | | | | | |
| 31 | Forward | CAAGTCAGCGCCCAAGCAAGTCAAG | 64 | 384 | in exon | Kodama et al. (2006) |
| 32 | Reverse | GAGCCGGCCATGGAGTTCAAGTCGT | 67 | | | Immunol. Cell Biol. |

TABLE 5-continued

Primer pairs used for amplification and identification of gene expression by PCR.

| SEQ NO. | | | Tm (° C.) | Product (bp) | | Reference |
|---|---|---|---|---|---|---|
| | SIX3 | | | | | |
| 33 | Forward | CACTCCCACACAAGTAGGCAAC | 59 | 264 | mRNA | This study |
| 34 | Reverse | CATACATCACATTCCGAGTCGCTG | 59 | 1921 | genomic | |
| | DACH1 | | | | | |
| 35 | Forward | GGGCCAAAGTGGCTTCCTTC | 60 | 363 | mRNA | This study |
| 36 | Reverse | CAGGAGACATGAGACCAGGGAC | 60 | 184374 | genomic | |
| | EMX2 | | | | | |
| 37 | Forward | CGATATCTGGGTCATCGCTTCC | 58 | 368 | mRNA | This study |
| 38 | Reverse | GAGGTCACGTCTATTTCCTCCG | 58 | 4574 | genomic | |
| | GLI3 | | | | | |
| 39 | Forward | CAGCTCCACGACCACTGAA | 58 | 318 | mRNA | Zhu et al. (2004) |
| 40 | Reverse | TCCATGGCAAACACCGTCC | 59 | 74979 | genomic | Cancer Letters |
| | SHH | | | | | |
| 41 | Forward | CCAATTACAACCCCGACATC | 54 | 339 | mRNA | Li et al. (2005) |
| 42 | Reverse | CCGAGTTCTCTGCTTTCACC | 56 | 8173 | genomic | Nature Biotech. |
| | NKX2.1 | | | | | |
| 43 | Forward | TACTGCAACGGCAACCTG | 56 | 205 | mRNA | Zietlow et al. |
| 44 | Reverse | GCCATGTTCTTGCTCACGTC | 58 | 1170 | genomic | (2005) J. Anatomy |
| | HOXA4 | | | | | |
| 45 | Forward | CGCTCTCGAACCGCCTACAC | 61 | 181 | in exon | This study |
| 46 | Reverse | GCAGTTTGTGGTCTTTCTTCCACT | 59 | | | |
| | HOXB4 | | | | | |
| 47 | Forward | CCCTGGATGCGCAAAGTTCAC | 60 | 252 | mRNA | This study |
| 48 | Reverse | GGTGGTTGGGCAACTTGTGGT | 60 | 1094 | genomic | |
| | MAP2 | | | | | |
| 49 | Forward | GGCCCAAGCTAAAGTTGGTTCTC | 60 | 255 | mRNA | This study |
| 50 | Reverse | GCAGTGACATCCTCAGCCAAAG | 60 | 474 | genomic | |
| | SYT1 | | | | | |
| 51 | Forward | TCATCTGATGCAGAATGGTAAGAGG | 58 | 199 | mRNA | This study |
| 52 | Reverse | GTAGCCCACAAAGACTTTGCC | 58 | 4910 | genomic | |
| | PSD95 | | | | | |
| 53 | Forward | GGGAGAAGCAGCTCAACTCCAATCC | 59 | 180 | mRNA | This study |
| 54 | Reverse | CCAGCAAGGCCTGGAAGAG | 59 | 371 | genomic | |
| | GFAP | | | | | |
| 55 | Forward | CCGCCACTTGCAGGAGTACCAG | 63 | 324 | mRNA | This study |
| 56 | Reverse | TTCTGCTCGGGCCCCTCATGAG | 65 | 4041 | genomic | |

The following references are herein incorporated in their entirety:

Joannides A, et al. (2006) Automated mechanical passaging: A novel and efficient method for human embryonic stem cell expansion. *Stem Cells* 24:230-235

Kodama H, et al. (2006) Neurogenic potential of progenitors derived from human circulating CD14+ monocytes. *Immunol Cell Biol* 84:209-217.

Li X J, et al. (2005) Specification of motoneurons from human embryonic stem cells. *Nat Biotechnol* 23:215-221.

Yan Y, et al. (2005) Directed differentiation of dopaminergic neuronal subtypes from human embryonic stem cells. *Stem Cells* 23:781-790.

Zhu Y, et al. (2004) Functional Smoothened is required for expression of GLI3 in colorectal carcinoma cells. *Cancer Lett* 207:205-214.

Zietlow R, et al. (2005) The survival of neural precursor cell grafts is influenced by in vitro expansion. *J Anat* 207: 227-240.

Example XIII

Melanocytes are Derived from Human Pluripotent Stem Cells: LSB-Melanocytes (LSB-Mel)

The following describes exemplary compositions and methods for providing melanocytes for use in related disease modeling.

A Sox10:: GFP Bacterial Artificial Chromosome (BAC) human embryonic stem cell (hESC) reporter line was generated that allowed monitoring of neural crest cell induction in vitro as this cell line responds to contact with small molecules. Sox10 was the most robust early marker of multipotent neural crest stem cells and was also found expressed in some neural crest derivatives, including melanocyte progenitors. This reporter system was used to prospectively identify and isolate neural crest populations in the development of a directed differentiation scheme in order to produce melanocyte cultures with higher purity and numbers than obtained with previous maturation schemes (FIG. 14, LSB-C).

In a dual SMAD inhibition protocol (Chambers, et al. Nat. Biotech. (2009), herein incorporated by reference), human pluripotent stem cells (hPSCs) treated with two small molecules to inhibit SMAD signaling efficiently produced CNS neural tissues. Additionally when hESC was plated at lower densities, low levels of spontaneous neural crest cell induction was observed (for example, approximately 3% Sox10:: GFP+ neural crest type cells were observed). However, for use in research and for medical studies, larger numbers of neural crest type cells were needed. Further, for melanocyte research, a purer population with larger numbers of cells were necessary that were not provided with the low level spontaneous differentiation.

During the development of the present inventions the inventors discovered methods to optimize the dual SMAD inhibition protocol for neural crest induction in a manner that would produce highly pure yields of melanocyte precursors, maturing melanocytes and mature melanocytes.

Specifically, the following time line of culturing conditions was developed that produced melanocytes of the present inventions: Feed on Day 0 and 1 with LDN and SB (using the same concentration ranges as LDN and SB in methods comprising 3i); Feed on Day 2 with LDN, SB, CHIR (using the same concentration ranges as LDN, SB, and CHIR in methods comprising 3i as described herein); In one embodiment, Feed on Day 3 with SB, CHIR (using the same concentration ranges as SB and MR in methods comprising 3i as described herein), in another embodiment Feed on Day 3 with LDN, SB, CHIR (using the same concentration ranges as LDN, SB, and CHIR in methods comprising 3i as described herein); Feed on Day 4 and 5 CHIR (using the same concentration ranges as CHIR in methods comprising 3i as described herein); Feed on Day 6 to 11 CHIR, BMP4, and EDN3 (using the same concentration ranges as CHIR in methods comprising 3i as described herein, see concentration ranges below for BMP4 and EDN3). On day 11 cells were passaged and fed with MEL media (including CHIR) up to 8 weeks.

MEL media enriched for melanocytes such that by 8 weeks the cell cultures showed up to 100% of a pure population. Thus this LSB-MEL method/protocol had a high efficiency of melanocyte production. The inventors also discovered during the development of melanocytes that Linoleic Acid was at least one required ingredient in the MEL medium (see, FIG. 16).

During the development of melanocytes, multiple precursor stages were observed in the following order: neural crest stem cell, embryonic glial-melanoblast stem cell, adult melanocyte stem cell, melanocyte, see, exemplary schematic in FIG. 13.

FIG. 13. Specification and isolation of melanocyte progenitors/melanoblasts.

The 11-day LSB-C protocol supported the derivation of Sox10::GFP, MITF co-expressing melanocyte progenitors (A, right panel). MITF single positive populations was observed (A, left panel). c-Kit was identified as a potential marker of melanocyte progenitors. A low percentage of Sox10:: GFP, c-kit co-expressing cells were observed after LSB-C differentiation (B, orange population). qRT-PCR analysis confirmed the enrichment of melanocyte markers MITFM (a basic-helix-loop-helix-leucine zipper protein) and Dct (Dopachrome tautomerase (dopachrome delta-isomerase, tyrosine-related protein 2)) in the double positive population (C). Treatment with BMP4 and EDN3 ("LSB-Mel") enhanced induction of the Sox10::GFP, c-kit double positive putative melanocyte progenitor population (D). Sox10:: GFP, c-kit double positive cells isolated following LSB-Mel treatment exhibited significantly higher levels of melanocyte markers MITFM and Dct (E). Error bars represent s.e.m. * p<0.05.

FIG. 14. Expansion and Maturation of Melanocyte Precursors.

Summary of differentiation conditions (A). Following specification in LSB-C conditions with BMP4 and EDN3 (LSB-Mel) cells were sorted at day 11 and replated. Post-sort (PS) cells were maintained in maturation media containing c-kit ligand (SCF), endothelin 3 (EDN3), fibroblast growth factor (FGF), and Wnt activators. Pigmented cells observed by brightfield microscopy at day 6 PS were positive for the melanocyte marker MITF but appeared to have downregulated the Sox10::GFP reporter (B). All populations except the Sox10::GFP, c-kit double negative eventually gave rise to MITF expressing cells and macroscopic pigmented clusters, but at differing rates (C). Treatment with BMP4 and cAMP enhanced the differentiation into pigmented cells exhibiting a spindle-like morphology typical of melanocytes (D).

FIG. 15. Characterization of Mature Melanocytes.

Pure populations of mature melanocytes derived with the LSB-Mel protocol maintain the expression of common melanocyte markers including MITF, Sox10, Tyrp1 (Tyrosinase-related protein 1), and HMB45 after greater than 8 weeks in culture (A). Melanocytes retain their darkly pigmented phenotype over several weeks in passage (B). 1×10⁶ cells were pelleted and photographed to assess pigmentation levels. Electron microscopic ultrastructural characterization of mature melanocytes (C, D). The presence of numerous darkly pigmented melanosomes in the cytoplasm of LSB-Mel derived melanocytes were observed by TEM (C). Note the presence and progressive deposition of melanin pigment with the maturation of melanosome vesicles from stages I through IV (D).

Therefore, the inventors demonstrated that a dual SMAD inhibition protocol, LSB, rapidly and efficiently generated Sox10::GFP expressing neural crest populations from human embryonic stem cells. This modified protocol supported the induction of low levels of melanocyte progenitors, which were prospectively identified and isolated by c-kit expression. Induction of these cells was further enhanced through treatment with BMP4 and EDN3. Melanocyte progenitors were subsequently matured to a pigmented state following additional culture in vitro in the presence of BMP4 and cAMP.

Cell Medium for LSB-MEL:

| Mel-1 Media: | | |
|---|---|---|
| NeuroBasal | Invitrogen 21103049 | 50% |
| DMEM Low Glucose | Invitrogen 11885 | 30% |
| MCDB201 | Sigma M6770 | 20% |
| B27 | Invitrogen 17504-044 | 2% |
| ITS | Sigma I314 | 1% |
| Linoleic Acid-BSA | Sigma L9530 | 1% |
| L-glut | Gibco 25030-164 | 250 nM |
| Dexamethasone | Sigma D2915 | 0.05 uM |
| Cholera Toxin | Sigma C8052 | 50 ng/ml |
| L-AA | Sigma A5960 | 100 uM |
| SCF | Peprotech 300-07 | 50 ng/ml |
| EDN3 | American Peptide Company 88-5-10B | 100 nM |
| FGF2 | R&D 233-FB-001MG/CF | 4 ng/ml |
| cAMP | Sigma D-0260 | 500 uM |
| BMP4 | R&D 314-bp | 25 ng/ml |
| Chir | Stemgent 04-0004 | 3 uM |

| Day 6-11: | | |
|---|---|---|
| BMP4 | R&D 314-bp | 25 ng/ml |
| EDN3 | American Peptide Company 88-5-10B | 100 nM |

Concentration ranges for BMP4 from R&D: used between 10 ng/ml to 100 ng/ml (in one embodiment at 25 ng/ml), and EDN from American Peptide Company is used at 25-300 nM (in one embodiment at 100 nM).

FIG. 16. Shows an exemplary LSB-MEL medium formulation that required Linoleic Acid for growth of melanocytes. Medium component shown above microscopic views represent the medium component left out of the formulation; Ph=phase contrast; BF=bright filed. An exemplary schematic shows melanocyte progenitor markers used for identifying cells of the present inventions.

Thus the inventors discovered and developed a rapid and defined protocol for the induction of neural crest in vitro. Further, the inventors used this rapid and defined protocol for the induction of neural crest cells in vitro for developing compositions and methods for directed differentiation of these cells into melanocytes. These melanocytes were unique in their capability for long-term culture and continuous production of eumelanin.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in cellular biology, neurobiology, cancer cell biology, molecular biology, biochemistry, chemistry, organic synthesis, or related fields are intended to be within the scope of the following claims.

The invention claimed is:

1. A kit comprising a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling, further comprising instructions for inducing directed differentiation of a pluripotent stem cell into a differentiated neural crest lineage cell or a neuronal lineage cell, in vitro, comprising (i) contacting said stem cell with said first and said second inhibitors for up to 96 hours and (ii) contacting said stem cell with said third inhibitor for up to 240 hours.

2. The kit of claim 1, wherein said first inhibitor is SB431542.

3. The kit of claim 1, wherein said second inhibitor is LDN193189.

4. The kit of claim 1, wherein said third inhibitor is CHIR99021.

5. A kit comprising a first signaling inhibitor, a second signaling inhibitor, and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling, and said third inhibitor is capable of lowering glycogen synthase kinase 3β (GSK3β) for activation of wingless (Wnt) signaling, further comprising a fourth inhibitor that lowers fibroblast growth factor (FGF) receptor family signaling, wherein said FGF receptor family signaling comprising vascular endothelial growth factor (VEGF) receptor signaling, fibroblast growth factor (FGF) receptor signaling, and platelet-derived growth factor (PDGF) tyrosine kinase receptor signaling.

6. The kit of claim 5, wherein said fourth inhibitor is SU5402.

7. A kit comprising a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling, further comprising an inhibitor capable of lowering Notch signaling.

8. The kit of claim 7, wherein said inhibitor that is capable of lowering Notch signaling is selected from the group consisting of N—[N-(3,5-Difluorophenacetyl)-L-alanyl]-S-phenylglycine t-butyl ester (DAPI) and (N—[N-(3,5-difluorophenacetyl)-L-alanyl]-(S)-phenylglycine-4-(4-(8 biotinamido)octylamino)benzoyl)benzyl)methylamide).

9. The kit of claim 1, further comprising, one or more antibody used for the detection of expression of one or more protein(s) selected from the group consisting of nestin, OCT4, PAX6, TUJ1, SOX10, NTRK1, ISL1, POU4F1 (BRN3A), NEUROG2, NEUROG1, MAP2, OTX2, DLK1, DKK1, CUZD1, MSX1, ID2, AP2B, ETS1, FOXD3, NGN1, DCX, TUBB3, SYT4, STMN2, INA, GAP43, TAC1, VGLUT2, SLC15A3, and TRPV1.

10. The kit of claim 1, further comprising, one or more pair of PCR primers for the detection of mRNA expression of one or more gene(s) selected from the group consisting of nestin, OCT4, PAX6, TUJ1, SOX10, NTRK1, ISL1, POU4F1 (BRN3A), NEUROG2, NEUROG1, MAP2, OTX2, DLK1, DKK1, CUZD1, MSX1, ID2, AP2B, ETS1, FOXD3, NGN1, DCX, TUBB3, SYT4, STMN2, INA, GAP43, TAC1, VGLUT2, SLC15A3, and TRPV1.

11. The kit of claim 1, further comprising, one or more antibody used for the detection of expression of one or more protein(s) selected from the group consisting of Protachykinin-1 (TAC1), vesicular glutamate transporter 2 (VGLUT2) and solute carrier family 15, member 3 (SLC15A3).

12. The kit of claim 1, further comprising, one or more pair of PCR primers for the detection of mRNA expression of one or more gene(s) selected from the group consisting of Protachykinin-1 (TAC1), vesicular glutamate transporter 2 (VGLUT2) and solute carrier family 15, member 3 (SLC15A3).

13. The kit of claim 1, further comprising, instructions comprising steps for adding the first and second inhibitor two days before adding the third inhibitor.

14. The kit of claim 1, further comprising, instructions comprising steps for making neural stem cell precursors and making nociceptor cells.

15. The kit of claim 1, further comprising a human pluripotent stem cell.

16. The kit of claim 15, wherein said human pluripotent stem cell is a human embryonic stem cell.

17. The kit of claim 15, wherein said human pluripotent stem cell is a human induced pluripotent stem cell.

18. The kit of claim 13, wherein said human pluripotent stem cell is a transgenic human pluripotent stem cell (hPSC) containing a bacterial artificial chromosome (BAC) comprising a SOX10 gene having an inserted reporter sequence encoding a green fluorescent protein.

19. A method for inducing directed differentiation of a pluripotent stem cell, comprising a) providing, in vitro:
  i) a cell culture comprising human pluripotent stem cells; and
  ii) a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling;
b) contacting said stem cell with said first and said second inhibitors for up to 96 hours; and
c) contacting said stem cell with said third inhibitor for up to 240 hours;
wherein a differentiated neural crest lineage cell or a neuronal lineage cell is produced.

20. The method of claim 19, wherein said first inhibitor is SB431542.

21. The method of claim 19, wherein said second inhibitor is LDN193189.

22. The method of claim 19, wherein said third inhibitor is CHIR99021.

23. The method of claim 19, further comprising contacting said stem cell with a fourth inhibitor that lowers fibroblast growth factor (FGF) receptor family signaling, wherein said FGF receptor family signaling comprising vascular endothelial growth factor (VEGF) receptor signaling, fibroblast growth factor (FGF) receptor signaling, and platelet-derived growth factor (PDGF) tyrosine kinase receptor signaling.

24. The method of claim 23, wherein said fourth inhibitor is SU5402.

25. The method of claim 23, further comprising contacting said stem cell with a fifth inhibitor capable of lowering Notch signaling, wherein a neural crest lineage cell is produced.

26. The method of claim 25, wherein said fifth inhibitor is selected from the group consisting of N—[N-(3,5-Difluorophenacetyl)-L-alanyl]-S-phenylglycine t-butyl ester (DAPT) and (N—[N-(3,5-difluorophenacetyl)-L-alanyl]-(S)-phenylglycine-4-(4-(8 biotinamido)octylamino)benzoyl)benzyl)methylamide).

27. The method of claim 19, further comprising contacting said stem cell with a fourth inhibitor and a fifth inhibitor, wherein said fourth inhibitor is SU5402 and said fifth inhibitor is N—[N-(3,5-Difluorophenacetyl)-L-alanyl]-S-phenylglycine t-butyl ester (DAPT) for directed differentiated of a neural crest lineage cell into a peptidergic nociceptor cell.

28. The method of claim 27, wherein said peptidergic nociceptor cell expresses a marker selected from the group consisting of OCT4, DLK1, PAX6, SOX10, POU4F1 (BRN3A), ISL1, NEUROG2, NEUROG1, NTRK1, RET, RUNX1, VGLUT2, TAC1, and TRPV1.

29. The method of claim 27, wherein said peptidergic nociceptor cell expresses a marker selected from the group consisting of ISL1, POU4F 1 (BRN3A), RET, RUNX1, and NTRK1.

30. The method of claim 27, wherein said peptidergic nociceptor cell co-expresses Substance P and Calcitonin gene related peptide (CGRP).

31. The method of claim 27, wherein said peptidergic nociceptor cell produces an action potential in response to external stimuli, wherein said external stimuli is an electrical current.

32. The method of claim 27, wherein said differentiated peptidergic nociceptor cell is present within a highly enriched populations of neurons within 10-15 days after contacting said stem cell with said first and said second inhibitor.

33. The method of claim 19, wherein said pluripotent stem cell is a human embryonic stem cell.

34. The method of claim 19, wherein said pluripotent stem cell is a human induced pluripotent stem cell.

35. A method of screening a biological agent in vitro, comprising,
  a) providing:
    i) a nociceptor cell derived in vitro from directed differentiation of the stem cell obtained from a method comprising contacting, in vitro, a cell culture comprising human pluripotent stem cells with a first signaling inhibitor, a second signaling inhibitor and a third signaling inhibitor, wherein said first inhibitor is capable of lowering transforming growth factor beta (TGFβ)/Activin-Nodal signaling, said second inhibitor is capable of lowering Small Mothers Against Decapentaplegic (SMAD) signaling and said third inhibitor is capable of lowering glycogen synthase kinase 3β (GSK3β) for activation of wingless (Wnt) signaling, and wherein said stem cell is contacted with said first and second inhibitors for up to 96 hours and said stem cell is contacted with said third inhibitor for up to 240 hours; and
    ii) a test compound; and
  b) contacting said nociceptor cell with said test compound and measuring nociceptor function, wherein said function is g measurement of an action potential.

* * * * *

UNITED STATES PATENT AND TRADEMARK OFFICE
CERTIFICATE OF CORRECTION

PATENT NO. : 9,453,198 B2  
APPLICATION NO. : 13/697274  
DATED : September 27, 2016  
INVENTOR(S) : Lorenz Studer It is certified that error appears in the above-identified patent and that said Letters Patent is hereby corrected as shown below:

In the Specification

In Column 1, beginning at Line 10 please insert:
--This invention was made with government support under grant number NS066390 awarded by the National Institutes of Health. The government has certain rights in the invention.--

Signed and Sealed this
Twentieth Day of March, 2018

Andrei Iancu
*Director of the United States Patent and Trademark Office*

SEQUENCE LISTING

<160> NUMBER OF SEQ ID NOS: 56

<210> SEQ ID NO 1
<211> LENGTH: 238
<212> TYPE: PRT
<213> ORGANISM: Homo sapiens

<400> SEQUENCE: 1

Met Glu Pro Gly Leu Trp Leu Leu Phe Gly Leu Thr Val Thr Ser Ala
1               5                   10                  15

Ala Gly Phe Val Pro Cys Ser Gln Ser Gly Asp Ala Gly Arg Arg Gly
            20                  25                  30

Val Ser Gln Ala Pro Thr Ala Ala Arg Ser Glu Gly Asp Cys Glu Glu
        35                  40                  45

Thr Val Ala Gly Pro Gly Glu Glu Thr Val Ala Gly Pro Gly Glu Gly
    50                  55                  60

Thr Val Ala Pro Thr Ala Leu Gln Gly Pro Ser Pro Gly Ser Pro Gly
65                  70                  75                  80

Gln Glu Gln Ala Ala Glu Gly Ala Pro Glu His His Arg Ser Arg Arg
                85                  90                  95

Cys Thr Cys Phe Thr Tyr Lys Asp Lys Glu Cys Val Tyr Tyr Cys His

```
            100             105             110
Leu Asp Ile Ile Trp Ile Asn Thr Pro Glu Gln Thr Val Pro Tyr Gly
        115                 120                 125
Leu Ser Asn Tyr Arg Gly Ser Phe Arg Gly Lys Arg Ser Ala Gly Pro
        130                 135                 140
Leu Pro Gly Asn Leu Gln Leu Ser His Arg Pro His Leu Arg Cys Ala
145                 150                 155                 160
Cys Val Gly Arg Tyr Asp Lys Ala Cys Leu His Phe Cys Thr Gln Thr
                165                 170                 175
Leu Asp Val Ser Ser Asn Ser Arg Thr Ala Glu Lys Thr Asp Lys Glu
                180                 185                 190
Glu Glu Gly Lys Val Glu Val Lys Asp Gln Gln Ser Lys Gln Ala Leu
                195                 200                 205
Asp Leu His His Pro Lys Leu Met Pro Gly Ser Gly Leu Ala Leu Ala
            210                 215                 220
Pro Ser Thr Cys Pro Arg Cys Leu Phe Gln Glu Gly Ala Pro
225                 230                 235

<210> SEQ ID NO 2
<211> LENGTH: 232
<212> TYPE: PRT
<213> ORGANISM: Mus musculus

<400> SEQUENCE: 2

Met Glu Arg Cys Pro Ser Leu Gly Val Thr Leu Tyr Ala Leu Val Val
1               5                   10                  15
Val Leu Gly Leu Arg Ala Ala Pro Ala Gly Gly Gln His Tyr Leu His
                20                  25                  30
Ile Arg Pro Ala Pro Ser Asp Asn Leu Pro Leu Val Asp Leu Ile Glu
            35                  40                  45
His Pro Asp Pro Ile Phe Asp Pro Lys Glu Lys Asp Leu Asn Glu Thr
        50                  55                  60
Leu Leu Arg Ser Leu Leu Gly Gly His Tyr Asp Pro Gly Phe Met Ala
65                  70                  75                  80
Thr Ser Pro Pro Glu Asp Arg Pro Gly Gly Gly Gly Pro Ala Gly
                85                  90                  95
Gly Ala Glu Asp Leu Ala Glu Leu Asp Gln Leu Leu Arg Gln Arg Pro
                100                 105                 110
Ser Gly Ala Met Pro Ser Glu Ile Lys Gly Leu Glu Phe Ser Glu Gly
            115                 120                 125
Leu Ala Gln Gly Lys Lys Gln Arg Leu Ser Lys Lys Leu Arg Arg Lys
        130                 135                 140
Leu Gln Met Trp Leu Trp Ser Gln Thr Phe Cys Pro Val Leu Tyr Ala
145                 150                 155                 160
Trp Asn Asp Leu Gly Ser Arg Phe Trp Pro Arg Tyr Val Lys Val Gly
                165                 170                 175
Ser Cys Phe Ser Lys Arg Ser Cys Ser Val Pro Glu Gly Met Val Cys
                180                 185                 190
Lys Pro Ser Lys Ser Val His Leu Thr Val Leu Arg Trp Arg Cys Gln
                195                 200                 205
Arg Arg Gly Gly Gln Arg Cys Gly Trp Ile Pro Ile Gln Tyr Pro Ile
            210                 215                 220
Ile Ser Glu Cys Lys Cys Ser Cys
225                 230
```

```
<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
cagctgtgtg tactcaatga tagatttc                                      28

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ggagaatttg gctggaactg catg                                          24

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
cctgaagcag aagaggatca cc                                            22

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
catagtcgct gcttgatcgc                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
gaaccgagtg agaggcaacc t                                             21

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
gggcgatgtg gctgatct                                                 18

<210> SEQ ID NO 9
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 9
caacatgatg gagacggagc                                              20

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
gcagcgtgta cttatccttc ttc                                          23

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
agccacatcg ctcagacacc                                              20

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
gtactcagcg ccagcatcg                                               19

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gcaccgtcaa ggctgagaac                                              20

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
cgccccactt gattttgg                                                18

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccaacaccgt gaggagcttc                                              20

<210> SEQ ID NO 16
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 16
gtccgagtct gatggaggtg                                                   20

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
gtgcttccac cactgccaat aac                                               23

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
gttcatctcc agtgggtttc tcaa                                              24

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gatcaccagc cactgcttcc                                                   20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
ctccgggttc ctccatcatc t                                                 21

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ggagtgaatc agctcggtgg                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
```

-continued

```
ggtctgcccg ttcaacatcc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gggcacttat cgctgtgagg                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
ctcgccagcc ttgttctcag                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gcaagatggc ccaggagaac                                              20

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
cttgtccttc ttgagcagcg t                                            21

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gagaacccca agatgcacaa                                              20

<210> SEQ ID NO 28
<211> LENGTH: 19
<212> TYPE: DNA
<213> ORGANISM: Artificial Sequence
<220> FEATURE:
<223> OTHER INFORMATION: Synthetic

<400> SEQUENCE: 28
cctcggacat gaccttcca                                               19

<210> SEQ ID NO 29
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 29
actcagaact cgctgggcaa c                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
cgtgggggaa aaagtaactg g                                              21

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
caagtcagcg cccaagcaag tcaag                                          25

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
gagccggcca tggagttcaa gtcgt                                          25

<210> SEQ ID NO 33
<211> LENGTH: 22
<212> TYPE: DNA
<213> ORGANISM: Artificial Sequence
<220> FEATURE:
<223> OTHER INFORMATION: Synthetic

<400> SEQUENCE: 33
cactcccaca caagtaggca ac                                             22

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
catacatcac attccgagtc gctg                                           24

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gggccaaagt ggcttccttc                                                20
```

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
caggagacat gagaccaggg ac                                          22

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
cgatatctgg gtcatcgctt cc                                          22

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gaggtcacgt ctatttcctc cg                                          22

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
cagctccacg accactgaa                                              19

<210> SEQ ID NO 40
<211> LENGTH: 19
<212> TYPE: DNA
<213> ORGANISM: Artificial Sequence
<220> FEATURE:
<223> OTHER INFORMATION: Synthetic

<400> SEQUENCE: 40
tccatggcaa acaccgtcc                                              19

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ccaattacaa ccccgacatc                                             20

<210> SEQ ID NO 42
<211> LENGTH: 20
<212> TYPE: DNA
<213> ORGANISM: Artificial Sequence
<220> FEATURE:

<223> OTHER INFORMATION: Synthetic

<400> SEQUENCE: 42
ccgagttctc tgctttcacc                                               20

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
tactgcaacg gcaacctg                                                 18

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
gccatgttct tgctcacgtc                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
cgctctcgaa ccgcctacac                                               20

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
gcagtttgtg gtctttcttc cact                                          24

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
ccctggatgc gcaaagttca c                                             21

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ggtgttgggc aacttgtggt                                               20

```
<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
ggcccaagct aaagttggtt ctc                                           23

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
gcagtgacat cctcagccaa ag                                            22

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
tcatctgatg cagaatggta agagg                                         25

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
gtagcccaca aagactttgc c                                             21

<210> SEQ ID NO 53
<211> LENGTH: 25
<212> TYPE: DNA
<213> ORGANISM: Artificial Sequence
<220> FEATURE:
<223> OTHER INFORMATION: Synthetic

<400> SEQUENCE: 53
gggagaagca gctcaactcc aatcc                                         25

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
ccagcaaggc ctggaagag                                                19

<210> SEQ ID NO 55
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 55
ccgccacttg caggagtacc ag                                          22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
ttctgctcgg gcccctcatg ag                                          22
```